US006936245B1

(12) United States Patent
Zeng et al.

(10) Patent No.: US 6,936,245 B1
(45) Date of Patent: Aug. 30, 2005

(54) MEDIATORS OF SIGNAL TRANSDUCTION

(75) Inventors: Wenlin Zeng, Union City, CA (US); Lawrence Stanton, Redwood City, CA (US); Haiyan Kong, Sunnyvale, CA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/548,473

(22) Filed: Apr. 13, 2000

Related U.S. Application Data

(60) Provisional application No. 60/129,553, filed on Apr. 16, 1999, now abandoned.

(51) Int. Cl.$^7$ .......................... A61K 38/51; C12N 9/12; C12Q 1/48

(52) U.S. Cl. .................. 424/94.5; 435/194; 435/15

(58) Field of Search ................ 435/194, 15; 424/185.1, 424/94.5

(56) References Cited

PUBLICATIONS

Adams, et al., *Journal of Cell Biology*, 111:131–142, Jul. 1990, "CDC42 and CDC43, Two Additional Genes Involved in Budding and the Establishment of Cell Polarity in the Yeast *Saccharomyces cerevisiae*."
Aepfelbacher, et al., *Proc. Natl. Acad. Sci. USA*, 91:4263–4267, May 1994, "Spreading of differentiating human monocytes is associated with a major increase in membrane-bound CDC42."
Altschul, et al., *Nucleic Acids Research*, 25(17):3389–3402, 1997, "Gapped Blast and PSI–Blast: a new generation of protein database search programs."
Braga, et al., *Journal of Cell Biology*, 137(6):1421–1431, Jun. 16, 1997, "The Small GTPases Rho and Rac Are Required for the Establishment of Cadherin–dependent Cell–Cell Contacts."
Brenner, et al., *Journal of Biological Chemistry*, 272(35):22173–22181, Aug. 29, 1997, "Fas– or Ceramide–induced Apoptosis Is Mediated by a Rac1–regulated Activation of Jun N–terminal Kinase/p38 Kinases and GADD153."
Cherfils, J. and P. Chardin, *TIBS*, 24:306–311, Aug. 1999, "GEFs: structural basis for their activation of small GTP–binding proteins."
Coso, et al., *Cell*, 81:1137–1146, Jun. 30, 1995, "The Small GTP–Binding Proteins Rac1 and Cdc42 Regulate the Activity of the JNK/SAPK Signaling Pathway."
Debant, et al., *Proc. Natl. Acad. Sci. USA*, 93:5466–5471, May 1996, "The multidomain protein Trio binds the LAR transmembrane tyrosine phosphatase, contains a protein kinase domain, and has separate rac–specific and rho–specific guanine nucleotide exchange factor domains."

Dutartre, et al., *Journal of Cell Science*, 109:367–377, 1996, "Cytokinesis arrest and redistribution of actin–cytoskeleton regulatory components in cells expressing the RHO GTPase CDC42Hs."
Esteve, et al., *Oncogene*, 11:2657–2665, 1995, "Induction of apoptosis by rho in NIH 3T3 cells requires two complementary signals. Ceramides function as a progression factor for apoptosis."
Gulbins, et al., *Journal of Biological Chemistry*, 271(42):26389–26394, Oct. 18, 1996, "Fas–induced Apoptosis Is Mediated by Activation of a Ras and Rae Protein–regulated Signaling Pathway."
Hirai, et al., *Journal of Biological Chemistry*, 272(1):13–16, Jan. 3, 1997, "Geranylgeranylated Rho Small GTPases(s) Are Essential for the Degradation of p27$^{Kip1}$ and Facilitate the Progression from $G_1$ to S Phase in Growth–stimulated Rat FRTL–5 Cells."
Hirata, et al., *Journal of Biological Chemistry*, 267(13):8719–8722, May 5, 1992, "Involvement of rho p21 in the GTP–enhanced Calcium Ion Sensitivity of Smooth Muscle Contraction."
Jimenez, et al., *Oncogene*, 10:811–816, 1995, "Induction of apoptosis in NIH'3T3 cells after serum deprivation by overexpression of rho–p21, a GTPase protein of the ras superfamily."
Katagiri, et al., *Journal of Cell Biology*, 127(6) part 1:1755–1766, Dec. 1994, "Bone Morphogenetic Protein–2 Converts the Differentiation Pathway of C2C12 Myoblasts into the Osteoblast Lineage."
Khosravi–Far, et al., *Molecular and Cellular Biology*, 16(7):3923–3933, Jul. 1996, "Oncogenic Ras Activation of Raf/Mitogen–Activated Protein Kinase–Independent Pathways Is Sufficient To Cause Tumorigenic Transformation."
Lamaze, et al., *Nature*, 382:177–179, Jul. 11, 1996, "Regulation of receptor–mediated endocytosis by Rho and Rac."
Lechner, et al., *Proc. Natl. Acad. Sci. USA*, 93:4355–4359, Apr. 1996, "ERK6, a mitogen–activated protein kinase involved in C2C12 myoblast differentiation."
Minden, et al., *Cell*, 81:1147–1157, 1995, "Selective Activation of the JNK Signaling Cascade and c–Jun Transcriptional Activity by the Small GTPases Rac and Cdc42Hs."

(Continued)

Primary Examiner—Tekchand Saidha
Assistant Examiner—Malgorzata A. Walicka
(74) Attorney, Agent, or Firm—Knobbe, Martens, Olson & Bear, LLP

(57) ABSTRACT

Polypeptides capable of regulating signal transduction, which preferably exhibit kinase activity, or antibodies against such polypeptides that inhibit the interaction of these polypeptides with other mediators of signal transduction, may be used in the identification, prevention or treatment of disease, preferably cardiac disease, in mammalian hosts. In addition, these polypeptides can facilitate the identification or isolation of additional mediators of signal transduction associated with disease, preferably cardiac disease, which in turn may also be used in the identification, prevention or treatment of disease, preferably cardiac disease, in mammals.

8 Claims, 19 Drawing Sheets

OTHER PUBLICATIONS

Moorman, et al., *Journal of Immunology*, 156:4146–4153, 1996, "Inactivation of the Small GTP Binding Protein Rho Induces Multinucleate Cell Formation and Apoptosis in Murine T Lymphoma EL4[1,2]."

Mourey, R. and J. Dixon, *Current Opinion in Genetics and Development*, 4:31–39, 1994, "Protein tyrosine phosphatases: characterization of extracellular and intracellular domains."

Namiki, et al., *Journal of Biological Chemistry*, 272(35):22046–22052, Aug. 29, 1997, "A Kinase Domain–truncated Type I Receptor Blocks Bone Morphogenetic Protein–2–induced Signal Transduction in C2C12 Myoblasts."

Nobes, C. and A. Hall, *Cell*, 81:53–62, Apr. 7, 1995, "Rho, Rac, and Cdc42 GTPases Regulate the Assembly of Multimolecular Focal Complexes Associated with Actin Stress Fibers, Lamellipodia, and Filopodia."

Olson, et al., *Science*, 269:1270–1272, Sep. 1, 1995, "An Essential Role for Rho, Rac, and Cdc42 GTPases in Cell Cycle Progression Through $G_1$."

Qiu, et al., *Molecular and Cellular Biology*, 17(6):3449–3458, Jun. 1997, "Cdc42 Regulates Anchorage–Independent Growth and Is Necessary for Ras Transformation."

Roux, et al., *Current Biology*, 7:629–637, 1997, "The Small GTPases Cdc42Hs, Rac1 and RhoG delineate Raf–independent pathways that cooperate to transform NIH3T3 cells."

Seipl, et al., *Journal of Cell Science*, 112:1825–1834, 1999, "Trio amino–terminal guanine nucleotide exchange factor domain expression promotes actin cytoskeleton reorganization, cell migration and anchorage–independent cell growth."

Tapon, N. and A. Hall, *Current Opinion in Cell Biology*, 9:86–92, 1997, "Rho, Rac and Cdc42 GTPases regulate the organization of the actin cytoskeleton."

FIG. 2

| FIG. 2A |
|---|
| FIG. 2B |
| FIG. 2C |
| FIG. 2D |
| FIG. 2E |
| FIG. 2F |

FIG. 2A

```
                                                                                - - Majority
                        10        20        30        40
                                                      Q - H19G5-F1.pep
 1  M G P G D I S L P G R P K P G P C S S P G S A S Q A S S S Q V S S L R V G S S
 1  M A - - - - - - - - - - - - - - - - - - - - - - - - - - - - - - - - - - - -  - R19G5-S.pep
 1  M A - - - - - - - - - - - - - - - - - - - - - - - - - - - - - - - - - - - -  - M19G5-S.pep

- - Majority
                        50        60        70        80
41  V G T E P G P S L D A E G W T Q E A E D L S D S T P T L Q R P Q E Q A T M R K F  H19G5-F1.pep
 3  - - - - - - - - - - - - - - - - - - - - - - - - - - - - - - - - - - - - - -    R19G5-S.pep
 3  - - - - - - - - - - - - - - - - - - - - - - - - - - - - - - - - - - - - - -    M19G5-S.pep

- - Majority
                        90        100       110       120
81  S L G G R G G Y A G V A G Y G T F A F G G D A G G M L G Q G P M W A R I A W A V  H19G5-F1.pep
 3  - - - - - - - - - - - - - - - - - - - - - - - - - - - - - - - - - - - - - -    R19G5-S.pep
 3  - - - - - - - - - - - - - - - - - - - - - - - - - - - - - - - - - - - - - -    M19G5-S.pep
```

FIG. 2B

```
                                                                                                    - - Majority
         130         140         150         160
121 SQSEEEEQEEARARAESQSEEQQEARAESPLPQVSARPVPEV H19G5-F1.pep
  3 ---------------------------------------- R19G5-S.pep
  3 ---------------------------------------- M19G5-S.pep

- - Majority
         170         180         190         200
161 GRAPTRSSPEPTPWEDIGQVSLVQIRDLSGDAEAADTISL H19G5-F1.pep
  3 ---------------------------------------- R19G5-S.pep
  3 ---------------------------------------- M19G5-S.pep

- - Majority
         210         220         230         240
201 DISEVDPAYLNLSDLYDIKYLPFEFMIFRKVPKSAQPEPP H19G5-F1.pep
  3 ---------------------------------------- R19G5-S.pep
  3 ---------------------------------------- M19G5-S.pep

- - Majority
         250         260         270         280
241 SPMAEEELAEFPEPTWPWPGELGPHAGLEITEESEDVDAL H19G5-F1.pep
  3 ---------------------------------------- R19G5-S.pep
  3 ---------------------------------------- M19G5-S.pep
```

FIG. 2C

```
                                                                                        Majority
          290        300        310        320
281 L A E A A V G R K R K W S S P S R S L F H F P G R H L P L D E P A E L G L R E R     H19G5-F1.pep
  3 - - - - - - - - - - - - - - - - - - - - - - - - - - - - - - - - - - - - - - -     R19G5-S.pep
  3 - - - - - - - - - - - - - - - - - - - - - - - - - - - - - - - - - - - - - - -     M19G5-S.pep H I S R I L K G R P E G P E K E G P P R K K A G L A S F R L S G L K  Majority
          330        340        350        360
321 V K A S V E H I S R I L K G R P E G L E K E G P P R K K A G L A S F R L S G L K     H19G5-F1.pep
  3 - - - - - H I S R I L K G P K P E G P P R K K A G L A S F R L S G L K               R19G5-S.pep
  3 - - - - - H I S R I L K G R P P E G R E G P P R K K A G L A S F R L S G L K         M19G5-S.pep G R D Q A P S F L R E L S D E A V V L G Q S V T L A C Q V L A Q P T A Q A T W S     Majority
          370        380        390        400
361 S W D R A P T F L R E L S D E T V V L G Q S V T L A C Q V S A Q P A A Q A T W S     H19G5-F1.pep
 37 G R D Q A P S F L R E L S D E A V V L G Q S V T L A C Q V L A Q P T A Q A T W S     R19G5-S.pep
 37 G R D Q A P S F L R E L S D E A V V L G Q S V T L A C Q V L A Q P T A Q A T W S     M19G5-S.pep K D G A L L E S S G H L L I S S T L K N F Q L L T I L V V X E E D L G T Y T C C     Majority
          410        420        430        440
401 K D G A P L E S S G H L L I S S R V L I S A T L K N F Q L L T I L V V V A E D L G V Y T C S   H19G5-F1.pep
 77 K D G A L L E S S G H L L I S S T L K N F Q L L T I L V V T E E D L G T Y T C C     R19G5-S.pep
 77 K D G V L L E S S G H L L I S S T L K N F Q L L T I L V V K E E D L G T Y T C C     M19G5-S.pep
```

FIG. 2D

```
      V S N P L G T A V T T G V L R K A E R P S S S P R P E V G E L Y X D A V L L V W  Majority
                         450                 460                 470                 480
441   V S N   A L G T V T T G V L R K A E R P S S S P C P D I G E V Y A D G V L L V W  H19G5-F1.pep
117   V S N P L G T A V T T G V L R K A E R P S S S P R P E V G E L Y T D A V L L V W  R19G5-S.pep
117   V S N P L G T A V T T G V L R K A E R P S S S P R P E V G E L Y K D A V L L V W  M19G5-S.pep K P V E S Y G P V T Y I V Q C C I E G G S W T T L A S D I S D C C Y L T G K L S  Majority
                         490                 500                 510                 520
481   K P V E S Y G P V T Y I V Q C S L E G G S W T T L A S D I F D C C Y L T S K L S  H19G5-F1.pep
157   K P V E S Y G P V T Y I V Q C C I E G G S W T T L A S D I S D C C Y L T G K L P  R19G5-S.pep
157   K P V E S C G P V T Y I V Q C C I E G G S W T T L A S D I S D C C Y L T G K L S  M19G5-S.pep R G G M Y T F R T A C V S K A G M G P Y S S P S E Q V L L G G P N H L A S E E E  Majority
                         530                 540                 550                 560
521   R G G T Y T F R T A C V S K A G M G P Y S S P S E Q V L L G G P S H L A S E E E  H19G5-F1.pep
197   R G G M Y T F R T A C V S K A G M G P Y S S P S E Q V L L G G P N H L A S E E E  R19G5-S.pep
197   R G G M Y I F R T A C V S K A G M G P Y S S P S E Q V L L G G P N H L A S E E E  M19G5-S.pep S S R G R P A Q L L P S T K T F A F Q T Q I R R G R F S V V R Q C R E K A S G R  Majority
                         570                 580                 590                 600
561   S - Q G R S A Q P L L P S T K T F A F Q T Q I R R G R F S V V R Q C W E K A S G R  H19G5-F1.pep
237   S S R G R P A Q L L P S T K T F A F Q T Q I R R G R F S V V R Q C R E K A S G R  R19G5-S.pep
237   S S R G R P A Q L L P S T K T F A F Q M Q I R R G R F S V V R Q C R E K A S G R  M19G5-S.pep
```

FIG. 2E

```
      A L A A K I V P Y Q P E D K T A V L R E Y E A L K R L H H P H L A Q L H A A A Y L   Majority
                      610                 620                 630                 640
601   A L A A K I  H  P Y  H P  K D K T A V L R E Y E A L K  G L R  H P H L A Q L H A A A Y L   H19G5-F1.pep
277   A L A A K I V P Y Q P E D K T A V L R E Y E A L K R L H H P H L A Q L H A A A Y L   R19G5-S.pep
277   A L A A K I V P Y Q P E D K T  T  V L R E Y E A L K R L H H P H L A Q L H A A A Y L   M19G5-S.pep S P R H L V L I L E L C S G P E L L P S L A E R X S Y S E S D V K D Y L W Q M L   Majority
                      650                 660                 670                 680
641   S P R H L V L I L E L C S G P E L L P  C  L A E R  A S Y S E S  E  V K D Y L W Q M L   H19G5-F1.pep
317   S P R H L V L I L E L C S G P E L L P S L A E R D S Y S E S D V K D Y L W Q M L   R19G5-S.pep
317   S P R H L V L I L E L C S G P E L L P S L A E R E S Y S E S D V K D Y L W Q M L   M19G5-S.pep S A T Q Y L H A Q H I L H L D L R S E N M M V T E Y N L L K V I D L G N A Q S L   Majority
                      690                 700                 710                 720
681   S A T Q Y L H A Q H I L H  N Q  H I L H L D L R S E N M  I I T  E Y N L L K V  V  D L G N A Q S L   H19G5-F1.pep
357   S A T Q Y L H A Q H I L H L D L R S E N M M V T E Y N L L K V I D L G N A Q S L   R19G5-S.pep
357   S A T Q Y L H A Q H I L H L D L R S E N M M V T E Y N L L K V I D L G N A Q S L   M19G5-S.pep S Q E K V P P P E N F K D Y L E T M A P E L L E G Q G A V P Q T D I W A I G V T   Majority
                      730                 740                 750                 760
721   S Q E K V  L P S D K  F K D Y L E T M A P E L L E G Q G A V P Q T D I W A I G V T   H19G5-F1.pep
397   S Q E K V P P P E N F K D Y L E T M A P E L L E G Q G A V P Q T D I W A I G V T   R19G5-S.pep
397    D  Q E K V P  A  P E N F K D Y L E T M A P E L L E G Q G A V P Q T D I W A I G V T   M19G5-S.pep
```

FIG. 2F

```
      A F I M L S G E Y P V S S E G T R D L Q K G L R K G L I R L S R C Y A G L S G G  Majority
                        770                 780                 790            800
761   A F I M L S A E Y P V S S E G A R D L Q R G L R K G L R K G L V R L S R C Y A G L S G G  H19G5-F1.pep
437   A F I M L S G E Y P V S S E G A R D L Q K G L R K G L R K G L I Q L S R C Y A G L S G G  R19G5-S.pep
437   A F I M L S G E Y P E S S E G T R D L Q K G L R K G L R K G L I R L S R C Y A G L S G G  M19G5-S.pep A V A F L Q S S L C A Q P W G R P C A S T C L Q C G W L T E E G P T G S R P T P  Majority
                        810                 820                 830            840
801   A V A F L R S T L C A Q P W G R P C A S S C L Q C P W L T E E G P A C S R P A P  H19G5-F1.pep
477   A V A F L Q S S L C A Q P W G R P C A S T C L Q C G W L T E E G P T G S R P T P  R19G5-S.pep
477   A V A F L Q S S L C A Q R P W G R P C A S T C L Q C G W L T E E G P T G S R P T P  M19G5-S.pep V T F P T A R L R A F V R E R E K R R A L L Y K K H N L A Q V R  Majority
                        850                 860                 870
841   V T F P T A R L R V F V R N R E K R R A L L Y K R H N L A Q V R  H19G5-F1.pep
517   V T F P T A R L R A F V R E R E K R R A L L Y K K H N L A Q V R  R19G5-S.pep
517   V T F P T V R L R A F V R E R E K R R A L L Y K K H N L A Q V R  M19G5-S.pep
```

Decoration 'Decoration #1': Box residues that match the Consensus exactly

FIG. 6

| FIG. 6A |
|---------|
| FIG. 6B |

FIG. 6A

Sequence Comparison of 19G5, Trio, and MLCK Kinase Domains

```
                    1                                                      30
19G5 C-term KD    A F - - Q T Q I Q R G R F S V V - R Q C W E K A S G R A L
19G5 N-term KD    S F Y E V K E E I G R G V F G F V K R - V Q H K G N K I L C
Trio KD           S F Y S E V A E L G R G R F S V V K K - C D Q K G T K R A V
SM MLCK KD        - - Y D I E E R L G S G K F G Q V F R L V E K K T G K I W A 19G5 C-term KD    A A K I I P Y H P K D T A V L R E Y E A L K G L R H P H L
19G5 N-term KD    A A K F I P L R S R T R A Q A Y R E R D I L A A L S H P L V
Trio KD           A T K F V N K K L M K R D Q V T H E L G I L Q S L Q H P L L
SM MLCK KD        G K F F K A Y S A K E K E N I P A E I G I M N C L H H P K L 19G5 C-term KD    A Q L H A A Y L S P R H L V L I L E L C S G P E L L P C L A
19G5 N-term KD    T G L L D Q F E T R K T L I L L E L C S E E L L D R L Y
Trio KD           V G L L D T F E T P T S Y I L V L E M A D Q G R L L D C V V
SM MLCK KD        V Q C V D A F E E K A N I V M V L E I V S G G E L F E R I I 19G5 C-term KD    E R A - S Y S E S E V K D Y L W Q M L S A T Q Y L H N Q H I
19G5 N-term KD    R K G - V V T E A E V K V Y I Q Q L V E G L H Y L H S H G V
Trio KD           R W G - S L T E G K I R A H L G E V L E A V R Y L H N C R I
SM MLCK KD        D E D F E L T E R E C I K Y M R Q I S E G V E Y I H K Q G I
```

FIG. 6B

```
19G5 C-term KD    L H L D L R S E N M I T E - - - Y N L L K V V D L G N A Q
19G5 N-term KD    L H L D D I K P S N I L M V H P - A R E D I K I C D F G F A Q
Trio KD           A H L D L K P E N I L V D E S L A K P T I K L A D F G D A V
SM MLCK KD        V H L D L K P E N I M C V N K T G T R - I K L I D F G L A R 19G5 C-term KD    S L S Q E K V L P S D K F K D Y L E T M A P E L L E G Q G A
19G5 N-term KD    N I T P A E L Q - - F S Q Y G S P E F V S P E I Q N P V
Trio KD           Q L N T T Y Y H - - H Q L L G N P E F A A P E I L G N P V
SM MLCK KD        R L E N A G S L - - K V L F G T P E F V A P E V I N Y E P I 19G5 C-term KD    V P Q T D I W A I G V T A F I M L S A E Y P V S S E G A R D
19G5 N-term KD    E A S D I W A M G V I S Y I L L S L T C S P F A G E S D R A
Trio KD           S L T S D T W S V G V L T Y Y I L L S G V S P F L D D S V E E
SM MLCK KD        S Y A T D M W S I G V I C Y I L V S G L S P F M G D N D N E 19G5 C-term KD    - L Q R G L R K G L V R L S R C Y A G L S G G A V A F L R S
19G5 N-term KD    T L L N V L E G R V S W S S P M A A H L S E D A K D F I K A
Trio KD           T C L N I C R L D F S F P D D Y F K G V S Q K A K E F V C F
SM MLCK KD        T L A N V T S A T W D F D D E A F D E I S D D A K D F I S N 19G5 C-term KD    T L C A Q P W G R P C A S S C L Q C P W - L T
19G5 N-term KD    T L Q R A P Q A R P S A A Q C L S H P W F L K
Trio KD           L L Q E D P A K R P S A A L A L Q E Q W - L Q
SM MLCK KD        L L K K D M K N R L D C T Q C L Q H P W L
```

FIG. 7

Sequence Comparison of 19G5 and Trio GEF Domains

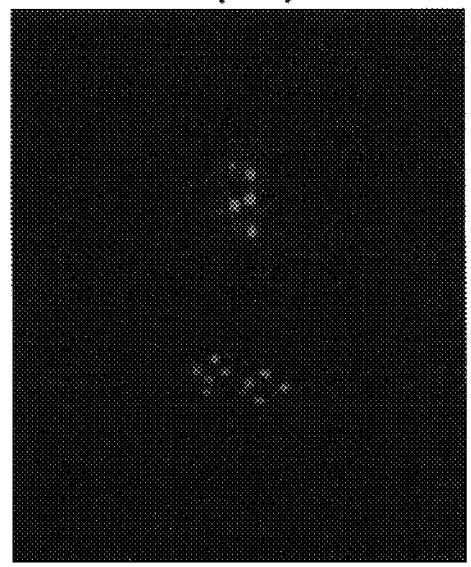
FIG. 8

SEQUENCE LISTING

<160> NUMBER OF SEQ ID NOS: 17

<210> SEQ ID NO 1
<211> LENGTH: 1351
<212> TYPE: PRT
<213> ORGANISM: Homo sapiens

<400> SEQUENCE: 1

```
Gly Val Gln Phe Ser Gln Tyr Gly Ser Pro Glu Phe Val Ser Pro Glu
 1               5                  10                  15

Ile Ile Gln Gln Asn Pro Val Ser Glu Ala Ser Asp Ile Trp Ala Met
            20                  25                  30

Gly Val Ile Ser Tyr Leu Ser Leu Thr Cys Ser Ser Pro Phe Ala Gly
        35                  40                  45

Glu Ser Asp Arg Ala Thr Leu Leu Asn Val Leu Glu Gly Arg Val Ser
    50                  55                  60

Trp Ser Ser Pro Met Ala Ala His Leu Ser Glu Asp Ala Lys Asp Phe
65                  70                  75                  80

Ile Lys Ala Thr Leu Gln Arg Ala Pro Gln Ala Arg Pro Ser Ala Ala
                85                  90                  95

Gln Cys Leu Ser His Pro Trp Phe Leu Lys Ser Met Pro Ala Glu Glu
            100                 105                 110

Ala His Phe Ile Asn Thr Lys Gln Leu Lys Phe Leu Leu Ala Arg Ser
        115                 120                 125

Arg Trp Gln Arg Ser Leu Met Ser Tyr Lys Ser Ile Leu Val Met Arg
    130                 135                 140

Ser Ile Pro Glu Leu Leu Arg Gly Pro Pro Asp Ser Pro Ser Leu Gly
145                 150                 155                 160

Val Ala Arg His Leu Cys Arg Asp Thr Gly Gly Ser Ser Ser Ser Ser
                165                 170                 175

Ser Ser Ser Asp Asn Glu Leu Ala Pro Phe Ala Arg Ala Lys Ser Leu
            180                 185                 190

Pro Pro Ser Pro Val Thr His Ser Pro Leu Leu His Pro Arg Gly Phe
        195                 200                 205

Leu Arg Pro Ser Ala Ser Leu Pro Glu Glu Ala Glu Ala Ser Glu Arg
    210                 215                 220

Ser Thr Glu Ala Pro Ala Pro Pro Ala Ser Pro Glu Gly Ala Gly Pro
225                 230                 235                 240

Pro Ala Ala Gln Gly Cys Val Pro Arg His Ser Val Ile Arg Ser Leu
                245                 250                 255

Phe Tyr His Gln Ala Gly Glu Ser Pro Glu His Gly Ala Leu Ala Pro
            260                 265                 270

Gly Ser Arg Arg His Pro Ala Arg Arg His Leu Leu Lys Gly Gly
        275                 280                 285

Tyr Ile Ala Gly Ala Leu Pro Gly Leu Arg Glu Pro Leu Met Glu His
    290                 295                 300

Arg Val Leu Glu Glu Glu Ala Ala Arg Glu Glu Gln Ala Thr Leu Leu
305                 310                 315                 320

Ala Lys Ala Pro Ser Phe Glu Thr Ala Leu Arg Leu Pro Ala Ser Gly
                325                 330                 335

Thr His Leu Ala Pro Gly His Ser His Ser Leu Glu His Asp Ser Pro
            340                 345                 350

Ser Thr Pro Arg Pro Ser Ser Glu Ala Cys Gly Glu Ala Gln Arg Leu
```

-continued

```
            355                 360                 365
Pro Ser Ala Pro Ser Gly Gly Ala Pro Ile Arg Asp Met Gly His Pro
        370                 375                 380
Gln Gly Ser Lys Gln Leu Pro Ser Thr Gly Gly His Pro Gly Thr Ala
385                 390                 395                 400
Gln Pro Glu Arg Pro Ser Pro Asp Ser Pro Trp Gly Gln Pro Ala Pro
                405                 410                 415
Phe Cys His Pro Lys Gln Gly Ser Ala Pro Gln Glu Gly Cys Ser Pro
                420                 425                 430
His Pro Ala Val Ala Pro Cys Pro Pro Gly Ser Phe Pro Pro Gly Ser
            435                 440                 445
Cys Lys Glu Ala Pro Leu Val Pro Ser Ser Pro Phe Leu Gly Gln Pro
        450                 455                 460
Gln Ala Pro Pro Ala Pro Ala Lys Ala Ser Pro Pro Leu Asp Ser Lys
465                 470                 475                 480
Met Gly Pro Gly Asp Ile Ser Leu Pro Gly Arg Pro Lys Pro Gly Pro
                485                 490                 495
Cys Ser Ser Pro Gly Ser Ala Ser Gln Ala Ser Ser Ser Gln Val Ser
                500                 505                 510
Ser Leu Arg Val Gly Ser Ser Gln Val Gly Thr Glu Pro Gly Pro Ser
            515                 520                 525
Leu Asp Ala Glu Gly Trp Thr Gln Glu Ala Glu Asp Leu Ser Asp Ser
        530                 535                 540
Thr Pro Thr Leu Gln Arg Pro Gln Glu Gln Ala Thr Met Arg Lys Phe
545                 550                 555                 560
Ser Leu Gly Gly Arg Gly Gly Tyr Ala Gly Val Ala Gly Tyr Gly Thr
                565                 570                 575
Phe Ala Phe Gly Gly Asp Ala Gly Gly Met Leu Gly Gln Gly Pro Met
                580                 585                 590
Trp Ala Arg Ile Ala Trp Ala Val Ser Gln Ser Glu Glu Glu Glu Gln
            595                 600                 605
Glu Glu Ala Arg Ala Glu Ser Gln Ser Glu Glu Gln Gln Glu Ala Arg
        610                 615                 620
Ala Glu Ser Pro Leu Pro Gln Val Ser Ala Arg Pro Val Pro Glu Val
625                 630                 635                 640
Gly Arg Ala Pro Thr Arg Ser Ser Pro Glu Pro Thr Pro Trp Glu Asp
                645                 650                 655
Ile Gly Gln Val Ser Leu Val Gln Ile Arg Asp Leu Ser Gly Asp Ala
                660                 665                 670
Glu Ala Ala Asp Thr Ile Ser Leu Asp Ile Ser Glu Val Asp Pro Ala
            675                 680                 685
Tyr Leu Asn Leu Ser Asp Leu Tyr Asp Ile Lys Tyr Leu Pro Phe Glu
        690                 695                 700
Phe Met Ile Phe Arg Lys Val Pro Lys Ser Ala Gln Pro Glu Pro Pro
705                 710                 715                 720
Ser Pro Met Ala Glu Glu Leu Ala Glu Phe Pro Glu Pro Thr Trp
                725                 730                 735
Pro Trp Pro Gly Glu Leu Gly Pro His Ala Gly Leu Glu Ile Thr Glu
                740                 745                 750
Glu Ser Glu Asp Val Asp Ala Leu Leu Ala Glu Ala Ala Val Gly Arg
            755                 760                 765
Lys Arg Lys Trp Ser Ser Pro Ser Arg Ser Leu Phe His Phe Pro Gly
        770                 775                 780
```

-continued

```
Arg His Leu Pro Leu Asp Glu Pro Ala Glu Leu Gly Leu Arg Glu Arg
785                 790                 795                 800

Val Lys Ala Ser Val Glu His Ile Ser Arg Ile Leu Lys Gly Arg Pro
                805                 810                 815

Glu Gly Leu Glu Lys Glu Gly Pro Pro Arg Lys Lys Pro Gly Leu Ala
            820                 825                 830

Ser Phe Arg Leu Ser Gly Leu Lys Ser Trp Asp Arg Ala Pro Thr Phe
        835                 840                 845

Leu Arg Glu Leu Ser Asp Glu Thr Val Val Leu Gly Gln Ser Val Thr
    850                 855                 860

Leu Ala Cys Gln Val Ser Ala Gln Pro Ala Ala Gln Ala Thr Trp Ser
865                 870                 875                 880

Lys Asp Gly Ala Pro Leu Glu Ser Ser Ser Arg Val Leu Ile Ser Ala
                885                 890                 895

Thr Leu Lys Asn Phe Gln Leu Leu Thr Ile Leu Val Val Val Ala Glu
            900                 905                 910

Asp Leu Gly Val Tyr Thr Cys Ser Val Ser Asn Ala Leu Gly Thr Val
        915                 920                 925

Thr Thr Thr Gly Val Leu Arg Lys Ala Glu Arg Pro Ser Ser Ser Pro
    930                 935                 940

Cys Pro Asp Ile Gly Glu Val Tyr Ala Asp Gly Val Leu Leu Val Trp
945                 950                 955                 960

Lys Pro Val Glu Ser Tyr Gly Pro Val Thr Tyr Ile Val Gln Cys Ser
                965                 970                 975

Leu Glu Gly Gly Ser Trp Thr Thr Leu Ala Ser Asp Ile Phe Asp Cys
            980                 985                 990

Cys Tyr Leu Thr Ser Lys Leu Ser Arg Gly Gly Thr Tyr Thr Phe Arg
        995                 1000                1005

Thr Ala Cys Val Ser Lys Ala Gly Met Gly Pro Tyr Ser Ser Pro Ser
    1010                1015                1020

Glu Gln Val Leu Leu Gly Gly Pro Ser His Leu Ala Ser Glu Glu Glu
1025                1030                1035                1040

Ser Gln Gly Arg Ser Ala Gln Pro Leu Pro Ser Thr Lys Thr Phe Ala
                1045                1050                1055

Phe Gln Thr Gln Ile Gln Arg Gly Arg Phe Ser Val Val Arg Gln Cys
            1060                1065                1070

Trp Glu Lys Ala Ser Gly Arg Ala Leu Ala Ala Lys Ile Ile Pro Tyr
        1075                1080                1085

His Pro Lys Asp Lys Thr Ala Val Leu Arg Glu Tyr Glu Ala Leu Lys
    1090                1095                1100

Gly Leu Arg His Pro His Leu Ala Gln Leu His Ala Ala Tyr Leu Ser
1105                1110                1115                1120

Pro Arg His Leu Val Leu Ile Leu Glu Leu Cys Ser Gly Pro Glu Leu
                1125                1130                1135

Leu Pro Cys Leu Ala Glu Arg Ala Ser Tyr Ser Glu Ser Glu Val Lys
            1140                1145                1150

Asp Tyr Leu Trp Gln Met Leu Ser Ala Thr Gln Tyr Leu His Asn Gln
        1155                1160                1165

His Ile Leu His Leu Asp Leu Arg Ser Glu Asn Met Ile Ile Thr Glu
    1170                1175                1180

Tyr Asn Leu Leu Lys Val Val Asp Leu Gly Asn Ala Gln Ser Leu Ser
1185                1190                1195                1200
```

```
Gln Glu Lys Val Leu Pro Ser Asp Lys Phe Lys Asp Tyr Leu Glu Thr
            1205                1210                1215
Met Ala Pro Glu Leu Leu Glu Gly Gln Gly Ala Val Pro Gln Thr Asp
        1220                1225                1230
Ile Trp Ala Ile Gly Val Thr Ala Phe Ile Met Leu Ser Ala Glu Tyr
    1235                1240                1245
Pro Val Ser Ser Glu Gly Ala Arg Asp Leu Gln Arg Gly Leu Arg Lys
1250                1255                1260
Gly Leu Val Arg Leu Ser Arg Cys Tyr Ala Gly Leu Ser Gly Gly Ala
1265                1270                1275                1280
Val Ala Phe Leu Arg Ser Thr Leu Cys Ala Gln Pro Trp Gly Arg Pro
            1285                1290                1295
Cys Ala Ser Ser Cys Leu Gln Cys Pro Trp Leu Thr Glu Glu Gly Pro
        1300                1305                1310
Ala Cys Ser Arg Pro Ala Pro Val Thr Phe Pro Thr Ala Arg Leu Arg
    1315                1320                1325
Val Phe Val Arg Asn Arg Glu Lys Arg Arg Ala Leu Leu Tyr Lys Arg
1330                1335                1340
His Asn Leu Ala Gln Val Arg
1345                1350

<210> SEQ ID NO 2
<211> LENGTH: 4175
<212> TYPE: DNA
<213> ORGANISM: Homo sapiens
<220> FEATURE:
<221> NAME/KEY: CDS
<222> LOCATION: (1)...(4053)

<400> SEQUENCE: 2
ggagtgcagt tcagccagta cggctcccct gagttcgtct ccccgagat catccagcag        60
aaccctgtga gcgaagcctc cgacatttgg gccatgggtg tcatctccta cctcagcctg       120
acctgctcat ccccatttgc cggcgagagt gaccgtgcca ccctcctgaa cgtcctggag       180
gggcgcgtgt catggagcag ccccatggct gcccacctca gcgaagacgc caaagacttc       240
atcaaggcta cgctgcagag agcccctcag gcccggccta gtgcggccca gtgcctctcc       300
cacccctggt tcctgaaatc catgcctgcg gaggaggccc acttcatcaa caccaagcag       360
ctcaagttcc tcctggcccg aagtcgctgg cagcgttccc tgatgagcta caagtccatc       420
ctggtgatgc gctccatccc tgagctgctg cggggcccac ccgacagccc ctccctcggc       480
gtagcccggc acctctgcag ggacactggt ggctcctcca gttcctcctc ctcctctgac       540
aacgagctcg ccccatttgc ccgggctaag tcactgccac cctccccggt gacacactca       600
ccactgctgc accccggggg cttcctgcgg ccctcggcca gcctgcctga ggaagccgag       660
gccagtgagc gctccaccga ggccccagct ccgcctgcat ctcccgaggg tgccgggcca       720
ccggccgccc agggctgcgt gccccggcac agcgtcatcc gcagcctgtt ctaccaccag       780
gcgggtgaga gccctgagca cggggccctg ccccgggga caggcggca cccgccccgg        840
cggcggcacc tgctgaaggg cgggtacatt gcggggcgc tgccaggcct gcgcgagcca        900
ctgatggagc accgcgtgct ggaggaggag gccgccaggg aggagcaggc caccctcctg       960
gccaaagccc cctcattcga gactgccctc cggctgcctg cctctggcac ccacttggcc      1020
cctggccaca gccactccct ggaacatgac tctccgagca ccccccgccc ctcctcggag      1080
gcctgcggtg aggcacagcg actgccttca gccccctccg gggggccccc tatcagggac      1140
```

```
atgggcacc ctcagggctc aagcagctt ccatccactg gtggccaccc aggcactgct    1200
cagccagaga ggccatcccc ggacagccct tgggggcagc cagccccttt ctgccacccc    1260
aagcagggtt ctgcccccca ggagggctgc agccccacc cagcagttgc cccatgccct    1320
cctggctcct tccctccagg atcttgcaaa gaggcccct tagtaccctc aagcccttc    1380
ttgggacagc cccaggcacc ccctgcccct gccaaagcaa gcccccatt ggactctaag    1440
atggggcctg gagacatctc tcttcctggg aggccaaaac ccggcccctg cagttcccca    1500
gggtcagcct cccaggcgag ctcttcccaa gtgagctccc tcagggtggg ctcctcccag    1560
gtgggcacag agcctggccc ctccctggat gcggagggct ggacccagga ggctgaggat    1620
ctgtccgact ccacacccac cttgcagcgg cctcaggaac aggcgaccat gcgcaagttc    1680
tccctgggtg gtcgcggggg ctacgcaggc gtggctggct atggcacctt tgcctttggt    1740
ggagatgcag ggggcatgct ggggcagggg cccatgtggg ccaggatagc ctgggctgtg    1800
tcccagtcag aggaggagga gcaggaggag gccaggggctg agtcccagtc ggaggagcag    1860
caggaggcca gggctgagag cccactgccc caggtcagtg caaggcctgt gcctgaggtc    1920
ggcagggctc ccaccaggag ctctccagag cccaccccat gggaggacat cgggcaggtc    1980
tccctggtgc agatccggga cctgtcaggt gatgcggagg cggccgacac aatatccctg    2040
gacatttccg aggtggaccc cgcctacctc aacctctcag acctgtacga tatcaagtac    2100
ctcccattcg agtttatgat cttcaggaaa gtccccaagt ccgctcagcc agagccgccc    2160
tccccccatgg ctgaggagga gctggccgag ttccggagc ccacgtggcc ctggccaggt    2220
gaactgggcc cccacgcagg cctggagatc acagaggagt cagaggatgt ggacgcgctg    2280
ctggcagagg ctgccgtggg caggaagcgc aagtggtcct cgccgtcacg cagcctcttc    2340
cacttccctg ggaggcacct gccgctggat gagcctgcag agctggggct gcgtgagaga    2400
gtgaaggcct ccgtggagca catctcccgg atcctgaagg gcaggccgga aggtctggag    2460
aaggagggggc cccccaggaa gaagccaggc cttgcttcct tccggctctc aggtctgaag    2520
agctgggacc gagcgccgac attcctaagg gagctctcag atgagactgt ggtcctgggc    2580
cagtcagtga cactggcctg ccaggtgtca gcccagccag ctgcccaggc cacctggagc    2640
aaagacggag cccccctgga gagcagcagc cgtgtcctca tctctgccac cctcaagaac    2700
ttccagcttc tgaccatcct ggtggtggtg gctgaggacc tgggtgtgta cacctgcagc    2760
gtgagcaatg cgctggggac agtgaccacc acgggcgtcc tccggaaggc agagcgcccc    2820
tcatcttcgc catgcccgga tatcggggag gtgtacgcgg atggggtgct gctggtctgg    2880
aagcccgtgg aatcctacgg ccctgtgacc tacattgtgc agtgcagcct agaaggcggc    2940
agctggacca cactggcctc cgacatcttt gactgctgct acctgaccag caagctctcc    3000
cggggtggca cctacacctt ccgcacggca tgtgtcagca aggcaggaat gggtccctac    3060
agcagcccct cggagcaagt cctcctggga gggcccagcc acctggcctc tgaggaggag    3120
agccaggggc ggtcagccca accctgccc agcacaaaga ccttcgcatt ccagacacag    3180
atccagaggg gccgcttcag cgtggtgcgg caatgctggg agaaggccag cgggcgggcg    3240
ctggccgcca agatcatccc ctaccacccc aaggacaaga cagcagtgct gcgcgaatac    3300
gaggccctca agggctgcg ccaccgcac ctggcccagc tgcacgcagc ctacctcagc    3360
ccccggcacc tggtgctcat cttggagctg tgctctgggc ccgagctgct ccctgcctg    3420
gccgagaggg cctcctactc agaatccgag gtgaaggact acctgtggca gatgttgagt    3480
gccacccagt acctgcacaa ccagcacatc ctgcacctgg acctgaggtc cgagaacatg    3540
```

-continued

| | |
|---|---|
| atcatcaccg aatacaacct gctcaaggtc gtggacctgg gcaatgcaca gagcctcagc | 3600 |
| caggagaagg tgctgccctc agacaagttc aaggactacc tagagaccat ggctccagag | 3660 |
| ctcctggagg gccaggggc tgttccacag acagacatct gggccatcgg tgtgacagcc | 3720 |
| ttcatcatgc tgagcgccga gtacccggtg agcagcgagg gtgcacgcga cctgcagaga | 3780 |
| ggactgcgca aggggctggt ccggctgagc cgctgctacg cggggctgtc cgggggcgcc | 3840 |
| gtggccttcc tgcgcagcac tctgtgcgcc cagccctggg gccggccctg cgcgtccagc | 3900 |
| tgcctgcagt gcccgtggct aacagaggag gcccggcct gttcgcggcc cgcgcccgtg | 3960 |
| accttcccta ccgcgcggct gcgcgtcttc gtgcgcaatc gcgagaagag acgcgcgctg | 4020 |
| ctgtacaaga ggcacaacct ggcccaggtg cgctgagggt cgccccggcc acacccttgg | 4080 |
| tctcccgct gggggtcgct gcagacgcgc caataaaaac gcacagccgg gcgagaaaaa | 4140 |
| aaaaaaaaaa aaaaaaaaaa aaaaaaaaaa aaaaa | 4175 |

<210> SEQ ID NO 3
<211> LENGTH: 5007
<212> TYPE: DNA
<213> ORGANISM: Homo sapiens
<220> FEATURE:
<221> NAME/KEY: CDS
<222> LOCATION: (97)...(4926)

<400> SEQUENCE: 3

| | |
|---|---|
| ctgctctggg acgtccacag ccacgtggtc agagagacca cacagaggac ctacacatac | 60 |
| caggccatcg acacgcacac cgcacggccc ccatccatgc aggtaaccat cgaggatgtg | 120 |
| caggcacaga caggcggaac ggcccaattc gaggctatca ttgagggcga cccacagccc | 180 |
| tcggtgacct ggtacaagga cagcgtccag ctggtggaca gcacccggct tagccagcag | 240 |
| caagaaggca ccacatactc cctggtgctg aggcatgtgg cctcgaagga tgccggcgtt | 300 |
| tacacctgcc tggcccaaaa cactggtggc caggtgctct gcaaggcaga gctgctggtg | 360 |
| cttgggggg acaatgagcc ggactcgag aagcaaagcc accggaggaa gctgcactcc | 420 |
| ttctatgagg tcaaggagga gattggaagg ggcgtgtttg gcttcgtaaa aagagtgcag | 480 |
| cacaaaggaa acaagatctt gtgcgctgcc aagttcatcc ccctacggag cagaactcgg | 540 |
| gcccaggcat acagggagcg agacatcctg gccgcgctga gccacccgct ggtcacgggg | 600 |
| ctgctggacc agtttgagac ccgcaagacc ctcatcctca tcctggagct gtgctcatcc | 660 |
| gaggagctgc tggaccgcct gtacaggaag ggcgtggtga cggaggccga ggtcaaggtc | 720 |
| tacatccagc agctggtgga ggggctgcac tacctgcaca gccatggcgt tctccacctg | 780 |
| gacataaagc cctctaacat cctgatggtg catcctgccc gggaagacat taaaatctgc | 840 |
| gactttggct tgcccagaa catcaccca gcagagctgc agttcagcca gtacggctcc | 900 |
| cctgagttcg tctcccccga gatcatccag cagaaccctg tgagcgaagc ctccgacatt | 960 |
| tgggccatgg gtgtcatctc ctacctcagc ctgacctgct catcccatt gccggcgag | 1020 |
| agtgaccgtg ccaccctcct gaacgtcctg gaggggcgcg tgtcatggag cagccccatg | 1080 |
| gctgcccacc tcagcgaaga cgccaaagac ttcatcaagg ctacgctgca gagagcccct | 1140 |
| caggcccggc ctagtgcggc ccagtgcctc tcccaccct ggttcctgaa atccatgcct | 1200 |
| gcggaggagg cccacttcat caacaccaag cagctcaagt tcctcctggc ccgaagtcgc | 1260 |
| tggcagcgtt ccctgatgag ctacaagtcc atcctggtga tgcgctccat ccctgagctg | 1320 |
| ctgcggggcc cacccgacag cccctccctc ggcgtagccc ggcacctctg cagggacact | 1380 |

-continued

```
ggtggctcct ccagttcctc ctcctcctct gacaacgagc tcgccccatt tgcccgggct   1440
aagtcactgc caccctcccc ggtgacacac tcaccactgc tgcaccccg gggcttcctg    1500 cggccctcgg ccagcctgcc tgaggaagcc gaggccagtg agcgctccac cgaggcccca   1560
gctccgcctg catctcccga gggtgccggg ccaccggccg cccagggctg cgtgccccgg   1620
cacagcgtca tccgcagcct gttctaccac caggcgggtg agagccctga gcacggggcc   1680
ctggccccgg ggagcaggcg gcacccggcc cggcggcggc acctgctgaa gggcgggtac   1740
attgcggggg cgctgccagg cctgcgcgag ccactgatgg agcaccgcgt gctggaggag   1800
gaggccgcca gggaggagca ggccaccctc ctggccaaag cccctcatt cgagactgcc    1860 ctccggctgc ctgcctctgg cacccacttg gcccctggcc acagccactc cctggaacat   1920
gactctccga gcaccccccg cccctcctcg gaggcctgcg gtgaggcaca gcgactgcct   1980
tcagccccct ccggggggc ccctatcagg gacatgggc accctcaggg ctccaagcag     2040
cttccatcca ctggtggcca cccaggcact gctcagccag agaggccatc cccggacagc   2100
ccttgggggc agccagcccc tttctgccac cccaagcagg gttctgcccc caggagggc    2160 tgcagccccc acccagcagt tgccccatgc cctcctggct ccttccctcc aggatcttgc   2220
aaagaggccc ccttagtacc ctcaagcccc ttcttgggac agccccaggc accccctgcc   2280
cctgccaaag caagccccc attggactct aagatgggc ctggagacat ctctcttcct     2340
gggaggccaa aacccggccc ctgcagttcc ccagggtcag cctcccaggc gagctcttcc   2400
caagtgagct ccctcagggt gggctcctcc caggtgggca cagagcctgg cccctccctg   2460
gatgcggagg gctggaccca ggaggctgag gatctgtccg actccacacc caccttgcag   2520
cggcctcagg aacaggcgac catgcgcaag ttctccctgg gtggtcgcgg gggctacgca   2580
ggcgtggctg gctatggcac ctttgccttt ggtggagatg caggggcat gctggggcag    2640 gggcccatgt gggccaggat agcctgggct gtgtcccagt cagaggagga ggagcaggag   2700
gaggccaggg ctgagtccca gtcggaggag cagcaggagg ccaggctga gagcccactg     2760 ccccaggtca gtgcaaggcc tgtgcctgag gtcggcaggg ctcccaccag gagctctcca   2820
gagcccaccc catgggagga catcgggcag gtctccctgg tgcagatccg ggacctgtca   2880
ggtgatgcgg aggcggccga cacaatatcc ctggacattt ccgaggtgga ccccgcctac   2940
ctcaacctct cagacctgta cgatatcaag tacctcccat tcgagtttat gatcttcagg   3000
aaagtcccca agtccgctca gccagagccg ccctccccca tggctgagga ggagctggcc   3060
gagttcccgg agcccacgtg gccctggcca ggtgaactgg gccccacgc aggcctggag    3120 atcacagagg agtcagagga tgtggacgcg ctgctggcag aggctgccgt gggcaggaag   3180
cgcaagtggt cctcgccgtc acgcagcctc ttccacttcc ctgggaggca cctgccgctg   3240
gatgagcctg cagagctggg gctgcgtgag agagtgaagg cctccgtgga gcacatctcc   3300
cggatcctga agggcaggcc ggaaggtctg gagaaggagg ggcccccag gaagaagcca    3360 ggccttgctt ccttccggct ctcaggtctg aagagctggg accgagcgcc gacattccta   3420
agggagctct cagatgagac tgtggtcctg ggccagtcag tgacactggc ctgccaggtg   3480
tcagcccagc cagctgccca ggccacctgg agcaaagacg gagccccct ggagagcagc    3540 agccgtgtcc tcatctctgc caccctcaag aacttccagc ttctgaccat cctggtggtg   3600
gtggctgagg acctgggtgt gtacacctgc agcgtgagca atgcgctggg gacagtgacc   3660
accacgggcg tcctccggaa ggcagagcgc ccctcatctt cgccatgccc ggatatcggg   3720
```

-continued

```
gaggtgtacg cggatggggt gctgctggtc tggaagcccg tggaatccta cggccctgtg    3780
acctacattg tgcagtgcag cctagaaggc ggcagctgga ccacactggc ctccgacatc    3840
tttgactgct gctacctgac cagcaagctc tcccggggtg caccctacac cttccgcacg    3900
gcatgtgtca gcaaggcagg aatgggtccc tacagcagcc cctcggagca agtcctcctg    3960
ggagcgccca gccacctggc ctctgaggag gagagccagg gcggtcagc ccaacccctg    4020 cccagcacaa agaccttcgc attccagaca cagatccaga ggggccgctt cagcgtggtg    4080
cggcaatgct gggagaaggc cagcgggcgg gcgctggccg ccaagatcat ccctaccac    4140 cccaaggaca agacagcagt gctgcgcgaa tacgaggccc tcaagggcct gcgccacccg    4200
cacctggccc agctgcacgc agcctacctc agccccggc acctggtgct catcttggag    4260
ctgtgctctg gcccgagct gctccctgc ctggccgaga gggcctccta ctcagaatcc    4320
gaggtgaagg actacctgtg gcagatgttg agtgccaccc agtacctgca caaccagcac    4380
atcctgcacc tggacctgag gtccgagaac atgatcatca ccgaatacaa cctgctcaag    4440
gtcgtggacc tgggcaatgc acagagcctc agccaggaga aggtgctgcc ctcagacaag    4500
ttcaaggact acctagagac catggctcca gagctcctgg agggccaggg ggctgttcca    4560
cagacagaca tctgggccat cggtgtgaca gccttcatca tgctgagcgc cgagtacccg    4620
gtgagcagcg agggtgcacg cgacctgcag agaggactgc gcaagggggct ggtccggctg    4680 agccgctgct acgcggggct gtccggggggc gccgtggcct tcctgcgcag cactctgtgc    4740
gcccagccct gggggccggcc ctgcgcgtcc agctgcctgc agtgcccgtg ctaacagag    4800 gagggcccgg cctgttcgcg gcccgcgccc gtgaccttcc ctaccgcgcg ctgcgcgtc    4860 ttcgtgcgca atcgcgagaa gagacgcgcg ctgctgtaca agaggcacaa cctggcccag    4920
gtgcgctgag ggtcgccccg gccacaccct tggtctcccc gctggggtc gctgcagacg    4980 cgccaataaa aacgcacagc cgggcga                                       5007
```

<210> SEQ ID NO 4
<211> LENGTH: 1610
<212> TYPE: PRT
<213> ORGANISM: Homo sapiens

<400> SEQUENCE: 4

```
Met Gln Val Thr Ile Glu Asp Val Gln Ala Gln Thr Gly Gly Thr Ala
 1               5                  10                  15

Gln Phe Glu Ala Ile Glu Gly Asp Pro Gln Pro Ser Val Thr Trp
            20                  25                  30

Tyr Lys Asp Ser Val Gln Leu Val Asp Ser Thr Arg Leu Ser Gln Gln
        35                  40                  45

Gln Glu Gly Thr Thr Tyr Ser Leu Val Leu Arg His Val Ala Ser Lys
    50                  55                  60

Asp Ala Gly Val Tyr Thr Cys Leu Ala Gln Asn Thr Gly Gly Gln Val
65                  70                  75                  80

Leu Cys Lys Ala Glu Leu Leu Val Leu Gly Gly Asp Asn Glu Pro Asp
                85                  90                  95

Ser Glu Lys Gln Ser His Arg Arg Lys Leu His Ser Phe Tyr Glu Val
            100                 105                 110

Lys Glu Glu Ile Gly Arg Gly Val Phe Gly Phe Val Lys Arg Val Gln
        115                 120                 125

His Lys Gly Asn Lys Ile Leu Cys Ala Ala Lys Phe Ile Pro Leu Arg
    130                 135                 140
```

-continued

```
Ser Arg Thr Arg Ala Gln Ala Tyr Arg Glu Arg Asp Ile Leu Ala Ala
145                 150                 155                 160

Leu Ser His Pro Leu Val Thr Gly Leu Leu Asp Gln Phe Glu Thr Arg
                165                 170                 175

Lys Thr Leu Ile Leu Ile Leu Glu Leu Cys Ser Ser Glu Glu Leu Leu
            180                 185                 190

Asp Arg Leu Tyr Arg Lys Gly Val Val Thr Glu Ala Glu Val Lys Val
        195                 200                 205

Tyr Ile Gln Gln Leu Val Glu Gly Leu His Tyr Leu His Ser His Gly
210                 215                 220

Val Leu His Leu Asp Ile Lys Pro Ser Asn Ile Leu Met Val His Pro
225                 230                 235                 240

Ala Arg Glu Asp Ile Lys Ile Cys Asp Phe Gly Phe Ala Gln Asn Ile
                245                 250                 255

Thr Pro Ala Glu Leu Gln Phe Ser Gln Tyr Gly Ser Pro Glu Phe Val
            260                 265                 270

Ser Pro Glu Ile Ile Gln Gln Asn Pro Val Ser Glu Ala Ser Asp Ile
        275                 280                 285

Trp Ala Met Gly Val Ile Ser Tyr Leu Ser Leu Thr Cys Ser Ser Pro
290                 295                 300

Phe Ala Gly Glu Ser Asp Arg Ala Thr Leu Leu Asn Val Leu Glu Gly
305                 310                 315                 320

Arg Val Ser Trp Ser Ser Pro Met Ala Ala His Leu Ser Glu Asp Ala
                325                 330                 335

Lys Asp Phe Ile Lys Ala Thr Leu Gln Arg Ala Pro Gln Ala Arg Pro
            340                 345                 350

Ser Ala Ala Gln Cys Leu Ser His Pro Trp Phe Leu Lys Ser Met Pro
        355                 360                 365

Ala Glu Glu Ala His Phe Ile Asn Thr Lys Gln Leu Lys Phe Leu Leu
370                 375                 380

Ala Arg Ser Arg Trp Gln Arg Ser Leu Met Ser Tyr Lys Ser Ile Leu
385                 390                 395                 400

Val Met Arg Ser Ile Pro Glu Leu Leu Arg Gly Pro Pro Asp Ser Pro
                405                 410                 415

Ser Leu Gly Val Ala Arg His Leu Cys Arg Asp Thr Gly Gly Ser Ser
            420                 425                 430

Ser Ser Ser Ser Ser Ser Asp Asn Glu Leu Ala Pro Phe Ala Arg Ala
        435                 440                 445

Lys Ser Leu Pro Pro Ser Pro Val Thr His Ser Pro Leu Leu His Pro
450                 455                 460

Arg Gly Phe Leu Arg Pro Ser Ala Ser Leu Pro Glu Glu Ala Glu Ala
465                 470                 475                 480

Ser Glu Arg Ser Thr Glu Ala Pro Ala Pro Ala Ser Pro Glu Gly
                485                 490                 495

Ala Gly Pro Pro Ala Ala Gln Gly Cys Val Pro Arg His Ser Val Ile
            500                 505                 510

Arg Ser Leu Phe Tyr His Gln Ala Gly Glu Ser Pro Glu His Gly Ala
        515                 520                 525

Leu Ala Pro Gly Ser Arg Arg His Pro Ala Arg Arg His Leu Leu
530                 535                 540

Lys Gly Gly Tyr Ile Ala Gly Ala Leu Pro Gly Leu Arg Glu Pro Leu
545                 550                 555                 560

Met Glu His Arg Val Leu Glu Glu Glu Ala Ala Arg Glu Glu Gln Ala
```

-continued

```
                565                 570                 575
Thr Leu Leu Ala Lys Ala Pro Ser Phe Glu Thr Ala Leu Arg Leu Pro
            580                 585                 590
Ala Ser Gly Thr His Leu Ala Pro Gly His Ser His Ser Leu Glu His
        595                 600                 605
Asp Ser Pro Ser Thr Pro Arg Pro Ser Ser Glu Ala Cys Gly Glu Ala
    610                 615                 620
Gln Arg Leu Pro Ser Ala Pro Ser Gly Gly Ala Pro Ile Arg Asp Met
625                 630                 635                 640
Gly His Pro Gln Gly Ser Lys Gln Leu Pro Ser Thr Gly Gly His Pro
                645                 650                 655
Gly Thr Ala Gln Pro Glu Arg Pro Ser Pro Asp Ser Pro Trp Gly Gln
            660                 665                 670
Pro Ala Pro Phe Cys His Pro Lys Gln Gly Ser Ala Pro Gln Glu Gly
        675                 680                 685
Cys Ser Pro His Pro Ala Val Ala Pro Cys Pro Pro Gly Ser Phe Pro
    690                 695                 700
Pro Gly Ser Cys Lys Glu Ala Pro Leu Val Pro Ser Ser Pro Phe Leu
705                 710                 715                 720
Gly Gln Pro Gln Ala Pro Pro Ala Pro Ala Lys Ala Ser Pro Pro Leu
                725                 730                 735
Asp Ser Lys Met Gly Pro Gly Asp Ile Ser Leu Pro Gly Arg Pro Lys
            740                 745                 750
Pro Gly Pro Cys Ser Ser Pro Gly Ser Ala Ser Gln Ala Ser Ser Ser
        755                 760                 765
Gln Val Ser Ser Leu Arg Val Gly Ser Ser Gln Val Gly Thr Glu Pro
    770                 775                 780
Gly Pro Ser Leu Asp Ala Glu Gly Trp Thr Gln Glu Ala Glu Asp Leu
785                 790                 795                 800
Ser Asp Ser Thr Pro Thr Leu Gln Arg Pro Gln Glu Gln Ala Thr Met
                805                 810                 815
Arg Lys Phe Ser Leu Gly Gly Arg Gly Gly Tyr Ala Gly Val Ala Gly
            820                 825                 830
Tyr Gly Thr Phe Ala Phe Gly Gly Asp Ala Gly Gly Met Leu Gly Gln
        835                 840                 845
Gly Pro Met Trp Ala Arg Ile Ala Trp Ala Val Ser Gln Ser Glu Glu
    850                 855                 860
Glu Glu Gln Glu Glu Ala Arg Ala Glu Ser Gln Ser Glu Glu Gln Gln
865                 870                 875                 880
Glu Ala Arg Ala Glu Ser Pro Leu Pro Gln Val Ser Ala Arg Pro Val
                885                 890                 895
Pro Glu Val Gly Arg Ala Pro Thr Arg Ser Ser Pro Glu Pro Thr Pro
            900                 905                 910
Trp Glu Asp Ile Gly Gln Val Ser Leu Val Gln Ile Arg Asp Leu Ser
        915                 920                 925
Gly Asp Ala Glu Ala Ala Asp Thr Ile Ser Leu Asp Ile Ser Glu Val
    930                 935                 940
Asp Pro Ala Tyr Leu Asn Leu Ser Asp Leu Tyr Asp Ile Lys Tyr Leu
945                 950                 955                 960
Pro Phe Glu Phe Met Ile Phe Arg Lys Val Pro Lys Ser Ala Gln Pro
                965                 970                 975
Glu Pro Pro Ser Pro Met Ala Glu Glu Leu Ala Glu Phe Pro Glu
            980                 985                 990
```

-continued

```
Pro Thr Trp Pro Trp Pro Gly Glu Leu Gly Pro His Ala Gly Leu Glu
        995                 1000                1005

Ile Thr Glu Glu Ser Glu Asp Val Asp Ala Leu Leu Ala Glu Ala Ala
    1010                1015                1020

Val Gly Arg Lys Arg Lys Trp Ser Ser Pro Ser Arg Ser Leu Phe His
1025                1030                1035                1040

Phe Pro Gly Arg His Leu Pro Leu Asp Glu Pro Ala Glu Leu Gly Leu
                1045                1050                1055

Arg Glu Arg Val Lys Ala Ser Val Glu His Ile Ser Arg Ile Leu Lys
                1060                1065                1070

Gly Arg Pro Glu Gly Leu Glu Lys Glu Gly Pro Pro Arg Lys Lys Pro
            1075                1080                1085

Gly Leu Ala Ser Phe Arg Leu Ser Gly Leu Lys Ser Trp Asp Arg Ala
            1090                1095                1100

Pro Thr Phe Leu Arg Glu Leu Ser Asp Glu Thr Val Val Leu Gly Gln
1105                1110                1115                1120

Ser Val Thr Leu Ala Cys Gln Val Ser Ala Gln Pro Ala Ala Gln Ala
                1125                1130                1135

Thr Trp Ser Lys Asp Gly Ala Pro Leu Glu Ser Ser Arg Val Leu
            1140                1145                1150

Ile Ser Ala Thr Leu Lys Asn Phe Gln Leu Leu Thr Ile Leu Val Val
            1155                1160                1165

Val Ala Glu Asp Leu Gly Val Tyr Thr Cys Ser Val Ser Asn Ala Leu
1170                1175                1180

Gly Thr Val Thr Thr Thr Gly Val Leu Arg Lys Ala Glu Arg Pro Ser
1185                1190                1195                1200

Ser Ser Pro Cys Pro Asp Ile Gly Glu Val Tyr Ala Asp Gly Val Leu
                1205                1210                1215

Leu Val Trp Lys Pro Val Glu Ser Tyr Gly Pro Val Thr Tyr Ile Val
                1220                1225                1230

Gln Cys Ser Leu Glu Gly Gly Ser Trp Thr Thr Leu Ala Ser Asp Ile
            1235                1240                1245

Phe Asp Cys Cys Tyr Leu Thr Ser Lys Leu Ser Arg Gly Gly Thr Tyr
1250                1255                1260

Thr Phe Arg Thr Ala Cys Val Ser Lys Ala Gly Met Gly Pro Tyr Ser
1265                1270                1275                1280

Ser Pro Ser Glu Gln Val Leu Leu Gly Ala Pro Ser His Leu Ala Ser
                1285                1290                1295

Glu Glu Glu Ser Gln Gly Arg Ser Ala Gln Pro Leu Pro Ser Thr Lys
                1300                1305                1310

Thr Phe Ala Phe Gln Thr Gln Ile Gln Arg Gly Arg Phe Ser Val Val
            1315                1320                1325

Arg Gln Cys Trp Glu Lys Ala Ser Gly Arg Ala Leu Ala Ala Lys Ile
            1330                1335                1340

Ile Pro Tyr His Pro Lys Asp Lys Thr Ala Val Leu Arg Glu Tyr Glu
1345                1350                1355                1360

Ala Leu Lys Gly Leu Arg His Pro His Leu Ala Gln Leu His Ala Ala
                1365                1370                1375

Tyr Leu Ser Pro Arg His Leu Val Leu Ile Leu Glu Leu Cys Ser Gly
            1380                1385                1390

Pro Glu Leu Leu Pro Cys Leu Ala Glu Arg Ala Ser Tyr Ser Glu Ser
            1395                1400                1405
```

-continued

Glu Val Lys Asp Tyr Leu Trp Gln Met Leu Ser Ala Thr Gln Tyr Leu
1410                1415                1420

His Asn Gln His Ile Leu His Leu Asp Leu Arg Ser Glu Asn Met Ile
1425                1430                1435                1440

Ile Thr Glu Tyr Asn Leu Leu Lys Val Val Asp Leu Gly Asn Ala Gln
            1445                1450                1455

Ser Leu Ser Gln Glu Lys Val Leu Pro Ser Asp Lys Phe Lys Asp Tyr
            1460                1465                1470

Leu Glu Thr Met Ala Pro Glu Leu Leu Glu Gly Gln Gly Ala Val Pro
        1475                1480                1485

Gln Thr Asp Ile Trp Ala Ile Gly Val Thr Ala Phe Ile Met Leu Ser
        1490                1495                1500

Ala Glu Tyr Pro Val Ser Ser Glu Gly Ala Arg Asp Leu Gln Arg Gly
1505                1510                1515                1520

Leu Arg Lys Gly Leu Val Arg Leu Ser Arg Cys Tyr Ala Gly Leu Ser
            1525                1530                1535

Gly Gly Ala Val Ala Phe Leu Arg Ser Thr Leu Cys Ala Gln Pro Trp
            1540                1545                1550

Gly Arg Pro Cys Ala Ser Ser Cys Leu Gln Cys Pro Trp Leu Thr Glu
            1555                1560                1565

Glu Gly Pro Ala Cys Ser Arg Pro Ala Pro Val Thr Phe Pro Thr Ala
        1570                1575                1580

Arg Leu Arg Val Phe Val Arg Asn Arg Glu Lys Arg Arg Ala Leu Leu
1585                1590                1595                1600

Tyr Lys Arg His Asn Leu Ala Gln Val Arg
            1605                1610

<210> SEQ ID NO 5
<211> LENGTH: 7928
<212> TYPE: DNA
<213> ORGANISM: Homo sapiens
<220> FEATURE:
<221> NAME/KEY: CDS
<222> LOCATION: (60)...(7847)

<400> SEQUENCE: 5

```
gaattcggcg cgccagatat cacacgtgcc aaggggctgg ctcactggtg ccgccccgaa      60
tgctggagag gttcaccccc aagaaagtga agaaaggctc cagcatcacc ttctctgtga     120
aggtagaagg acgcccggtg cccaccgtgc actggctcag ggaggaggct gagagaggcg     180
tgctgtggat tggccctgac acaccgggct acaccgtggc cagctctgcg cagcagcaca     240
gcctggtcct gctggacgtg ggccggcagc accagggcac ctacacatgc attgccagca     300
acgctgccgg ccaggccctc tgctccgcca gcctgcacgt ctcgggcctg cctaaggtgg     360
aggagcagga gaaagtgaag gaagcgctga tttccacttt cctgcagggg accacacaag     420
ccatctcagc acagggttg gaaactgcga gttttgctga ccttggtggg cagaggaaag     480
aagagcctct ggctgccaag gaggccctcg gccacctgtc cctcgctgag gtgggcacag     540
aggagttcct gcagaaactg acctcccaga tcactgagat ggtatcggcc aagatcacgc     600
aggccaagct gcaggtgcca ggaggtgaca gtgatgagga ctccaagaca ccatctgcat     660
cccccgcca tggccgatca cggccatcct ccagcatcca ggagtcttcc tcagagtcag     720
aggacggcga tgcccgaggc gagatctttg acatctacgt ggtcaccgct gactacctgc     780
ccctaggggc tgagcaggat gccatcacgc tgcgggaagg ccagtatgtg gaggtcctgg     840
atgcagccca cccactgcgc tggcttgtcc gcaccaagcc caccaagtcc agcccctcac     900
```

```
ggcagggctg ggtgtcacca gcctacctgg acaggaggct caagctgtca cctgagtggg    960
gggccgctga ggcccctgag ttccctgggg aggctgtgtc tgaagacgaa tacaaggcaa   1020
ggctgagctc tgtgatccag gagctgctga gttctgagca ggccttcgtg gaggagctgc   1080
agttcctgca gagccaccac ctgcagcacc tggagcgctg cccccacgtg cccatagccg   1140
tggccggcca gaaggcagtc atcttccgca atgtgcggga tcggccgc ttccacagca    1200
gcttcctgca ggagttgcag cagtgcgaca cggacgacga cgtggccatg tgcttcatca   1260
agaaccaggc ggccttttgag cagtacctgg agttcctggt ggggcgtgtg caggctgagt   1320
cggtggtcgt cagcacggcc atccaggagt tctacaagaa atacgcggag gaggccctgt   1380
tggcagggga cccctctcag cccccgccac cacctctgca gcactacctg gagcagccag   1440
tggagcgggt gcagcgctac caggccttgc tgaaggagtt gatccgcaac aaggcgcgga   1500
acagacagaa ctgcgcgctg ctggagcagg cctatgccgt ggtgtctgcc ctgccacagc   1560
gcgctgagaa caagctgcac gtgtccctca tggagaacta cccaggcacc ctggaggccc   1620
tgggcgagcc catccgccag ggccacttca tcgtgtggga gggtgcaccg ggggcccgca   1680
tgccctggaa gggccacaac cgtcacgtgt tcctcttccg caaccacctg gtaatctgca   1740
agccccggcg agactcccgc accgatacccg tcagctacgt gttccggaac atgatgaagc   1800
tgagcagcat cgacctgaac gaccaggtgg agggggatga ccgcgccttc gaggtgtggc   1860
aggagcggga ggactcggtg cgcaagtacc tgctgcaggc acggacagcc attatcaaga   1920
gctcgtgggt gaaggagatc tgtggcatcc agcagcgtct ggccctgcct gtgtggcggc   1980
ccccggactt tgaagaggag ctggccgact gcacagccga gctgggtgag acagtcaagc   2040
tggcctgccg cgtgacgggc acacccaagc ctgtcatcag ctggtacaaa gatgggaaag   2100
cagtgcaggt ggaccccac cacatcctca ttgaagaccc tgatggctcg tgtgcactca   2160
tcctggacag cctgaccggt gtggactctg gccagtacat gtgcttcgcg ccagcgccg    2220
ctggcaactg cagtaccctg ggcaagatcc tggtgcaagt ccaccacgg ttcgtgaaca   2280
aggtccgggc ctcaccctt gtggagggag aggacgccca gttcacctgc accatcgaag   2340
gcgccccgta cccgcagatc aggtggtaca aggacggggc cctgctgacc actggcaaca   2400
agttccagac actgagtgag cctcgcagcg gcctgctagt gctggtgatc cgggcggcca   2460
gcaaggagga cctggggctc tacgagtgtg agctggtgaa ccggctgggc tccgcgcggg   2520
ctagtgcgga gctgcgcatt cagagcccca tgctgcaggc caggagcag tgtcacaggg    2580
agcagctcgt ggctgcagtg gaagacacca ccctggagcg agcggaccag gaggtcacat   2640
ctgtcctgaa gagactgctg ggccccaagg cgccaggccc ctccacaggg gacctcactg   2700
gccctggccc ctgccccagg ggggcacccg cactccagga aaccggctcc cagcccccag   2760
tcaccggaac ttcggaggca cctgccgtgc ccccagggt gccacagccc ctcctccacg   2820
aaggcccaga gcaggagccg gaggccattg ccagagccca ggaatggact gtgcccattc   2880
ggatggaggg tgcagcctgg cccggggcag gcacaggga gctgctctgg gacgtccaca    2940
gccacgtggt cagagagacc acacagagga cctacacata ccaggccatc gacacgcaca   3000
ccgcacggcc cccatccatg caggtaacca tcgaggatgt gcaggcacag acaggcggaa   3060
cggcccaatt cgaggctatc attgagggcg acccacagcc ctcggtgacc tggtacaagg   3120
acagcgtcca gctggtggac agcacccggc ttagccagca gcaagaaggc accacatact   3180
ccctggtgct gaggcatgtg gcctcgaagg atgccggcgt ttacacctgc ctggcccaaa   3240
```

```
acactggtgg ccaggtgctc tgcaaggcag agctgctggt gcttgggggg gacaatgagc    3300
cggactcaga gaagcaaagc caccggagga agctgcactc cttctatgag gtcaaggagg    3360
agattggaag gggcgtgttt ggcttcgtaa aaagagtgca gcacaaagga aacaagatct    3420
tgtgcgctgc caagttcatc cccctacgga gcagaactcg ggcccaggca tacagggagc    3480
gagacatcct ggccgcgctg agccaccgc tggtcacggg gctgctggac cagtttgaga    3540
cccgcaagac cctcatcctc atcctggagc tgtgctcatc cgaggagctg ctggaccgcc    3600
tgtacaggaa gggcgtggtg acggaggccg aggtcaaggt ctacatccag cagctggtgg    3660
aggggctgca ctacctgcac agccatggcg ttctccacct ggacataaag ccctctaaca    3720
tcctgatggt gcatcctgcc cgggaagaca ttaaaatctg cgactttggc tttgcccaga    3780
acatcacccc agcagagctg cagttcagcc agtacggctc ccctgagttc gtctcccccg    3840
agatcatcca gcagaaccct gtgagcgaag cctccgacat ttgggccatg ggtgtcatct    3900
cctacctcag cctgacctgc tcatccccat ttgccggcga gagtgaccgt gccaccctcc    3960
tgaacgtcct ggaggggcgc gtgtcatgga gcagcccat ggctgcccac ctcagcgaag    4020
acgccaaaga cttcatcaag gctacgctgc agagagcccc tcaggcccgg cctagtgcgg    4080
cccagtgcct ctcccacccc tggttcctga atccatgcc tgcggaggag gcccacttca    4140
tcaacaccaa gcagctcaag ttcctcctgg cccgaagtcg ctggcagcgt tccctgatga    4200
gctacaagtc catcctggtg atgcgctcca tccctgagct gctgcggggc cacccgaca    4260 gccccteccet cggcgtagcc cggcacctct gcagggacac tggtggctcc tccagttcct    4320
cctcctcctc tgacaacgag ctcgccccat ttgcccgggc taagtcactg ccaccctccc    4380
cggtgacaca ctcaccactg ctgcaccccc ggggcttcct gcggccctcg gccagcctgc    4440
ctgaggaagc cgaggccagt gagcgctcca ccgaggcccc agctccgcct gcatctcccg    4500
agggtgccgg gccaccggcc gcccagggct gcgtgcccg gcacagcgtc atccgcagcc    4560
tgttctacca ccagcgggt gagagccctg agcacggggc cctggccccg gggagcaggc    4620 ggcaccggc ccggcggcgg cacctgctga agggcgggta cattgcgggg gcgctgccag    4680
gcctgcgcga gccactgatg gagcaccgcg tgctggagga ggaggccgcc agggaggagc    4740
aggccaccct cctggccaaa gcccctcat tcgagactgc cctccggctg cctgcctctg    4800
gcacccactt ggcccctggc cacagccact ccctggaaca tgactctccg agcaccccc    4860 gccctctcc ggaggcctgc ggtgaggcac agcgactgcc ttcagccccc tccggggggg    4920
cccctatcag ggacatgggg cacctcagg gctccaagca gcttccatcc actggtggcc    4980
acccaggcac tgctcagcca gagaggccat ccccggacag cccttggggg cagccagccc    5040
cttcctgcca ccccaagcag ggttctgccc ccaggagg ctgcagcccc cacccagcag    5100
ttgccccatg ccctcctggc tccttccctc caggatcttg caaagaggcc cccttagtac    5160
cctcaagccc cttcttggga cagccccagg cacccctgc ccctgccaaa gcaagccccc    5220
cattggactc taagatgggg cctggagaca tctctcttcc tgggaggcca aaacccggcc    5280
cctgcagttc cccagggtca gcctcccagg cgagctcttc ccaagtgagc tccctcaggg    5340
tgggctcctc ccaggtgggc acagagcctg gcccctccct ggatgcggag ggctggaccc    5400
aggaggctga ggatcgtcc gactccacac ccaccttgca gcggcctcag gaacaggcga    5460
ccatgcgcaa gttctccctg gtggtcgcg ggggctacgc aggcgtggct ggctatggca    5520
cctttgcctt tggtgggagat gcaggggca tgctggggca ggggcccatg tgggccagga    5580
tagcctgggc tgtgtcccag tcagaggagg aggagcagga ggaggccagg gctgagtccc    5640
```

-continued

| | |
|---|---|
| agtcggagga gcagcaggag gccagggctg agagcccact gccccaggtc agtgcaaggc | 5700 |
| ctgtgcctga ggtcggcagg gctcccacca ggagctctcc agagcccacc ccatgggagg | 5760 |
| acatcgggca ggtctccctg gtgcagatcc gggacctgtc aggtgatgcg gaggcggccg | 5820 |
| acacaatatc cctggacatt tccgaggtgg accccgccta cctcaacctc tcagacctgt | 5880 |
| acgatatcaa gtacctccca ttcgagttta tgatcttcag gaaagtcccc aagtccgctc | 5940 |
| agccagagcc gccctccccc atggctgagg aggagctggc cgagttcccg gagcccacgt | 6000 |
| ggccctggcc aggtgaactg gccccccacg caggcctgga gatcacagag gagtcagagg | 6060 |
| atgtggacgc gctgctggca gaggctgccg tgggcaggaa gcgcaagtgg tcctcgccgt | 6120 |
| cacgcagcct cttccacttc cctgggaggc acctgccgct ggatgagcct gcagagctgg | 6180 |
| ggctgcgtga gagagtgaag gcctccgtgg agcacatctc ccggatcctg aagggcaggc | 6240 |
| cggaaggtct ggagaaggag gggcccccca ggaagaagcc aggccttgct tccttccggc | 6300 |
| tctcaggtct gaagagctgg gaccgagcgc cgacattcct aagggagctc tcagatgaga | 6360 |
| ctgtggtcct gggccagtca gtgacactgg cctgccaggt gtcagcccag ccagctgccc | 6420 |
| aggccacctg gagcaaagac ggagcccccc tggagagcag cagccgtgtc ctcatctctg | 6480 |
| ccaccctcaa gaacttccag cttctgacca tcctggtggt ggtggctgag gacctgggtg | 6540 |
| tgtacacctg cagcgtgagc aatgcgctgg ggacagtgac caccacgggc gtcctccgga | 6600 |
| aggcagagcg cccctcatct tcgccatgcc cggatatcgg ggaggtgtac gcggatgggg | 6660 |
| tgctgctggt ctggaagccc gtggaatcct acggccctgt gacctacatt gtgcagtgca | 6720 |
| gcctagaagg cggcagctgg accacactgg cctccgacat cttgactgc tgctacctga | 6780 |
| ccagcaagct ctcccggggt ggcacctaca ccttccgcac ggcatgtgtc agcaaggcag | 6840 |
| gaatgggtcc ctacagcagc ccctcggagc aagtcctcct gggagcgccc agccacctgg | 6900 |
| cctctgagga ggagagccag gggcggtcag cccaaccccct gcccagcaca agaccttcg | 6960 |
| cattccagac acagatccag aggggccgct tcagcgtggt gcggcaatgc tgggagaagg | 7020 |
| ccagcgggcg ggcgctggcc gccaagatca tccctacca ccccaaggac aagacagcag | 7080 |
| tgctgcgcga atacgaggcc ctcaagggcc tgcgccaccc gcacctggcc cagctgcacg | 7140 |
| cagcctacct cagccccgg cacctggtgc tcatcttgga gctgtgctct gggcccgagc | 7200 |
| tgctcccctg cctggccgag agggcctcct actcagaatc cgaggtgaag gactacctgt | 7260 |
| ggcagatgtt gagtgccacc cagtacctgc acaaccagca catcctgcac ctggacctga | 7320 |
| ggtccgagaa catgatcatc accgaataca acctgctcaa ggtcgtggac ctgggcaatg | 7380 |
| cacagagcct cagccaggag aaggtgctgc cctcagacaa gttcaaggac tacctagaga | 7440 |
| ccatggctcc agagctcctg gagggccagg gggctgttcc acagacagac atctgggcca | 7500 |
| tcggtgtgac agccttcatc atgctgagcg ccgagtaccc ggtgagcagc gagggtgcac | 7560 |
| gcgacctgca gagaggactg cgcaaggggc tggtccggct gagccgctgc tacgcggggc | 7620 |
| tgtccggggg cgccgtggcc ttcctgcgca gcactctgtg cgcccagccc tggggccggc | 7680 |
| cctgcgcgtc cagctgcctg cagtgcccgt ggctaacaga ggagggcccg gcctgttcgc | 7740 |
| ggcccgcgcc cgtgaccttc cctaccgcgc ggctgcgcgt cttcgtgcgc aatcgcgaga | 7800 |
| agagacgcgc gctgctgtac aagaggcaca acctggccca ggtgcgctga gggtcgcccc | 7860 |
| ggccacaccc ttggtctccc cgctgggggt cgctgcagac gcgccaataa aaacgcacag | 7920 |
| ccgggcga | 7928 |

```
<210> SEQ ID NO 6
<211> LENGTH: 2596
<212> TYPE: PRT
<213> ORGANISM: Homo sapiens

<400> SEQUENCE: 6

Met Leu Glu Arg Phe Thr Pro Lys Lys Val Lys Lys Gly Ser Ser Ile
1               5                   10                  15

Thr Phe Ser Val Lys Val Glu Gly Arg Pro Val Pro Thr Val His Trp
            20                  25                  30

Leu Arg Glu Glu Ala Glu Arg Gly Val Leu Trp Ile Gly Pro Asp Thr
        35                  40                  45

Pro Gly Tyr Thr Val Ala Ser Ser Ala Gln Gln His Ser Leu Val Leu
    50                  55                  60

Leu Asp Val Gly Arg Gln His Gln Gly Thr Tyr Thr Cys Ile Ala Ser
65                  70                  75                  80

Asn Ala Ala Gly Gln Ala Leu Cys Ser Ala Ser Leu His Val Ser Gly
                85                  90                  95

Leu Pro Lys Val Glu Glu Gln Glu Lys Val Lys Glu Ala Leu Ile Ser
            100                 105                 110

Thr Phe Leu Gln Gly Thr Thr Gln Ala Ile Ser Ala Gln Gly Leu Glu
        115                 120                 125

Thr Ala Ser Phe Ala Asp Leu Gly Gly Gln Arg Lys Glu Glu Pro Leu
    130                 135                 140

Ala Ala Lys Glu Ala Leu Gly His Leu Ser Leu Ala Glu Val Gly Thr
145                 150                 155                 160

Glu Glu Phe Leu Gln Lys Leu Thr Ser Gln Ile Thr Glu Met Val Ser
                165                 170                 175

Ala Lys Ile Thr Gln Ala Lys Leu Gln Val Pro Gly Gly Asp Ser Asp
            180                 185                 190

Glu Asp Ser Lys Thr Pro Ser Ala Ser Pro Arg His Gly Arg Ser Arg
        195                 200                 205

Pro Ser Ser Ser Ile Gln Glu Ser Ser Glu Ser Glu Asp Gly Asp
    210                 215                 220

Ala Arg Gly Glu Ile Phe Asp Ile Tyr Val Val Thr Ala Asp Tyr Leu
225                 230                 235                 240

Pro Leu Gly Ala Glu Gln Asp Ala Ile Thr Leu Arg Glu Gly Gln Tyr
                245                 250                 255

Val Glu Val Leu Asp Ala Ala His Pro Leu Arg Trp Leu Val Arg Thr
            260                 265                 270

Lys Pro Thr Lys Ser Ser Pro Ser Arg Gln Gly Trp Val Ser Pro Ala
        275                 280                 285

Tyr Leu Asp Arg Arg Leu Lys Leu Ser Pro Glu Trp Gly Ala Ala Glu
    290                 295                 300

Ala Pro Glu Phe Pro Gly Glu Ala Val Ser Glu Asp Glu Tyr Lys Ala
305                 310                 315                 320

Arg Leu Ser Ser Val Ile Gln Glu Leu Leu Ser Ser Glu Gln Ala Phe
                325                 330                 335

Val Glu Glu Leu Gln Phe Leu Gln Ser His His Leu Gln His Leu Glu
            340                 345                 350

Arg Cys Pro His Val Pro Ile Ala Val Ala Gly Gln Lys Ala Val Ile
        355                 360                 365

Phe Arg Asn Val Arg Asp Ile Gly Arg Phe His Ser Ser Phe Leu Gln
    370                 375                 380
```

```
Glu Leu Gln Gln Cys Asp Thr Asp Asp Val Ala Met Cys Phe Ile
385                 390                 395                 400

Lys Asn Gln Ala Ala Phe Glu Gln Tyr Leu Glu Phe Leu Val Gly Arg
            405                 410                 415

Val Gln Ala Glu Ser Val Val Ser Thr Ala Ile Gln Glu Phe Tyr
                420                 425                 430

Lys Lys Tyr Ala Glu Ala Leu Leu Ala Gly Asp Pro Ser Gln Pro
            435                 440                 445

Pro Pro Pro Leu Gln His Tyr Leu Glu Gln Pro Val Glu Arg Val
        450                 455                 460

Gln Arg Tyr Gln Ala Leu Leu Lys Glu Leu Ile Arg Asn Lys Ala Arg
465                 470                 475                 480

Asn Arg Gln Asn Cys Ala Leu Leu Glu Gln Ala Tyr Ala Val Val Ser
                485                 490                 495

Ala Leu Pro Gln Arg Ala Glu Asn Lys Leu His Val Ser Leu Met Glu
                500                 505                 510

Asn Tyr Pro Gly Thr Leu Glu Ala Leu Gly Glu Pro Ile Arg Gln Gly
                515                 520                 525

His Phe Ile Val Trp Glu Gly Ala Pro Gly Ala Arg Met Pro Trp Lys
                530                 535                 540

Gly His Asn Arg His Val Phe Leu Phe Arg Asn His Leu Val Ile Cys
545                 550                 555                 560

Lys Pro Arg Arg Asp Ser Arg Thr Asp Thr Val Ser Tyr Val Phe Arg
                565                 570                 575

Asn Met Met Lys Leu Ser Ser Ile Asp Leu Asn Asp Gln Val Glu Gly
                580                 585                 590

Asp Asp Arg Ala Phe Glu Val Trp Gln Glu Arg Glu Asp Ser Val Arg
                595                 600                 605

Lys Tyr Leu Leu Gln Ala Arg Thr Ala Ile Ile Lys Ser Ser Trp Val
610                 615                 620

Lys Glu Ile Cys Gly Ile Gln Gln Arg Leu Ala Leu Pro Val Trp Arg
625                 630                 635                 640

Pro Pro Asp Phe Glu Glu Leu Ala Asp Cys Thr Ala Glu Leu Gly
                645                 650                 655

Glu Thr Val Lys Leu Ala Cys Arg Val Thr Gly Thr Pro Lys Pro Val
                660                 665                 670

Ile Ser Trp Tyr Lys Asp Gly Lys Ala Val Gln Val Asp Pro His His
                675                 680                 685

Ile Leu Ile Glu Asp Pro Asp Gly Ser Cys Ala Leu Ile Leu Asp Ser
                690                 695                 700

Leu Thr Gly Val Asp Ser Gly Gln Tyr Met Cys Phe Ala Ala Ser Ala
705                 710                 715                 720

Ala Gly Asn Cys Ser Thr Leu Gly Lys Ile Leu Val Gln Val Pro Pro
                725                 730                 735

Arg Phe Val Asn Lys Val Arg Ala Ser Pro Phe Val Glu Gly Glu Asp
                740                 745                 750

Ala Gln Phe Thr Cys Thr Ile Glu Gly Ala Pro Tyr Pro Gln Ile Arg
                755                 760                 765

Trp Tyr Lys Asp Gly Ala Leu Leu Thr Thr Gly Asn Lys Phe Gln Thr
                770                 775                 780

Leu Ser Glu Pro Arg Ser Gly Leu Leu Val Leu Val Ile Arg Ala Ala
785                 790                 795                 800
```

```
Ser Lys Glu Asp Leu Gly Leu Tyr Glu Cys Glu Leu Val Asn Arg Leu
            805                 810                 815

Gly Ser Ala Arg Ala Ser Ala Glu Leu Arg Ile Gln Ser Pro Met Leu
            820                 825                 830

Gln Ala Gln Glu Gln Cys His Arg Glu Gln Leu Val Ala Ala Val Glu
            835                 840                 845

Asp Thr Thr Leu Glu Arg Ala Asp Gln Glu Val Thr Ser Val Leu Lys
850                 855                 860

Arg Leu Leu Gly Pro Lys Ala Pro Gly Pro Ser Thr Gly Asp Leu Thr
865                 870                 875                 880

Gly Pro Gly Pro Cys Pro Arg Gly Ala Pro Ala Leu Gln Glu Thr Gly
                    885                 890                 895

Ser Gln Pro Pro Val Thr Gly Thr Ser Glu Ala Pro Ala Val Pro Pro
            900                 905                 910

Arg Val Pro Gln Pro Leu Leu His Glu Gly Pro Glu Gln Glu Pro Glu
            915                 920                 925

Ala Ile Ala Arg Ala Gln Glu Trp Thr Val Pro Ile Arg Met Glu Gly
930                 935                 940

Ala Ala Trp Pro Gly Ala Gly Thr Gly Glu Leu Leu Trp Asp Val His
945                 950                 955                 960

Ser His Val Val Arg Glu Thr Thr Gln Arg Thr Tyr Thr Tyr Gln Ala
                    965                 970                 975

Ile Asp Thr His Thr Ala Arg Pro Pro Ser Met Gln Val Thr Ile Glu
                    980                 985                 990

Asp Val Gln Ala Gln Thr Gly Gly Thr Ala Gln Phe Glu Ala Ile Ile
            995                 1000                1005

Glu Gly Asp Pro Gln Pro Ser Val Thr Trp Tyr Lys Asp Ser Val Gln
            1010                1015                1020

Leu Val Asp Ser Thr Arg Leu Ser Gln Gln Gln Glu Gly Thr Thr Tyr
1025                1030                1035                1040

Ser Leu Val Leu Arg His Val Ala Ser Lys Asp Ala Gly Val Tyr Thr
                    1045                1050                1055

Cys Leu Ala Gln Asn Thr Gly Gly Gln Val Leu Cys Lys Ala Glu Leu
            1060                1065                1070

Leu Val Leu Gly Gly Asp Asn Glu Pro Asp Ser Glu Lys Gln Ser His
            1075                1080                1085

Arg Arg Lys Leu His Ser Phe Tyr Glu Val Lys Glu Glu Ile Gly Arg
            1090                1095                1100

Gly Val Phe Gly Phe Val Lys Arg Val Gln His Lys Gly Asn Lys Ile
1105                1110                1115                1120

Leu Cys Ala Ala Lys Phe Ile Pro Leu Arg Ser Arg Thr Arg Ala Gln
                    1125                1130                1135

Ala Tyr Arg Glu Arg Asp Ile Leu Ala Ala Leu Ser His Pro Leu Val
                    1140                1145                1150

Thr Gly Leu Leu Asp Gln Phe Glu Thr Arg Lys Thr Leu Ile Leu Ile
            1155                1160                1165

Leu Glu Leu Cys Ser Ser Glu Glu Leu Leu Asp Arg Leu Tyr Arg Lys
            1170                1175                1180

Gly Val Val Thr Glu Ala Glu Val Lys Val Tyr Ile Gln Gln Leu Val
1185                1190                1195                1200

Glu Gly Leu His Tyr Leu His Ser His Gly Val Leu His Leu Asp Ile
            1205                1210                1215

Lys Pro Ser Asn Ile Leu Met Val His Pro Ala Arg Glu Asp Ile Lys
```

-continued

```
                1220                1225                1230
Ile Cys Asp Phe Gly Phe Ala Gln Asn Ile Thr Pro Ala Glu Leu Gln
    1235                1240                1245

Phe Ser Gln Tyr Gly Ser Pro Glu Phe Val Ser Pro Glu Ile Ile Gln
        1250                1255                1260

Gln Asn Pro Val Ser Glu Ala Ser Asp Ile Trp Ala Met Gly Val Ile
1265                1270                1275                1280

Ser Tyr Leu Ser Leu Thr Cys Ser Ser Pro Phe Ala Gly Glu Ser Asp
            1285                1290                1295

Arg Ala Thr Leu Leu Asn Val Leu Glu Gly Arg Val Ser Trp Ser Ser
        1300                1305                1310

Pro Met Ala Ala His Leu Ser Glu Asp Ala Lys Asp Phe Ile Lys Ala
        1315                1320                1325

Thr Leu Gln Arg Ala Pro Gln Ala Arg Pro Ser Ala Ala Gln Cys Leu
        1330                1335                1340

Ser His Pro Trp Phe Leu Lys Ser Met Pro Ala Glu Glu Ala His Phe
1345                1350                1355                1360

Ile Asn Thr Lys Gln Leu Lys Phe Leu Leu Ala Arg Ser Arg Trp Gln
        1365                1370                1375

Arg Ser Leu Met Ser Tyr Lys Ser Ile Leu Val Met Arg Ser Ile Pro
        1380                1385                1390

Glu Leu Leu Arg Gly Pro Pro Asp Ser Pro Ser Leu Gly Val Ala Arg
        1395                1400                1405

His Leu Cys Arg Asp Thr Gly Gly Ser Ser Ser Ser Ser Ser Ser Ser
        1410                1415                1420

Asp Asn Glu Leu Ala Pro Phe Ala Arg Ala Lys Ser Leu Pro Pro Ser
1425                1430                1435                1440

Pro Val Thr His Ser Pro Leu Leu His Pro Arg Gly Phe Leu Arg Pro
            1445                1450                1455

Ser Ala Ser Leu Pro Glu Glu Ala Glu Ala Ser Glu Arg Ser Thr Glu
        1460                1465                1470

Ala Pro Ala Pro Pro Ala Ser Pro Glu Gly Ala Gly Pro Pro Ala Ala
        1475                1480                1485

Gln Gly Cys Val Pro Arg His Ser Val Ile Arg Ser Leu Phe Tyr His
        1490                1495                1500

Gln Ala Gly Glu Ser Pro Glu His Gly Ala Leu Ala Pro Gly Ser Arg
1505                1510                1515                1520

Arg His Pro Ala Arg Arg His Leu Leu Lys Gly Gly Tyr Ile Ala
            1525                1530                1535

Gly Ala Leu Pro Gly Leu Arg Glu Pro Leu Met Glu His Arg Val Leu
        1540                1545                1550

Glu Glu Glu Ala Ala Arg Glu Glu Gln Ala Thr Leu Leu Ala Lys Ala
        1555                1560                1565

Pro Ser Phe Glu Thr Ala Leu Arg Leu Pro Ala Ser Gly Thr His Leu
        1570                1575                1580

Ala Pro Gly His Ser His Ser Leu Glu His Asp Ser Pro Ser Thr Pro
1585                1590                1595                1600

Arg Pro Ser Ser Glu Ala Cys Gly Glu Ala Gln Arg Leu Pro Ser Ala
            1605                1610                1615

Pro Ser Gly Gly Ala Pro Ile Arg Asp Met Gly His Pro Gln Gly Ser
        1620                1625                1630

Lys Gln Leu Pro Ser Thr Gly Gly His Pro Gly Thr Ala Gln Pro Glu
        1635                1640                1645
```

```
Arg Pro Ser Pro Asp Ser Pro Trp Gly Gln Pro Ala Pro Phe Cys His
    1650                1655                1660
Pro Lys Gln Gly Ser Ala Pro Gln Glu Gly Cys Ser Pro His Pro Ala
1665                1670                1675                1680
Val Ala Pro Cys Pro Pro Gly Ser Phe Pro Pro Gly Ser Cys Lys Glu
            1685                1690                1695
Ala Pro Leu Val Pro Ser Ser Pro Phe Leu Gly Gln Pro Gln Ala Pro
                1700                1705                1710
Pro Ala Pro Ala Lys Ala Ser Pro Pro Leu Asp Ser Lys Met Gly Pro
        1715                1720                1725
Gly Asp Ile Ser Leu Pro Gly Arg Pro Lys Pro Gly Pro Cys Ser Ser
    1730                1735                1740
Pro Gly Ser Ala Ser Gln Ala Ser Ser Ser Gln Val Ser Ser Leu Arg
1745                1750                1755                1760
Val Gly Ser Ser Gln Val Gly Thr Glu Pro Gly Pro Ser Leu Asp Ala
            1765                1770                1775
Glu Gly Trp Thr Gln Glu Ala Glu Asp Leu Ser Asp Ser Thr Pro Thr
                1780                1785                1790
Leu Gln Arg Pro Gln Glu Gln Ala Thr Met Arg Lys Phe Ser Leu Gly
        1795                1800                1805
Gly Arg Gly Gly Tyr Ala Gly Val Ala Gly Tyr Gly Thr Phe Ala Phe
    1810                1815                1820
Gly Gly Asp Ala Gly Gly Met Leu Gly Gln Gly Pro Met Trp Ala Arg
1825                1830                1835                1840
Ile Ala Trp Ala Val Ser Gln Ser Glu Glu Glu Gln Glu Glu Ala
            1845                1850                1855
Arg Ala Glu Ser Gln Ser Glu Glu Gln Gln Glu Ala Arg Ala Glu Ser
                1860                1865                1870
Pro Leu Pro Gln Val Ser Ala Arg Pro Val Pro Glu Val Gly Arg Ala
        1875                1880                1885
Pro Thr Arg Ser Ser Pro Glu Pro Thr Pro Trp Glu Asp Ile Gly Gln
    1890                1895                1900
Val Ser Leu Val Gln Ile Arg Asp Leu Ser Gly Asp Ala Glu Ala Ala
1905                1910                1915                1920
Asp Thr Ile Ser Leu Asp Ile Ser Glu Val Asp Pro Ala Tyr Leu Asn
            1925                1930                1935
Leu Ser Asp Leu Tyr Asp Ile Lys Tyr Leu Pro Phe Glu Phe Met Ile
                1940                1945                1950
Phe Arg Lys Val Pro Lys Ser Ala Gln Pro Glu Pro Pro Ser Pro Met
        1955                1960                1965
Ala Glu Glu Glu Leu Ala Glu Phe Pro Glu Pro Thr Trp Pro Trp Pro
    1970                1975                1980
Gly Glu Leu Gly Pro His Ala Gly Leu Glu Ile Thr Glu Glu Ser Glu
1985                1990                1995                2000
Asp Val Asp Ala Leu Leu Ala Glu Ala Ala Val Gly Arg Lys Arg Lys
            2005                2010                2015
Trp Ser Ser Pro Ser Arg Ser Leu Phe His Phe Pro Gly Arg His Leu
                2020                2025                2030
Pro Leu Asp Glu Pro Ala Glu Leu Gly Leu Arg Glu Arg Val Lys Ala
        2035                2040                2045
Ser Val Glu His Ile Ser Arg Ile Leu Lys Gly Arg Pro Glu Gly Leu
    2050                2055                2060
```

-continued

```
Glu Lys Glu Gly Pro Pro Arg Lys Lys Pro Gly Leu Ala Ser Phe Arg
2065                2070                2075                2080

Leu Ser Gly Leu Lys Ser Trp Asp Arg Ala Pro Thr Phe Leu Arg Glu
            2085                2090                2095

Leu Ser Asp Glu Thr Val Val Leu Gly Gln Ser Val Thr Leu Ala Cys
        2100                2105                2110

Gln Val Ser Ala Gln Pro Ala Gln Ala Thr Trp Ser Lys Asp Gly
    2115                2120                2125

Ala Pro Leu Glu Ser Ser Arg Val Leu Ile Ser Ala Thr Leu Lys
2130                2135                2140

Asn Phe Gln Leu Leu Thr Ile Leu Val Val Val Ala Glu Asp Leu Gly
2145                2150                2155                2160

Val Tyr Thr Cys Ser Val Ser Asn Ala Leu Gly Thr Val Thr Thr Thr
                2165                2170                2175

Gly Val Leu Arg Lys Ala Glu Arg Pro Ser Ser Ser Pro Cys Pro Asp
            2180                2185                2190

Ile Gly Glu Val Tyr Ala Asp Gly Val Leu Leu Val Trp Lys Pro Val
        2195                2200                2205

Glu Ser Tyr Gly Pro Val Thr Tyr Ile Val Gln Cys Ser Leu Glu Gly
    2210                2215                2220

Gly Ser Trp Thr Thr Leu Ala Ser Asp Ile Phe Asp Cys Cys Tyr Leu
2225                2230                2235                2240

Thr Ser Lys Leu Ser Arg Gly Gly Thr Tyr Thr Phe Arg Thr Ala Cys
                2245                2250                2255

Val Ser Lys Ala Gly Met Gly Pro Tyr Ser Ser Pro Ser Glu Gln Val
            2260                2265                2270

Leu Leu Gly Ala Pro Ser His Leu Ala Ser Glu Glu Ser Gln Gly
        2275                2280                2285

Arg Ser Ala Gln Pro Leu Pro Ser Thr Lys Thr Phe Ala Phe Gln Thr
    2290                2295                2300

Gln Ile Gln Arg Gly Arg Phe Ser Val Val Arg Gln Cys Trp Glu Lys
2305                2310                2315                2320

Ala Ser Gly Arg Ala Leu Ala Ala Lys Ile Ile Pro Tyr His Pro Lys
                2325                2330                2335

Asp Lys Thr Ala Val Leu Arg Glu Tyr Glu Ala Leu Lys Gly Leu Arg
            2340                2345                2350

His Pro His Leu Ala Gln Leu His Ala Ala Tyr Leu Ser Pro Arg His
        2355                2360                2365

Leu Val Leu Ile Leu Glu Leu Cys Ser Gly Pro Glu Leu Leu Pro Cys
    2370                2375                2380

Leu Ala Glu Arg Ala Ser Tyr Ser Glu Ser Glu Val Lys Asp Tyr Leu
2385                2390                2395                2400

Trp Gln Met Leu Ser Ala Thr Gln Tyr Leu His Asn Gln His Ile Leu
                2405                2410                2415

His Leu Asp Leu Arg Ser Glu Asn Met Ile Ile Thr Glu Tyr Asn Leu
            2420                2425                2430

Leu Lys Val Val Asp Leu Gly Asn Ala Gln Ser Leu Ser Gln Glu Lys
        2435                2440                2445

Val Leu Pro Ser Asp Lys Phe Lys Asp Tyr Leu Glu Thr Met Ala Pro
    2450                2455                2460

Glu Leu Leu Glu Gly Gln Gly Ala Val Pro Gln Thr Asp Ile Trp Ala
2465                2470                2475                2480

Ile Gly Val Thr Ala Phe Ile Met Leu Ser Ala Glu Tyr Pro Val Ser
```

-continued

```
                 2485                2490                2495

Ser Glu Gly Ala Arg Asp Leu Gln Arg Gly Leu Arg Lys Gly Leu Val
            2500                2505                2510

Arg Leu Ser Arg Cys Tyr Ala Gly Leu Ser Gly Gly Ala Val Ala Phe
            2515                2520                2525

Leu Arg Ser Thr Leu Cys Ala Gln Pro Trp Gly Arg Pro Cys Ala Ser
            2530                2535                2540

Ser Cys Leu Gln Cys Pro Trp Leu Thr Glu Glu Gly Pro Ala Cys Ser
2545                2550                2555                2560

Arg Pro Ala Pro Val Thr Phe Pro Thr Ala Arg Leu Arg Val Phe Val
            2565                2570                2575

Arg Asn Arg Glu Lys Arg Arg Ala Leu Leu Tyr Lys Arg His Asn Leu
            2580                2585                2590

Ala Gln Val Arg
            2595

<210> SEQ ID NO 7
<211> LENGTH: 871
<212> TYPE: PRT
<213> ORGANISM: Homo sapiens

<400> SEQUENCE: 7

Met Gly Pro Gly Asp Ile Ser Leu Pro Gly Arg Pro Lys Pro Gly Pro
1               5                   10                  15

Cys Ser Ser Pro Gly Ser Ala Ser Gln Ala Ser Ser Ser Gln Val Ser
            20                  25                  30

Ser Leu Arg Val Gly Ser Ser Gln Val Gly Thr Glu Pro Gly Pro Ser
        35                  40                  45

Leu Asp Ala Glu Gly Trp Thr Gln Glu Ala Glu Asp Leu Ser Asp Ser
    50                  55                  60

Thr Pro Thr Leu Gln Arg Pro Gln Glu Gln Ala Thr Met Arg Lys Phe
65                  70                  75                  80

Ser Leu Gly Gly Arg Gly Gly Tyr Ala Gly Val Ala Gly Tyr Gly Thr
                85                  90                  95

Phe Ala Phe Gly Gly Asp Ala Gly Gly Met Leu Gly Gln Gly Pro Met
            100                 105                 110

Trp Ala Arg Ile Ala Trp Ala Val Ser Gln Ser Glu Glu Glu Glu Gln
        115                 120                 125

Glu Glu Ala Arg Ala Glu Ser Gln Ser Glu Glu Gln Gln Glu Ala Arg
    130                 135                 140

Ala Glu Ser Pro Leu Pro Gln Val Ser Ala Arg Pro Val Pro Glu Val
145                 150                 155                 160

Gly Arg Ala Pro Thr Arg Ser Ser Pro Glu Pro Thr Pro Trp Glu Asp
                165                 170                 175

Ile Gly Gln Val Ser Leu Val Gln Ile Arg Asp Leu Ser Gly Asp Ala
            180                 185                 190

Glu Ala Ala Asp Thr Ile Ser Leu Asp Ile Ser Glu Val Asp Pro Ala
        195                 200                 205

Tyr Leu Asn Leu Ser Asp Leu Tyr Asp Ile Lys Tyr Leu Pro Phe Glu
    210                 215                 220

Phe Met Ile Phe Arg Lys Val Pro Lys Ser Ala Gln Pro Glu Pro Pro
225                 230                 235                 240

Ser Pro Met Ala Glu Glu Leu Ala Glu Phe Pro Glu Pro Thr Trp
                245                 250                 255
```

```
Pro Trp Pro Gly Glu Leu Gly Pro His Ala Gly Leu Glu Ile Thr Glu
            260                 265                 270
Glu Ser Glu Asp Val Asp Ala Leu Leu Ala Glu Ala Ala Val Gly Arg
            275                 280                 285
Lys Arg Lys Trp Ser Ser Pro Ser Arg Ser Leu Phe His Phe Pro Gly
            290                 295                 300
Arg His Leu Pro Leu Asp Glu Pro Ala Glu Leu Gly Leu Arg Glu Arg
305                 310                 315                 320
Val Lys Ala Ser Val Glu His Ile Ser Arg Ile Leu Lys Gly Arg Pro
                325                 330                 335
Glu Gly Leu Glu Lys Glu Gly Pro Pro Arg Lys Lys Pro Gly Leu Ala
            340                 345                 350
Ser Phe Arg Leu Ser Gly Leu Lys Ser Trp Asp Arg Ala Pro Thr Phe
        355                 360                 365
Leu Arg Glu Leu Ser Asp Glu Thr Val Val Leu Gly Gln Ser Val Thr
    370                 375                 380
Leu Ala Cys Gln Val Ser Ala Gln Pro Ala Ala Gln Ala Thr Trp Ser
385                 390                 395                 400
Lys Asp Gly Ala Pro Leu Glu Ser Ser Arg Val Leu Ile Ser Ala
            405                 410                 415
Thr Leu Lys Asn Phe Gln Leu Leu Thr Ile Leu Val Val Val Ala Glu
            420                 425                 430
Asp Leu Gly Val Tyr Thr Cys Ser Val Ser Asn Ala Leu Gly Thr Val
        435                 440                 445
Thr Thr Thr Gly Val Leu Arg Lys Ala Glu Arg Pro Ser Ser Ser Pro
    450                 455                 460
Cys Pro Asp Ile Gly Glu Val Tyr Ala Asp Gly Val Leu Leu Val Trp
465                 470                 475                 480
Lys Pro Val Glu Ser Tyr Gly Pro Val Thr Tyr Ile Val Gln Cys Ser
                485                 490                 495
Leu Glu Gly Gly Ser Trp Thr Thr Leu Ala Ser Asp Ile Phe Asp Cys
            500                 505                 510
Cys Tyr Leu Thr Ser Lys Leu Ser Arg Gly Gly Thr Tyr Thr Phe Arg
        515                 520                 525
Thr Ala Cys Val Ser Lys Ala Gly Met Gly Pro Tyr Ser Ser Pro Ser
    530                 535                 540
Glu Gln Val Leu Leu Gly Gly Pro Ser His Leu Ala Ser Glu Glu Glu
545                 550                 555                 560
Ser Gln Gly Arg Ser Ala Gln Pro Leu Pro Ser Thr Lys Thr Phe Ala
                565                 570                 575
Phe Gln Thr Gln Ile Gln Arg Gly Arg Phe Ser Val Val Arg Gln Cys
            580                 585                 590
Trp Glu Lys Ala Ser Gly Arg Ala Leu Ala Ala Lys Ile Ile Pro Tyr
        595                 600                 605
His Pro Lys Asp Lys Thr Ala Val Leu Arg Glu Tyr Glu Ala Leu Lys
    610                 615                 620
Gly Leu Arg His Pro His Leu Ala Gln Leu His Ala Ala Tyr Leu Ser
625                 630                 635                 640
Pro Arg His Leu Val Leu Ile Leu Glu Leu Cys Ser Gly Pro Glu Leu
                645                 650                 655
Leu Pro Cys Leu Ala Glu Arg Ala Ser Tyr Ser Glu Ser Glu Val Lys
            660                 665                 670
Asp Tyr Leu Trp Gln Met Leu Ser Ala Thr Gln Tyr Leu His Asn Gln
```

-continued

```
                675                 680                 685
His Ile Leu His Leu Asp Leu Arg Ser Glu Asn Met Ile Ile Thr Glu
            690                 695                 700
Tyr Asn Leu Leu Lys Val Val Asp Leu Gly Asn Ala Gln Ser Leu Ser
705                 710                 715                 720
Gln Glu Lys Val Leu Pro Ser Asp Lys Phe Lys Asp Tyr Leu Glu Thr
                725                 730                 735
Met Ala Pro Glu Leu Leu Glu Gly Gln Gly Ala Val Pro Gln Thr Asp
            740                 745                 750
Ile Trp Ala Ile Gly Val Thr Ala Phe Ile Met Leu Ser Ala Glu Tyr
                755                 760                 765
Pro Val Ser Ser Glu Gly Ala Arg Asp Leu Gln Arg Gly Leu Arg Lys
            770                 775                 780
Gly Leu Val Arg Leu Ser Arg Cys Tyr Ala Gly Leu Ser Gly Gly Ala
785                 790                 795                 800
Val Ala Phe Leu Arg Ser Thr Leu Cys Ala Gln Pro Trp Gly Arg Pro
                805                 810                 815
Cys Ala Ser Ser Cys Leu Gln Cys Pro Trp Leu Thr Glu Glu Gly Pro
            820                 825                 830
Ala Cys Ser Arg Pro Ala Pro Val Thr Phe Pro Thr Ala Arg Leu Arg
                835                 840                 845
Val Phe Val Arg Asn Arg Glu Lys Arg Arg Ala Leu Leu Tyr Lys Arg
            850                 855                 860
His Asn Leu Ala Gln Val Arg
865                 870

<210> SEQ ID NO 8
<211> LENGTH: 548
<212> TYPE: PRT
<213> ORGANISM: Rat norvegicus

<400> SEQUENCE: 8

Met Ala His Ile Ser Arg Ile Leu Lys Gly Lys Pro Glu Gly Pro Glu
1               5                   10                  15
Lys Glu Gly Pro Pro Arg Lys Lys Ala Gly Leu Ala Ser Phe Arg Leu
            20                  25                  30
Ser Gly Leu Lys Gly Arg Asp Gln Ala Pro Ser Phe Leu Arg Glu Leu
        35                  40                  45
Ser Asp Glu Ala Val Val Leu Gly Gln Ser Val Thr Leu Ala Cys Gln
    50                  55                  60
Val Leu Ala Gln Pro Thr Ala Gln Ala Thr Trp Ser Lys Asp Gly Ala
65                  70                  75                  80
Leu Leu Glu Ser Ser Gly His Leu Leu Ile Ser Ser Thr Leu Lys Asn
                85                  90                  95
Phe Gln Leu Leu Thr Ile Leu Val Val Thr Glu Glu Asp Leu Gly Thr
            100                 105                 110
Tyr Thr Cys Cys Val Ser Asn Pro Leu Gly Thr Ala Val Thr Thr Gly
        115                 120                 125
Val Leu Arg Lys Ala Glu Arg Pro Ser Ser Ser Pro Arg Pro Glu Val
    130                 135                 140
Gly Glu Leu Tyr Thr Asp Ala Val Leu Leu Val Trp Lys Pro Val Glu
145                 150                 155                 160
Ser Tyr Gly Pro Val Thr Tyr Ile Val Gln Cys Cys Ile Glu Gly Gly
                165                 170                 175
```

-continued

Ser Trp Thr Thr Leu Ala Ser Asp Ile Ser Asp Cys Cys Tyr Leu Thr
            180                 185                 190

Gly Lys Leu Pro Arg Gly Gly Met Tyr Thr Phe Arg Thr Ala Cys Val
        195                 200                 205

Ser Lys Ala Gly Met Gly Pro Tyr Ser Ser Pro Ser Glu Gln Val Leu
    210                 215                 220

Leu Gly Gly Pro Asn His Leu Ala Ser Glu Glu Ser Ser Arg Gly
225                 230                 235                 240

Arg Pro Ala Gln Leu Leu Pro Ser Thr Lys Thr Phe Ala Phe Gln Thr
                245                 250                 255

Gln Ile Arg Arg Gly Arg Phe Ser Val Val Arg Gln Cys Arg Glu Lys
            260                 265                 270

Ala Ser Gly Arg Ala Leu Ala Ala Lys Ile Val Pro Tyr Gln Pro Glu
        275                 280                 285

Asp Lys Thr Thr Val Leu Arg Glu Tyr Glu Ala Leu Lys Arg Leu His
    290                 295                 300

His Pro His Leu Ala Gln Leu His Ala Ala Tyr Leu Ser Pro Arg His
305                 310                 315                 320

Leu Val Leu Ile Leu Glu Leu Cys Ser Gly Pro Glu Leu Leu Pro Ser
                325                 330                 335

Leu Ala Glu Arg Asp Ser Tyr Ser Glu Ser Asp Val Lys Asp Tyr Leu
            340                 345                 350

Trp Gln Met Leu Ser Ala Thr Gln Tyr Leu His Ala Gln His Ile Leu
        355                 360                 365

His Leu Asp Leu Arg Ser Glu Asn Met Met Val Thr Glu Tyr Asn Leu
    370                 375                 380

Leu Lys Val Ile Asp Leu Gly Asn Ala Gln Ser Leu Ser Gln Glu Lys
385                 390                 395                 400

Val Pro Pro Glu Asn Phe Lys Asp Tyr Leu Glu Thr Met Ala Pro
                405                 410                 415

Glu Leu Glu Gly Gln Gly Ala Val Pro Gln Thr Asp Ile Trp Ala
            420                 425                 430

Ile Gly Val Thr Ala Phe Ile Met Leu Ser Gly Glu Tyr Pro Val Ser
        435                 440                 445

Ser Glu Gly Thr Arg Asp Leu Gln Lys Gly Leu Arg Lys Gly Leu Ile
    450                 455                 460

Gln Leu Ser Arg Cys Tyr Ala Gly Leu Ser Gly Gly Ala Val Ala Phe
465                 470                 475                 480

Leu Gln Ser Ser Leu Cys Ala Arg Pro Trp Gly Arg Pro Cys Ala Ser
                485                 490                 495

Thr Cys Leu Gln Cys Gly Trp Leu Thr Glu Glu Gly Pro Thr Gly Ser
            500                 505                 510

Arg Pro Thr Pro Val Thr Phe Pro Thr Ala Arg Leu Arg Ala Phe Val
        515                 520                 525

Arg Glu Arg Glu Lys Arg Arg Ala Leu Leu Tyr Lys Lys His Asn Leu
    530                 535                 540

Ala Gln Val Arg
545

<210> SEQ ID NO 9
<211> LENGTH: 548
<212> TYPE: PRT
<213> ORGANISM: Mus musculus

<400> SEQUENCE: 9

-continued

```
Met Ala His Ile Ser Arg Ile Leu Lys Gly Arg Pro Glu Gly Pro Glu
 1               5                  10                  15

Arg Glu Gly Pro Pro Arg Lys Lys Ala Gly Leu Ala Ser Phe Arg Leu
                20                  25                  30

Ser Gly Leu Lys Gly Arg Asp Gln Ala Pro Ser Phe Leu Arg Glu Leu
            35                  40                  45

Ser Asp Glu Ala Val Val Leu Gly Gln Ser Val Thr Leu Ala Cys Gln
50                      55                  60

Val Leu Ala Gln Pro Thr Ala Gln Ala Thr Trp Ser Lys Asp Gly Val
65                  70                  75                  80

Leu Leu Glu Ser Ser Gly His Leu Leu Ile Ser Ser Thr Leu Lys Asn
                85                  90                  95

Phe Gln Leu Leu Thr Ile Leu Val Val Lys Glu Glu Asp Leu Gly Thr
            100                 105                 110

Tyr Thr Cys Cys Val Ser Asn Pro Leu Gly Thr Ala Val Thr Thr Gly
            115                 120                 125

Val Leu Arg Lys Ala Glu Arg Pro Ser Ser Ser Pro Arg Pro Glu Val
130                 135                 140

Gly Glu Leu Tyr Lys Asp Ala Val Leu Leu Val Trp Lys Pro Val Glu
145                 150                 155                 160

Ser Cys Gly Pro Val Thr Tyr Ile Val Gln Cys Cys Ile Glu Gly Gly
                165                 170                 175

Ser Trp Thr Thr Leu Ala Ser Asp Ile Ser Asp Cys Cys Tyr Leu Thr
            180                 185                 190

Gly Lys Leu Ser Arg Gly Gly Met Tyr Ile Phe Arg Thr Ala Cys Val
            195                 200                 205

Ser Lys Ala Gly Met Gly Pro Tyr Ser Ser Pro Ser Glu Gln Val Leu
210                 215                 220

Leu Gly Gly Pro Asn His Leu Ala Ser Glu Glu Glu Ser Ser Arg Gly
225                 230                 235                 240

Arg Pro Ala Gln Leu Leu Pro Ser Thr Lys Thr Phe Ala Phe Gln Met
                245                 250                 255

Gln Ile Arg Arg Gly Arg Phe Ser Val Val Arg Gln Cys Arg Glu Lys
            260                 265                 270

Ala Ser Gly Arg Ala Leu Ala Ala Lys Ile Val Pro Tyr Gln Pro Glu
            275                 280                 285

Asp Lys Thr Ala Val Leu Arg Glu Tyr Glu Ala Leu Lys Arg Leu His
290                 295                 300

His Pro His Leu Ala Gln Leu His Ala Ala Tyr Leu Ser Pro Arg His
305                 310                 315                 320

Leu Val Leu Ile Leu Glu Leu Cys Ser Gly Pro Glu Leu Leu Pro Ser
                325                 330                 335

Leu Ala Glu Arg Glu Ser Tyr Ser Glu Ser Asp Val Lys Asp Tyr Leu
            340                 345                 350

Trp Gln Met Leu Ser Ala Thr Gln Tyr Leu His Ala Gln His Ile Leu
            355                 360                 365

His Leu Asp Leu Arg Ser Glu Asn Met Met Val Thr Glu Tyr Asn Leu
370                 375                 380

Leu Lys Val Ile Asp Leu Gly Asn Ala Gln Ser Leu Asp Gln Glu Lys
385                 390                 395                 400

Val Pro Ala Pro Glu Asn Phe Lys Asp Tyr Leu Glu Thr Met Ala Pro
                405                 410                 415
```

```
Glu Leu Leu Glu Gly Gln Gly Ala Val Pro Gln Thr Asp Ile Trp Ala
            420                 425                 430
Ile Gly Val Thr Ala Phe Ile Met Leu Ser Gly Glu Tyr Pro Glu Ser
        435                 440                 445
Ser Glu Gly Thr Arg Asp Leu Gln Lys Gly Leu Arg Lys Gly Leu Ile
    450                 455                 460
Arg Leu Ser Arg Cys Tyr Ala Gly Leu Ser Gly Gly Ala Val Ala Phe
465                 470                 475                 480
Leu Gln Ser Ser Leu Cys Ala Gln Pro Trp Gly Arg Pro Cys Ala Ser
            485                 490                 495
Thr Cys Leu Gln Cys Gly Trp Leu Thr Glu Gly Pro Thr Gly Ser
            500                 505                 510
Arg Pro Thr Pro Val Thr Phe Pro Thr Val Arg Leu Arg Ala Phe Val
        515                 520                 525
Arg Glu Arg Glu Lys Arg Arg Ala Leu Leu Tyr Lys Lys His Asn Leu
    530                 535                 540
Ala Gln Val Arg
545

<210> SEQ ID NO 10
<211> LENGTH: 258
<212> TYPE: PRT
<213> ORGANISM: Homo sapiens

<400> SEQUENCE: 10

Ser Phe Tyr Glu Val Lys Glu Glu Ile Gly Arg Gly Val Phe Gly Phe
1               5                   10                  15
Val Lys Arg Val Gln His Lys Gly Asn Lys Ile Leu Cys Ala Ala Lys
            20                  25                  30
Phe Ile Pro Leu Arg Ser Arg Thr Arg Ala Gln Ala Tyr Arg Glu Arg
        35                  40                  45
Asp Ile Leu Ala Ala Leu Ser His Pro Leu Val Thr Gly Leu Leu Asp
    50                  55                  60
Gln Phe Glu Thr Arg Lys Thr Leu Ile Leu Ile Leu Glu Leu Cys Ser
65                  70                  75                  80
Ser Glu Glu Leu Leu Asp Arg Leu Tyr Arg Lys Gly Val Val Thr Glu
            85                  90                  95
Ala Glu Val Lys Val Tyr Ile Gln Gln Leu Val Glu Gly Leu His Tyr
            100                 105                 110
Leu His Ser His Gly Val Leu His Leu Asp Ile Lys Pro Ser Asn Ile
        115                 120                 125
Leu Met Val His Pro Ala Arg Glu Asp Ile Lys Ile Cys Asp Phe Gly
    130                 135                 140
Phe Ala Gln Asn Ile Thr Pro Ala Glu Leu Gln Phe Ser Gln Tyr Gly
145                 150                 155                 160
Ser Pro Glu Phe Val Ser Pro Glu Ile Ile Gln Gln Asn Pro Val Ser
            165                 170                 175
Glu Ala Ser Asp Ile Trp Ala Met Gly Val Ile Ser Tyr Leu Ser Leu
            180                 185                 190
Thr Cys Ser Ser Pro Phe Ala Gly Glu Ser Asp Arg Ala Thr Leu Leu
        195                 200                 205
Asn Val Leu Glu Gly Arg Val Ser Trp Ser Ser Pro Met Ala Ala His
    210                 215                 220
Leu Ser Glu Asp Ala Lys Asp Phe Ile Lys Ala Thr Leu Gln Arg Ala
225                 230                 235                 240
```

```
Pro Gln Ala Arg Pro Ser Ala Ala Gln Cys Leu Ser His Pro Trp Phe
                245                 250                 255

Leu Lys

<210> SEQ ID NO 11
<211> LENGTH: 253
<212> TYPE: PRT
<213> ORGANISM: Homo sapiens

<400> SEQUENCE: 11

Ala Phe Gln Thr Gln Ile Gln Arg Gly Arg Phe Ser Val Val Arg Gln
 1               5                  10                  15

Cys Trp Glu Lys Ala Ser Gly Arg Ala Leu Ala Ala Lys Ile Ile Pro
                20                  25                  30

Tyr His Pro Lys Asp Lys Thr Ala Val Leu Arg Glu Tyr Glu Ala Leu
                35                  40                  45

Lys Gly Leu Arg His Pro His Leu Ala Gln Leu His Ala Ala Tyr Leu
 50                  55                  60

Ala Pro Arg His Leu Val Leu Ile Leu Glu Leu Cys Ser Gly Pro Glu
65                   70                  75                  80

Leu Leu Pro Cys Leu Ala Glu Arg Ala Ser Tyr Ser Glu Ser Glu Val
                85                  90                  95

Lys Asp Tyr Leu Trp Gln Met Leu Ser Ala Thr Gln Tyr Leu His Asn
                100                 105                 110

Gln His Ile Leu His Leu Asp Leu Arg Ser Glu Asn Met Ile Ile Thr
                115                 120                 125

Glu Tyr Asn Leu Leu Lys Val Val Asp Leu Gly Asn Ala Gln Ser Leu
130                 135                 140

Ser Gln Glu Lys Val Leu Pro Ser Asp Lys Phe Lys Asp Tyr Leu Glu
145                 150                 155                 160

Thr Met Ala Pro Glu Leu Leu Glu Gly Gln Gly Ala Val Pro Gln Thr
                165                 170                 175

Asp Ile Trp Ala Ile Gly Val Thr Ala Phe Ile Met Leu Ser Ala Glu
                180                 185                 190

Tyr Pro Val Ser Ser Glu Gly Ala Arg Asp Leu Gln Arg Gly Leu Arg
                195                 200                 205

Lys Gly Leu Val Arg Leu Ser Arg Cys Tyr Ala Gly Leu Ser Gly Gly
                210                 215                 220

Ala Val Ala Phe Leu Arg Ser Thr Leu Cys Ala Gln Pro Trp Gly Arg
225                 230                 235                 240

Pro Cys Ala Ser Ser Cys Leu Gln Cys Pro Trp Leu Thr
                245                 250

<210> SEQ ID NO 12
<211> LENGTH: 258
<212> TYPE: PRT
<213> ORGANISM: Homo sapiens

<400> SEQUENCE: 12

Ser Phe Tyr Ser Glu Val Ala Glu Leu Gly Arg Gly Arg Phe Ser Val
 1               5                  10                  15

Val Lys Lys Cys Asp Gln Lys Gly Thr Lys Arg Ala Val Ala Thr Lys
                20                  25                  30

Phe Val Asn Lys Lys Leu Met Lys Arg Asp Gln Val Thr His Glu Leu
                35                  40                  45
```

-continued

Gly Ile Leu Gln Ser Leu Gln His Pro Leu Leu Val Gly Leu Leu Asp
 50                  55                  60

Thr Phe Glu Thr Pro Thr Ser Tyr Ile Leu Val Leu Glu Met Ala Asp
 65                  70                  75                  80

Gln Gly Arg Leu Leu Asp Cys Val Val Arg Trp Gly Ser Leu Thr Glu
                 85                  90                  95

Gly Lys Ile Arg Ala His Leu Gly Glu Val Leu Glu Ala Val Arg Tyr
             100                 105                 110

Leu His Asn Cys Arg Ile Ala His Leu Asp Leu Lys Pro Glu Asn Ile
             115                 120                 125

Leu Val Asp Glu Ser Leu Ala Lys Pro Thr Ile Lys Leu Ala Asp Phe
130                 135                 140

Gly Asp Ala Val Gln Leu Asn Thr Thr Tyr Tyr Ile His Gln Leu Leu
145                 150                 155                 160

Gly Asn Pro Glu Phe Ala Ala Pro Glu Ile Ile Leu Gly Asn Pro Val
                165                 170                 175

Ser Leu Thr Ser Asp Thr Trp Ser Val Gly Val Leu Thr Tyr Val Leu
            180                 185                 190

Leu Ser Gly Val Ser Pro Phe Leu Asp Asp Ser Val Glu Glu Thr Cys
            195                 200                 205

Leu Asn Ile Cys Arg Leu Asp Phe Ser Phe Pro Asp Asp Tyr Phe Lys
210                 215                 220

Gly Val Ser Gln Lys Ala Lys Glu Phe Val Cys Phe Leu Leu Gln Glu
225                 230                 235                 240

Asp Pro Ala Lys Arg Pro Ser Ala Ala Leu Ala Leu Gln Glu Gln Trp
                245                 250                 255

Leu Gln

<210> SEQ ID NO 13
<211> LENGTH: 256
<212> TYPE: PRT
<213> ORGANISM: Homo sapiens

<400> SEQUENCE: 13

Tyr Asp Ile Glu Glu Arg Leu Gly Ser Gly Lys Phe Gly Gln Val Phe
 1               5                  10                  15

Arg Leu Val Glu Lys Lys Thr Gly Lys Ile Trp Ala Gly Lys Phe Phe
                 20                  25                  30

Lys Ala Tyr Ser Ala Lys Glu Lys Glu Asn Ile Pro Ala Glu Ile Gly
             35                  40                  45

Ile Met Asn Cys Leu His His Pro Lys Leu Val Gln Cys Val Asp Ala
 50                  55                  60

Phe Glu Glu Lys Ala Asn Ile Val Met Val Leu Glu Ile Val Ser Gly
 65                  70                  75                  80

Gly Glu Leu Phe Glu Arg Ile Ile Asp Glu Asp Phe Glu Leu Thr Glu
                 85                  90                  95

Arg Glu Cys Ile Lys Tyr Met Arg Gln Ile Ser Glu Gly Val Glu Tyr
             100                 105                 110

Ile His Lys Gln Gly Ile Val His Leu Asp Leu Lys Pro Glu Asn Ile
             115                 120                 125

Met Cys Val Asn Lys Thr Gly Thr Arg Ile Lys Leu Ile Asp Phe Gly
130                 135                 140

Leu Ala Arg Arg Leu Glu Asn Ala Gly Ser Leu Lys Val Leu Phe Gly
145                 150                 155                 160

-continued

Thr Pro Glu Phe Val Ala Pro Glu Val Ile Asn Tyr Glu Pro Ile Ser
                165                 170                 175

Tyr Ala Thr Asp Met Trp Ser Ile Gly Val Ile Cys Tyr Ile Leu Val
            180                 185                 190

Ser Gly Leu Ser Pro Phe Met Gly Asp Asn Asp Asn Glu Thr Leu Ala
            195                 200                 205

Asn Val Thr Ser Ala Thr Trp Asp Phe Asp Asp Glu Ala Phe Asp Glu
        210                 215                 220

Ile Ser Asp Asp Ala Lys Asp Phe Ile Ser Asn Leu Leu Lys Lys Asp
225                 230                 235                 240

Met Lys Asn Arg Leu Asp Cys Thr Gln Cys Leu Gln His Pro Trp Leu
                245                 250                 255

<210> SEQ ID NO 14
<211> LENGTH: 180
<212> TYPE: PRT
<213> ORGANISM: Homo sapiens

<400> SEQUENCE: 14

Val Ile Gln Glu Leu Leu Ser Ser Glu Gln Ala Phe Val Glu Glu Leu
1               5                   10                  15

Gln Phe Leu Gln Ser His His Leu Gln His Leu Glu Arg Cys Pro His
                20                  25                  30

Val Pro Ile Ala Val Ala Gly Gln Lys Ala Val Ile Phe Arg Asn Val
            35                  40                  45

Arg Asp Ile Gly Arg Phe His Ser Ser Phe Leu Gln Glu Leu Gln Gln
        50                  55                  60

Cys Asp Thr Asp Asp Asp Val Ala Met Cys Phe Ile Lys Asn Gln Ala
65                  70                  75                  80

Ala Phe Glu Gln Tyr Leu Glu Phe Leu Val Gly Arg Val Gln Ala Glu
                85                  90                  95

Ser Val Val Val Ser Thr Ala Ile Gln Glu Phe Tyr Lys Lys Tyr Ala
                100                 105                 110

Glu Glu Ala Leu Leu Ala Gly Asp Pro Ser Gln Pro Pro Pro Pro Pro
            115                 120                 125

Leu Gln His Tyr Leu Glu Gln Pro Val Glu Arg Val Gln Arg Tyr Gln
        130                 135                 140

Ala Leu Leu Lys Glu Leu Ile Arg Asn Lys Ala Arg Asn Arg Gln Asn
145                 150                 155                 160

Cys Ala Leu Leu Glu Gln Ala Tyr Ala Val Val Ser Ala Leu Pro Gln
                165                 170                 175

Arg Ala Glu Asn
            180

<210> SEQ ID NO 15
<211> LENGTH: 171
<212> TYPE: PRT
<213> ORGANISM: Homo sapiens

<400> SEQUENCE: 15

Ile Met Ala Glu Leu Ile Gln Thr Glu Lys Ala Tyr Val Arg Asp Leu
1               5                   10                  15

Arg Glu Cys Met Asp Thr Tyr Leu Trp Glu Met Thr Ser Gly Val Glu
                20                  25                  30

Glu Ile Pro Pro Gly Ile Val Asn Lys Glu Leu Ile Ile Phe Gly Asn
            35                  40                  45

```
Met Gln Glu Ile Tyr Glu Phe His Asn Asn Ile Phe Leu Lys Glu Leu
        50                  55                  60

Glu Lys Tyr Glu Gln Leu Pro Glu Asp Val Gly His Cys Phe Val Thr
 65                  70                  75                  80

Trp Ala Asp Lys Phe Gln Met Tyr Val Thr Tyr Cys Lys Asn Lys Pro
                85                  90                  95

Asp Ser Thr Gln Leu Ile Leu Glu His Ala Gly Ser Tyr Phe Asp Glu
            100                 105                 110

Ile Gln Gln Arg His Gly Leu Ala Asn Ser Ile Ser Ser Tyr Leu Ile
            115                 120                 125

Lys Pro Val Gln Arg Ile Thr Lys Tyr Gln Leu Leu Leu Lys Glu Leu
        130                 135                 140

Leu Thr Cys Cys Glu Glu Gly Lys Gly Glu Ile Lys Asp Gly Leu Glu
145                 150                 155                 160

Val Met Leu Ser Val Pro Lys Arg Ala Asn Asp
                165                 170

<210> SEQ ID NO 16
<211> LENGTH: 172
<212> TYPE: PRT
<213> ORGANISM: Homo sapiens

<400> SEQUENCE: 16

Val Leu Gln Glu Leu Val Glu Thr Glu Arg Asp Tyr Val Arg Asp Leu
  1               5                  10                  15

Gly Tyr Val Val Glu Gly Tyr Met Ala Leu Met Lys Glu Asp Gly Val
                 20                  25                  30

Pro Asp Asp Met Lys Gly Lys Asp Lys Ile Val Phe Gly Asn Ile His
                35                  40                  45

Gln Ile Tyr Asp Trp His Arg Asp Phe Phe Leu Gly Glu Leu Glu Lys
         50                  55                  60

Cys Leu Glu Asp Pro Glu Lys Leu Gly Ser Leu Phe Val Lys His Glu
 65                  70                  75                  80

Arg Arg Leu His Met Tyr Ile Ala Tyr Cys Gln Asn Lys Pro Lys Ser
                85                  90                  95

Glu His Ile Val Ser Glu Tyr Ile Asp Thr Phe Phe Glu Asp Leu Lys
            100                 105                 110

Gln Arg Leu Gly His Arg Leu Gln Leu Thr Asp Leu Leu Ile Lys Pro
            115                 120                 125

Val Gln Arg Ile Met Lys Tyr Gln Leu Leu Leu Lys Asp Phe Leu Lys
        130                 135                 140

Tyr Ser Lys Lys Ala Ser Leu Asp Thr Ser Glu Leu Glu Arg Ala Val
145                 150                 155                 160

Glu Val Met Cys Ile Val Pro Arg Arg Cys Asn Asp
                165                 170

<210> SEQ ID NO 17
<211> LENGTH: 103
<212> TYPE: PRT
<213> ORGANISM: Homo sapiens

<400> SEQUENCE: 17

Val Trp Glu Gly Ala Pro Gly Ala Arg Met Pro Trp Lys Gly His Asn
  1               5                  10                  15

Arg His Val Phe Leu Phe Arg Asn His Leu Val Ile Cys Lys Pro Arg
                 20                  25                  30
```

-continued

```
Arg Asp Ser Arg Thr Asp Thr Val Ser Tyr Val Phe Arg Asn Met Met
        35              40              45

Lys Leu Ser Ser Ile Asp Leu Asn Asp Gln Val Glu Gly Asp Asp Arg
    50              55              60

Ala Phe Glu Val Trp Gln Glu Arg Glu Asp Ser Val Arg Lys Tyr Leu
65              70              75              80

Leu Gln Ala Arg Thr Ala Ile Ile Lys Ser Ser Trp Val Lys Glu Ile
            85              90              95

Cys Gly Ile Gln Gln Arg Leu
            100
```

MEDIATORS OF SIGNAL TRANSDUCTION

The present application claims benefit of the priority of provisional application of Ser. Nos. 60/129,553 filed on Apr. 16, 1999, now abandoned.

FIELD OF THE INVENTION

The present invention relates to compounds and methods for the identification, prevention or treatment of disease, preferably cardiac disease, in a mammal through the administration of polypeptides capable of regulating signal transduction, which preferably exhibit kinase activity, or antibodies against such polypeptides that inhibit the interaction of these polypeptides with other mediators of signal transduction. In addition, the compounds and methods of the present invention can facilitate the identification or isolation of additional mediators of signal transduction associated with disease, preferably cardiac disease, which in turn may also be used in the identification, prevention or treatment of disease, preferably cardiac disease, in mammals.

BACKGROUND OF THE INVENTION

Certain biological functions, such as growth and differentiation, are tightly regulated by signal transduction pathways within cells. Signal transduction pathways maintain the balanced steady state functioning of a cell. Disease states can arise when signal transduction in a cell breaks down, thereby removing the control that typically exists over cellular functions. Because signal transduction networks regulate a multitude of cellular functions depending upon the cell type, a wide variety of diseases can result from abnormalities in such networks. Devastating diseases such as cancer, autoimmune diseases, allergic reactions, inflammation, neurological disorders and hormone-related diseases can result from abnormal signal transduction. For example, tumors may develop when regulation of cell growth is disrupted.

Despite a long-felt need to understand and discover methods for regulating cells involved in various disease states, the complexity of signal transduction pathways has precluded the development of products and processes for regulating cellular function by manipulating signal transduction pathways in a cell. As such, there remains a need for products and processes that permit the implementation of predictable controls of signal transduction in cells, thus enabling the treatment of various diseases that are caused by abnormal cellular function.

Such diseases may include cardiac diseases, which may include congestive heart failure (CHF), dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors. By way of example, CHF is a major cardiac disease associated with extensive morbidity and mortality. Approximately five million individuals in the United States suffer from some form of CHF. Traditionally, treatment of CHF occurs by a series of agents including diuretics, vasodilators, angiotensin converting enzyme inhibitors, β-adrenergic antagonists, and positive inotropes like digoxin. These drugs, however, principally provide symptomatic relief and typically only extend the life of one suffering from the disease for periods ranging from 6–12 months.

The pathophysiology of CHF is rather complex. Generally, the central hallmark of the disease is the inability of the heart to pump sufficient oxygenated blood to meet the demands of peripheral tissues. Numerous etiologies contribute to the development of CHF, including primary diseases of, or insults to, the myocardium itself, cardiac defects, hypertension, inflammation, kidney disease and vascular disease. These conditions lead to the hypertrophy and remodeling of the cardiac ventricles which, if unchecked, ultimately reduce the mechanical performance of the heart. Forces associated with the inability of the heart to pump blood ultimately lead to the release of neurohormones like catecholamines, renin-angiotensin, aldosterone, endothelin and related factors into the circulation. Elevations in plasma levels of many of these circulating neurohormones have a deleterious impact on the outcome of patients with CHF. Local production of these neurohormonal factors in the heart is believed to contribute centrally to the disease. Thus, an important therapeutic strategy has been to block this neurohormonal axis contributing to the pathogenesis of this disease.

Factors known to contribute centrally to the pathophysiology of heart disease are biosynthesized in the heart itself. These factors are produced in cardiac myocytes, fibroblasts, smooth muscle and endothelial cells, and inflammatory cells associated with the myocardium. For example, the heart contains its own renin-angiotensin system. Blockade of the cardiac renin-angiotensin system may contribute significantly to the therapeutic efficacy of the therapeutic class of agents known as angiotensin converting enzyme (ACE) inhibitors.

The heart also produces other factors including endothelins, bradykinin, adrenomedullin, tumor necrosis factor, transforming growth factors, and natriuretic peptides. Unfortunately, therapeutic strategies are limited to the modulation of such substances, which are already known to contribute to the disease. Indeed, the fictional contributions of only a minor fraction of all known secreted factors encoded by the human genome have apparently been defined.

The foregoing shows a need for methods and products involving the prevention or treatment of disease in mammals involving the mediation of signal transduction. The administration of polypeptides capable of regulating signal transduction, which preferably exhibit kinase activity, or antibodies against such polypeptides that inhibit the interaction of these polypeptides with other mediators of signal transduction, in addition to the identification or isolation of additional mediators of signal transduction associated with disease, preferably cardiac disease, which in turn may also be used in the identification, prevention or treatment of disease, preferably cardiac disease, in mammals, can facilitate such prevention or treatment.

SUMMARY OF THE INVENTION

An objective of the present invention is therefore the prevention or treatment of disease, preferably cardiac disease, in mammals through the administration of polypeptides capable of regulating signal transduction, which preferably exhibit kinase activity, or antibodies against such polypeptides that inhibit the interaction of these polypeptides with other mediators of signal transduction, in addition to the identification or isolation of additional mediators of signal transduction associated with disease, preferably cardiac disease, which in turn may also be used in the identification, prevention or treatment of disease, preferably cardiac disease, in mammals.

In accomplishing these and other objectives, the present invention preferably provides a purified polypeptide comprising the amino acid sequence of SEQ ID NOS: 1, 4, 6, 7, 8 or 9 wherein the polypeptide is capable of regulating signal transduction. In a preferred embodiment, the polypeptide is capable of catalyzing the transfer of a phosphate group from a donor molecule to an acceptor molecule.

In another embodiment, the present invention preferably provides an isolated DNA molecule encoding a purified polypeptide comprising the amino acid sequence of SEQ ID NOS: 1, 4, 6, 7, 8 or 9 wherein the polypeptide is capable of regulating signal transduction. The present invention may also preferably be an isolated DNA molecule comprising the nucleotide sequence of SEQ ID NOS: 2, 3 or 5.

In yet another embodiment, the present invention preferably provides a vector comprising a DNA molecule encoding a purified polypeptide comprising the amino acid sequence of SEQ ID NOS: 1, 4, 6, 7, 8 or 9 wherein the polypeptide is capable of regulating signal transduction. In another aspect, the present invention provides a host cell transformed with such a vector. In one other embodiment, the present invention may preferably provide the above-described transformed host cell, where the host cell produces a polypeptide capable of regulating signal transduction. In a preferred embodiment, the above-described transformed host cell produces a polypeptide capable of catalyzing the transfer of a phosphate group from a donor molecule to an acceptor molecule.

In another preferred embodiment, the present invention provides an isolated antibody against a polypeptide comprising the amino acid sequence of SEQ ID NOS: 1, 4, 6, 7, 8 or 9 wherein the polypeptide is capable of regulating signal transduction. In a preferred embodiment, the antibody is a monoclonal antibody. In another preferred embodiment, the antibody is capable of inhibiting the regulation of signal transduction. In yet another preferred embodiment, the antibody is capable of inhibiting the transfer of a phosphate group from a donor molecule to an acceptor molecule.

The present invention may also preferably provide an isolated nucleic acid capable of hybridizing under high stringency conditions to a DNA molecule comprising the nucleotide sequence of SEQ ID NOS: 2, 3 or 5. In a preferred embodiment, this isolated nucleic acid is capable of inhibiting the regulation of signal transduction. In yet another preferred embodiment, this isolated nucleic acid is capable of inhibiting said transfer of said phosphate group from said donor molecule to said acceptor molecule.

In a preferred embodiment, the present invention provides a method of preventing or treating disease in a mammal comprising administering to said mammal an effective amount of material, selected from the group consisting of the polypeptide comprising the amino acid sequence of SEQ ID NOS: 1, 4, 6, 7, 8 or 9 wherein the polypeptide is capable of regulating signal transduction, and the antibody against this polypeptide, in a pharmaceutically acceptable sterile vehicle. In a preferred embodiment, the mammal may be a human. In another, the disease may he cardiac disease.

The present invention may also preferably provide a vaccine for preventing disease in a mammal comprising administering to said mammal an effective amount of material, selected from the group consisting of the polypeptide comprising the amino acid sequence of SEQ ID NOS: 1, 4, 6, 7, 8 or 9 wherein the polypeptide is capable of regulating signal transduction, and the antibody against this polypeptide, in a pharmaceutically acceptable sterile vehicle. In a preferred embodiment, the mammal may be a human. In another, the disease may be cardiac disease.

In a preferred embodiment, the present invention provides a method of preventing or treating disease in a mammal comprising administering to said mammal syngeneic cells transformed with a vector comprising a DNA molecule encoding a purified polypeptide comprising the amino acid sequence of SEQ ID NOS: 1, 4, 6, 7, 8 or 9 wherein the polypeptide is capable of regulating signal transduction, and wherein the transformed syngeneic cells produce a polypeptide capable of regulating signal transduction. In a preferred embodiment, the mammal may be a human. In another, the disease may be cardiac disease.

The present invention may also preferably provide a method of preventing or treating disease in a mammal comprising administering to said mammal syngeneic cells transformed with a vector comprising a DNA molecule encoding a purified polypeptide comprising the amino acid sequence of SEQ ID NOS: 1, 4, 6, 7, 8 or 9 wherein the polypeptide is capable of regulating signal transduction, and wherein the transformed syngeneic cells produce a polypeptide capable of catalyzing the transfer of a phosphate group from a donor molecule to an acceptor molecule. In a preferred embodiment, the mammal may be a human. In another, the disease may be cardiac disease.

In a preferred embodiment, the present invention may provide a kit for detecting the expression of a protein capable of regulating signal transduction, comprising a polypeptide, which comprises the amino acid sequence of SEQ ID NOS: 1, 4, 6, 7, 8 or 9 wherein the polypeptide is capable of regulating signal transduction. In a preferred embodiment, this kit further comprises a detectable label selected from the group consisting of colorimetric, enzymatic, chemiluminescent, fluorescent and radioactive labels.

In another preferred embodiment, the present invention may provide a kit for detecting the expression of a protein capable of acting as a donor molecule or an acceptor molecule of a phosphate group comprising a polypeptide, which comprises the amino acid sequence of SEQ ID NOS: 1, 4, 6, 7, 8 or 9 wherein the polypeptide is capable of regulating signal transduction. In a preferred embodiment, this kit further comprises a detectable label selected from the group consisting of colorimetric, enzymatic, chemiluminescent, fluorescent and radioactive labels.

The present invention may also preferably provide a method for detecting the expression of a protein capable of regulating signal transduction, comprising contacting a sample with a polypeptide, which comprises the amino acid sequence of SEQ ID NOS: 1, 4, 6, 7, 8 or 9 wherein the polypeptide is capable of regulating signal transduction, and detecting any effect of the sample on an indicator of signal transduction. In a preferred embodiment, the polypeptide is immobilized to a solid support. In another preferred embodiment, the phosphate group is detectably labeled.

In another preferred embodiment, the present invention may provide a method for detecting the expression of a protein capable of acting as a donor molecule or an acceptor molecule of a phosphate group, comprising contacting a sample with a polypeptide, which comprises the amino acid sequence of SEQ ID NOS: 1, 4, 6, 7, 8 or 9 wherein the polypeptide is capable of regulating signal transduction, and detecting any effect of the sample on an indicator of signal transduction, and detecting any transfer of the phosphate group. In a preferred embodiment, the polypeptide is immobilized to a solid support. In another preferred embodiment, the phosphate group is detectably labeled.

Other objectives, features, and advantages of the present invention will become apparent from the following detailed description. The detailed description and the specific examples, while indicating preferred embodiments of the invention, are provided by way of illustration only. Accordingly, the present invention also includes those various changes and modifications within the spirit and scope of the invention that may become apparent to those skilled in the art from this detailed description.

BRIEF DESCRIPTION OF THE FIGURES

FIGS. 2A–E depicts homology alignment of amino acid sequences of human (SEQ ID NO: 7), rat (SEQ ID NO: 8) and mouse (SEQ ID NO: 9) clones corresponding to 19G5.

FIGS. 6A–B is the sequence comparison of the kinase domains of H19G5 (N-terminal (SEQ ID NO: 10) and C-terminal kinase domains (SEQ ID NO: 11)), Trio (SEQ ID NO: 12), and smooth muscle myosin light chain (SM MLCK) (SEQ ID NO: 13).

FIG. 7 is the sequence comparison of the guanine nucleotide exchange factor (GEF) domains of H19G5 (SEQ ID NO: 14) and Trio (SEQ ID NOs: 15 and 16).

FIG. 8 shows the subcellular localization of 19G5-GFP fusion proteins in mouse myoblast cell line C2C12. Three 19G5-GFP fusion protein expression constructs were made using three different 19G5 cDNA clones, the longest human 19G5 clone C11 [h19G5(C11)-GFP], a 2.7 kb clone of human 19G5 containing the C-terminal kinase domain [h19G59)-GFP], and the rat 19G5 small transcript [r19G5 (S)-GFP]. The control GFP vector and the 19G5-GFP fusion expression constructs were transfected into C2C12 cells. The 19G5-GFP proteins' localization was detected using confocal microscopy.

DETAILED DESCRIPTION OF THE PREFERRED EMBODIMENTS

Figure 1:
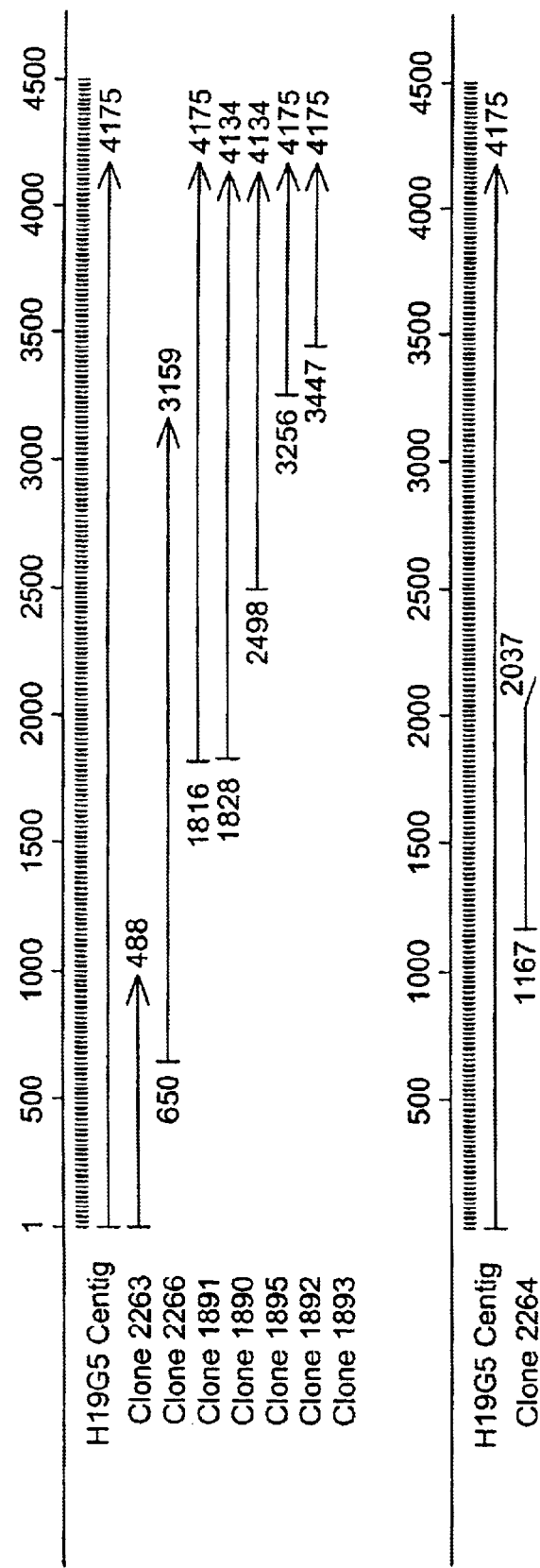
FIG. 1 illustrates eight overlapping human cDNA clones of 19G5.

Those skilled in the art will recognize that the products and methods embodied in the present invention may be applied to a variety of systems, constructed with various materials using various methods. Accordingly, the present invention is not limited to any particular environment, and the following description of specific embodiments of the present invention are for illustrative purposes only.

The present invention preferably provides methods for the prevention or treatment of disease, preferably cardiac disease, in mammals through the administration of polypeptides capable of regulating signal transduction, which preferably exhibit kinase activity, or antibodies against such polypeptides that inhibit the interaction of these polypeptides with other mediators of signal transduction, in addition to the identification or isolation of additional mediators of signal transduction associated with disease, preferably cardiac disease, which in turn may also be used in the identification, prevention or treatment of disease, preferably cardiac disease, in mammals. The cardiac diseases according to the present invention may include congestive heart failure (CHF), dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors.

An embodiment of the invention is a purified polypeptide comprising an amino acid sequence having at least 95% sequence identity with the amino acid sequence of SEQ ID NOS: 1, 4, 6, 7, 8 or 9. As used herein, polypeptide refers to a linear series of amino acid residues connected to one another by peptide bonds between the alpha-amino groups and carboxy groups of adjacent amino acid residues. Additional covalent bonds between portions of the peptide may also be present to restrain the conformation of the molecule, such as amide and disulfide bonds. When used herein, polypeptide also refers to a linear series of amino acid residues connected one to the other as in a peptide. The term synthetic peptide means a chemically derived chain of amino acid residues linked together by peptide bonds that is free of naturally occurring proteins and fragments thereof.

The one and three-letter symbols used to represent the amino acid residues in the polypeptides of the present invention are those symbols commonly-used in the art. The amino acid residues are preferred to be in the L isomeric form. However, residues in the D isomeric form may be substituted for any L-amino acid, as long as the desired fictional property of signal transduction mediation is retained by the peptide. The one and three-letter symbols used herein refer to the following amino acids: Ser (S) is serine; Ile (I) is isoleucine; Gln (Q) is glutamine; Phe (F) is phenylalanine; His (H) is histidine; Trp (W) is tryptophan; Lys (K) is lysine; Asn (N) is asparagine; Leu (L) is leucine; Gly (G) is glycine; Thr (T) is threonine; Asp (D) is aspartic acid; Arg (R)is arginine; and Ala (A) is alanine.

Polypeptides of the present invention include variants, fragments and chemical derivatives of the polypeptides comprising the amino acid sequence of SEQ ID NOS: 1, 4, 6, 7, 8 or 9 as long as they are capable of mediating signal transduction. Polypeptides thus may include soluble peptides, Ig-tailed fusion peptides (including immunoadhesions), members of random peptide libraries (see, e.g., Lamn, K. S. et al., Nature 354:82–84 (1991); Houghten, R. et al., Nature 354:84–86 (1991)), combinatorial chemistry-derived molecular libraries made of D- and/or L-configuration amino acids, and phosphopeptides (including members of random or partially degenerate, directed phosphopeptide libraries, see, e.g., Songyang, Z. et al., Cell 72:767–778(1993)).

Polypeptides of the present invention may also include polypeptides that can be isolated from nature or can be produced by recombinant and/or synthetic means. Such native sequence polypeptides specifically refers to naturally-occurring truncated or secreted forms (e.g., an extracellular domain sequence), as well as naturally occurring variant forms (e.g., alternatively spliced forms), and naturally occurring allelic variants of the named polypeptides.

The term variant refers to any polypeptide having an amino acid sequence, in comparison to the amino acid sequences of the polypeptides of the present invention, in which one or more amino acids have been substituted with other amino acids; where the substituted amino acids allow or require the polypeptide to assume the equilibrium conformation of the domain of the parent protein. Often, cysteine, lysine and glutamic acid will be used for their side chains which can form covalent linkages to restrict the conformation of a peptide. The term variant refers to any polypeptide in which one or more amino acids are added and/or substituted and/or deleted and/or inserted at the N- or C-terminus or anywhere within the corresponding native sequence, and which retains signal transduction mediation activity of the corresponding native polypeptide. The variants herein preferably comprise a sequence that has at least about 80% sequence identity, more preferably at least about 85% sequence identity, even more preferably at least about 90% sequence identity, most preferably at least about 95% sequence identity, with the amino acid sequence of SEQ ID NOS: 1, 4, 6, 7, 8 or 9.

In such amino acid sequences, one or more amino acids in the fundamental sequence may preferably be substituted with another amino acid(s), the charge and polarity of which is similar to that of the native amino acid, i.e., a conservative amino acid substitution, resulting in a silent change. Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

The term variant shall also include any polypeptide having one or more amino acids deleted from or added to an amino acid sequence of a mediator of signal transduction, but which still retains signal transduction mediation activity. The term fragment shall refer to any shorter version of the polypeptides herein, wherein the fragment is capable of mediating signal transduction.

Sequence identity is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values are preferably generated by the NCBI BLAST2.0 software as defined by Altschul et al., (1997), "Gapped BLAST and PSI-BLAST: a new generation of protein database search programs", *Nucleic Acids Res.*, 25:3389–3402. The parameters are set to default values, with the exception of the Penalty for mismatch, which is set to −1. Other algorithms, such as GAP, BESTFIT, FASTA, and TFASTA in the Wisconsin Genetics Software Package (Genetics Computer Groups, 575 Science Dr., Madison, Wis.), are also suitable. The selection of the non-default parameters to achieve maximum sequence identity is well within the skill of a person skilled in the art.

Antibodies of the present invention may include any polyclonal, monoclonal, humanized, anti-idiotypic, chimeric or single chain antibodies, and FAb, F(ab')$_2$ and FAb fragments, and epitope-binding fragments thereof.

Without further elaboration, one skilled in the art with the preceding description can utilize the present invention to its fullest extent. The following examples are illustrative only, and not intended to limit the remainder of the disclosure in any way.

EXAMPLE 1

Isolation and Characterization of 19G5 Clones from Rat, Mouse and Human

Isolation of Partial and Full-length 19G5 Clones from Rat Mouse and Human

Microarray technology was used to identify genes that are differentially expressed in normal and diseased rat heart. A sequence designated as 19G5 was down regulated in 12-week myocardial infarct (MI) rat hearts. A rat cDNA clone corresponding to 19G5 (R19G5) was isolated and nucleotide sequence determined. The deduced amino acid sequence of the clone revealed homology to the catalytic domain of kinases, thus suggesting that the protein product of R19G5 might be involved in signal transduction. A hybridization of multiple tissue Northern blot with the R19G5 probe showed that the gene is highly expressed in heart as a 2 kb and 4.4 kb transcripts (FIG. 8).

A full length cDNA for the 2 kb R19G5 transcript was cloned using 5' RACE technique. The R19G5 has an open reading frame of 1644 base pairs which encodes a protein of 548 amino acids (SEQ ID NO: 8)

A mouse 19G5 (N19G5) EST clone was identified by searching the EST database. Northern blot hybridization using the M19G5 EST clone as probe detected a major transcript of 2 kb in heart. There is also a low level of expression in lung. The smeary hybridization was also detected as in the rat and human but was less prominent. M19G5 was also expressed in 17-day old mouse embryos suggesting that it may play a role in embryo development. Sequence analysis of the M19G5 clone showed that it is 1900 base pairs long and has an open reading frame of 1644 base pairs coding for a polypeptide of 548 amino acids (SEQ ID NO: 9), suggesting that it likely represents full length 2 kb transcript.

A number of human cDNA clones corresponding to 19G5 (H19G5) were isolated from human cDNA library using, R19G5 as a probe. FIG. 1 shows eight overlapping cDNA clones of H19G5. Extensive overlap among these clones helped build a consensus nucleotide sequence (SEQ ID NO: 2) designated as H19G5 contig. The sequence corresponds to a major transcript (~5 kb) expressed in human heart. The sequence of the contig revealed that it is complete at the 3'-end since it contains a polyadenylation signal (AATAAA) as well as polyA residues at the 3'-end. It has a potential open reading frame, coding for 1351 amino acid residues, that extends beyond the 5'-end of the contig indicating that it is incomplete at the 5'-end. The deduced amino acid sequence (SEQ ID NO: 1) revealed a protein kinase domain at the C-terminal end (amino acid residues 1056 to 1309) and also a partial protein kinase domain towards the N-terminal end (amino acid residues 1 to 105) of this truncated clone. The sequence information of this contig (SEQ ID NO: 2) was used to devise antisense primers corresponding to the 5'-end, which were used in 5' RACE (rapid amplification of cDNA ends) to isolate cDNA clones with longer inserts. A cDNA clone containing full-length coding sequence was isolated. The nucleotide sequence of the clone (SEQ ID NO: 3) revealed an open reading frame that could potentially code for 1667 amino acids long full-length polypeptide (SEQ ID NO: 4).

Using the 5' RACE technique, the full coding region for one of the larger H19G5 (3 kb or 5 kb) transcripts was cloned. It has an open reading frame of 2613 base pairs encoding a protein of 811 amino acids.

FIG. 2 shows the amino acid sequence aligiunent of the three full-length 19G5 proteins. Both the R19G5 (SEQ ID NO: 8) and M19G5 (SEQ ID NO: 9) proteins overlap with the C-terminal two-third of a splicing variant of the H19G5 protein (SEQ ID NO: 7). The identity between the R19G5 and M19G5 proteins is 97%. The three proteins are 85% identical in their sequences.

Figure 3:
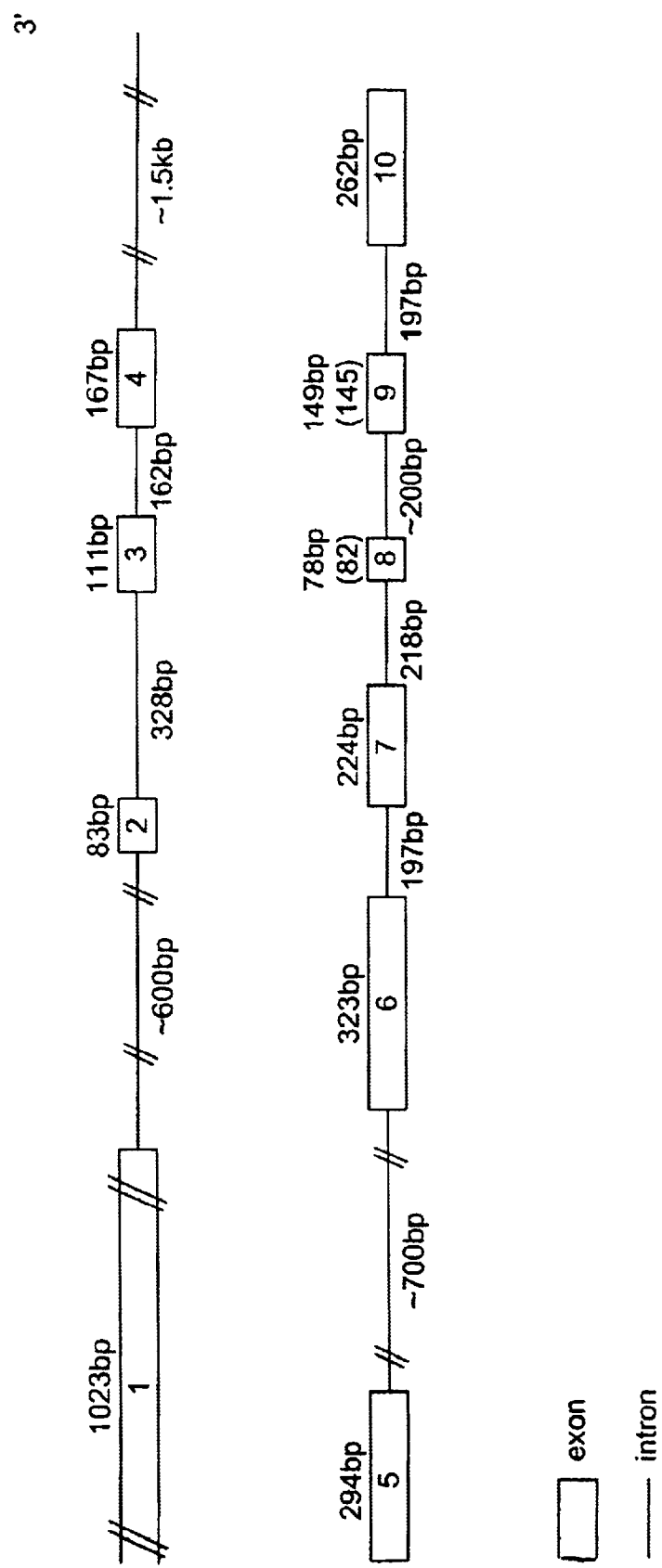
FIG. 3 depicts the likely gene structure of human 19G5 (H19G5), which reveals at least 10 exons and 9 introns.

In order to understand the genomic organization of H19G5 gene, phage genomic library was screened and eleven H19G5 genomic clones were isolated. Restriction enzyme mapping of these clones detected no polymorphism, suggesting that H19G5 may be a single copy gene. The entire genomic DNA region encompassing H19G5 was sequenced and found to contain at least 10 exons and 9 introns as shown in FIG. 3.

One of the H19G5 cDNA clones contained deletion of two amino acid residues (alanine and proline) in the kinase domain. Sequence analysis of the genomic H19G5 DNA revealed an intron located immediately upstream of the alanine residue. There are two adjacent splicing acceptor sites that are four nucleotides apart at the 3' end of the intron. A splicing event using the first acceptor site generates a protein that includes the two residues, alanine and proline. Utilization of the second splicing acceptor site creates a H19G5 protein with the two amino acids deleted in its kinase domain. These two residues are highly conserved among all kinases. This deletion form of H19G5 protein may thus exhibit reduced or no kinase activity at all, and may serve as a dominant negative inhibitor of the kinase activity of H19G5. This provides a possible mechanism to regulate the activity of H19G5 in vivo.

Isolation of cDNA Clones of Splicing Variants of H19G5

Figure 4:
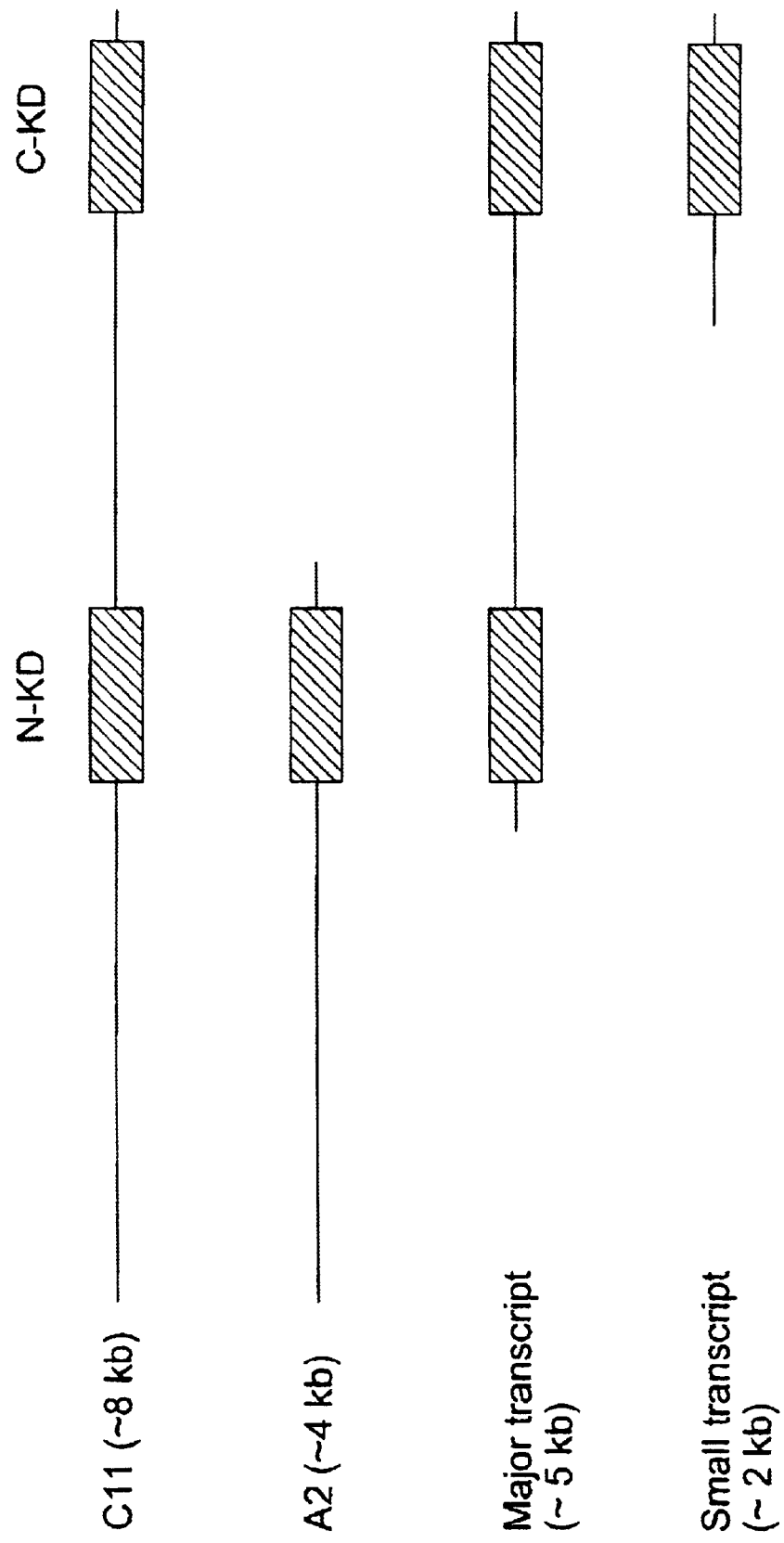
FIG. 4 is a schematic diagram of four cDNA clones corresponding to splicing variants of1H19G5. The longest clone (C11) contains two kinase domains, the N-terminal and the C-terminal kinase domains (N-KD and C-KD).
Figure 9:
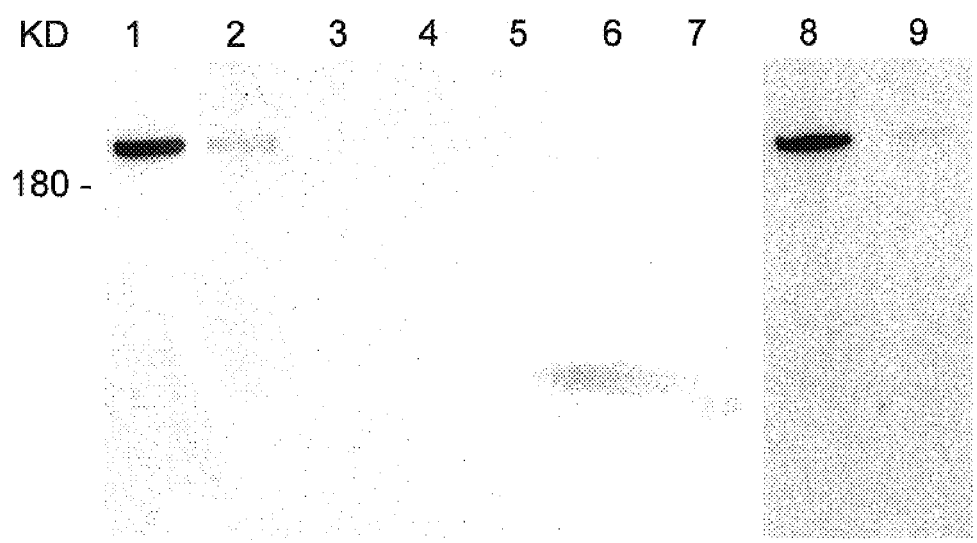
FIG. 9 shows that H19G5 protein expressed by the clone C11 binds to the small G protein Cdc42. The lysate of 293 EBNA cells transfected with H19G5-C11 expression construct was incubated with GST-Cdc42 immobilized on glutathione-agarose. After washing, the complex was resuspended in SDS sample buffer, boiled and run on a SDS-PAGE, and Western blotted with an anti-H19G5 monoclonal antibody.

Multiple transcripts were detected in Northern analysis of human and rat cells, particularly in heart tissues (as shown in FIGS. 8 and 9). However, the restriction analysis of the genomic clones and southern analysis of genomic DNA suggested single-copy nature of H19G5 gene. These observations indicated the possibility of alternative splicing as a source of multiple transcripts. Four cDNA clones representing various splicing variants were isolated and are schematically shown in FIG. 4. Complete nucleotide sequence (SEQ ID NO:5) of the longest clone C11 was determined and the amino acid sequence of a large open reading frame contained therein was deduced (SEQ ID NO: 6). The large ORF has a potential to encode a protein of 2596 amino acid residues. The sequence analysis revealed the presence of a number of structurally and functionally important domains in H19G5. The presence of some of the domains strengthens the possibility of the involvement of H19G5 in signal transduction. For example, H19G5 has two kinase domains, one at the N-terminal (1094 to 1341 amino acid residues, N-KD) (SEQ ID NO: 10) and the other at the C-terminal (2301 to 2553 amino acid residues, C-KD) (SEQ ID NO: 11) end. H19G5 also has a Guanine nucleotide Exchange Factor (GEF) domain (SEQ ID NO: 14) (325 to 504 amino acid residues), and a Pleckstrin Homology (PH) domain (SEQ ID NO: 17) (532 to 634 amino acid residues). Additionally, H19G5 contains five hnmunoglobulin (Ig) like domains distributed throughout the sequence.

Structural and Functional Features of Full-length H19G5 Protein Sequence

Figure 5:
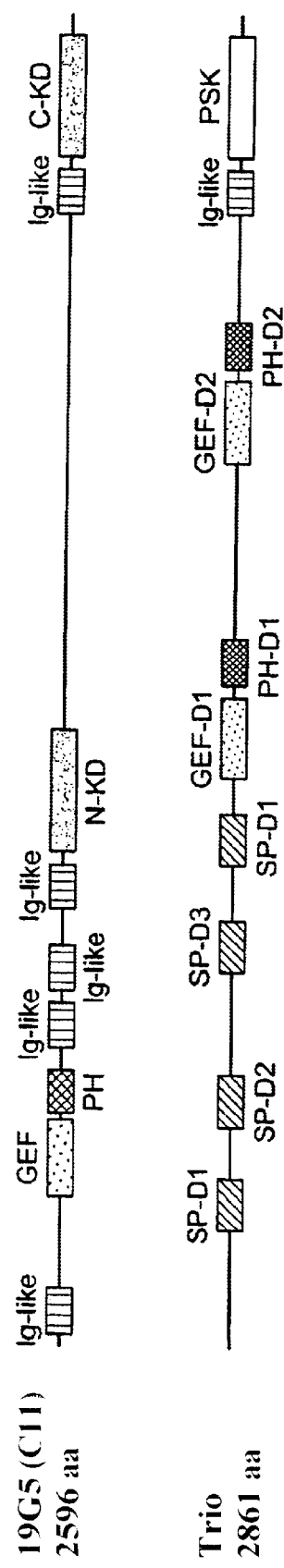
FIG. 5 is a schematic diagram comparing the domain structure of 19G5 and Trio proteins.
Figure 7:
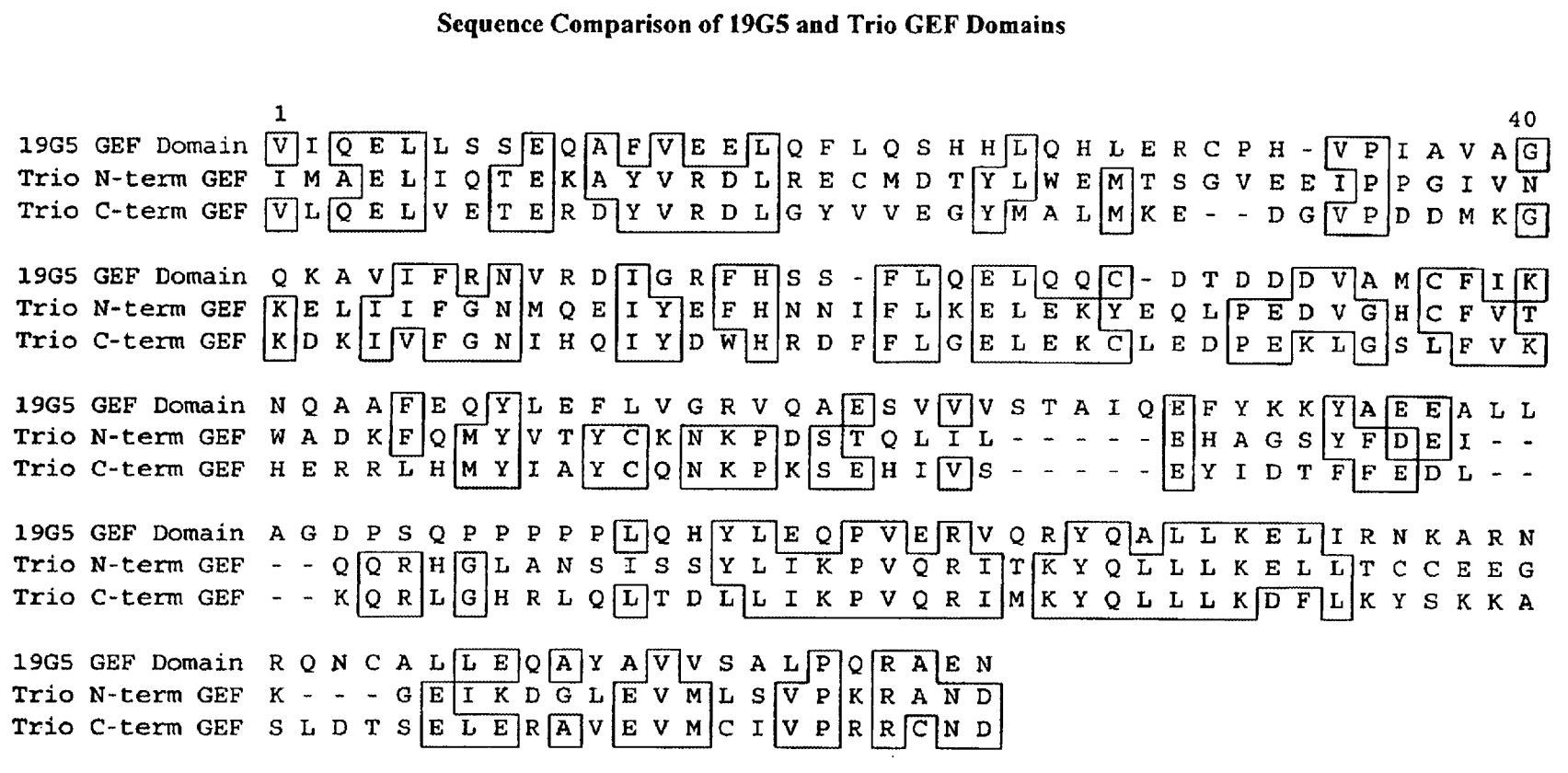

The full-length H19G5 amino acid sequence (SEQ ID NO: 6) shows sequence similarity to some functionally important domains of a protein called Trio. The comparison of the domain structure of H19G5 and Trio is schematically depicted in FIG. 5. Both kinase domains of Hi 9G5 (N-KD (SEQ ID NO: 10) and C-KD (SEQ ID NO: 11)) are homologous to a single kinase domain of Trio (SEQ ID NO: 12) as well as to a kinase domain of smooth muscle myosin light chain kinase (SM MLCK) (SEQ ID NO: 13) as shown in FIG. 6. The identity between H19G5 N-KD and Trio KD is about 40% and between Hi 9G5 N-KD and SM MLCK is about 38%. The sequence identity between the two kinase domains of H19G5 is about 30%. A single GEF domain of H19G5 (SEQ ID NO: 14) is homologous to both GEF domains (GEF-D1 (SEQ ID NO: 15) and GEF-D2 (SEQ ID NO: 16)) of Trio as shown in FIG. 7. GEF domain of H19G5 is homologous to both GEF domains (GEF-D1 and GEF-D2) of Trio as shown in FIG. 7.

Proteins containing GEF domains are involved in signal transduction (for a review, see Cherfils and Chardin, *Trends Biochem. Sci*. 24: 306–311 [1999]). GEF domains promote exchange of GTP for GDP on GTP-binding proteins (G proteins) and thereby positively regulate their activities. As these proteins harbor intrinsic GTPase activity, they are also referred to as GTPases. These small G proteins, as opposed to trimeric G proteins, belong to a superfamily of Ras-like proteins. These proteins are bound to the inner face of plasma membrane, and usually exist in GDP-bound "inactive" state. When a ligand interacts with a membrane bound receptor, alteration of conformation allows the receptor to interact with a G protein. This interaction results in conformational change in the G protein that weakens the affinity for GDP and leads to replacement of GDP with GTP. This nucleotide exchange is greatly accelerated or promoted by proteins containing GEF domains. Once bound to GTP, the G proteins assume an "active" state in which they interact with the downstream effectors and facilitate transduction of signal from membrane to the nucleus. However, the activity of the G proteins is tightly controlled as their intrinsic GTPase activity rapidly hydrolyzes bound GTP into GDP and restores "inactive" status. Thus, G proteins function as molecular switches in signal transduction. A number of membrane receptors operate through G proteins. The downstream effectors of the activated G proteins include various protein kinases constituting a cascade of protein phosphorylation that brings about a desired change in gene expression.

As discussed in the preceding section, GEF domains play a critical role in signal transduction by controlling the activation of G proteins. Trio is a complex protein possessing two GEF domains, each with adjacent pleckstrin homology (PH) domains and Src Homology-3 (SH3) domains, a protein serine/threonine kinase domain with an adjacent immunoglobulin-like domain and multiple spectrin-like domains (Medley et al., *J. Cell Sci*. 112: 1825–1834 [1999]). Trio cDNA clone was isolated by virtue of its ability to interact with protein tyrosine phosphatase (PTP) domain of a protein called LAR (Debant et al., *Proc. Natl. Acad. Sci. USA* 93: 5466–5471 [1996]). LAR is a broadly expressed transmembrane protein tyrosine phosphatase comprised of a cell adhesion-like extracellular region and two intracellular PTPase domains, and is proposed to regulate cell-matrix interactions (Mourey and Dixon, *Curr. Opin. Gen. Dev.* 4: 31–39 [1994]). Trio epresents a unique member of the Rho-GEFs family possessing two functional GEF omains of distinct specificities. For example, GEF1 is specifically active on Racl TPase, while GEF2 targets RhoA GTPase (Debant et al, supra). This unique feature allows Trio to link Rho and Rac specific signalling pathways in vivo.

The Rho family of Ras-like GTPases includes Rac (1, 2 and 3), RhoG, Cdc42Hs, TC10, TTF/RhoH, Rho (A, B and C), RhoD, RhoE, and RhoL. These proteins and other Ras-like proteins constitute Ras superfamily of structurally and functionally related GTPase proteins. These proteins are involved in diverse physiological functions such as control of cell shape (reviewed in Tapon and Hall, *Curr. Opin. Cell Biol.* 9: 86–92 [1997]), cell motility (Aepfelbacher et al., *Proc. Natl. Acad. Sci. USA* 91: 4263–4267 [1994]; and *Curr. Biol.* 6: 70–75 [1996]), cell polarity (Adams et al., *J. Cell Biol.* 111: 131–142 [1990]), smooth muscle contraction (Hirata et al., *J. Biol. Chem.* 267: 8719–8722 [1992]), cell adhesion (Nobes and Hall, *Cell* 81: 53–62 [1995]; Braga et al., *J. Cell Biol.* 137: 1421–1431 [1997]), cell division (Dutartre et al., *J. Cell Sci.* 109:367–377 [1996]), vesicular transport between organelles such as receptor-mediated endocytosis (Lamaze et al., *Nature* 382: 177–179 [1996]), apoptosis (Esteve et al., *Oncogene* 11: 2657–2665 [1995]; Jimenez et al., *Oncogene* 10: 811–816 [1995]; Gulbins et al., *J. Biol. Chem.* 271: 26389–26394 [1996]; Moorman et al., *J. Immunol.* 156: 4146–4153 [1996]; Brenner et al., *J. Biol. Chem.* 272: 22173–22181 [1997]) and normal and pathological cell proliferation (Olson et al., *Science* 269: 1270–1272 [1995]; Hirai et al., *J. Biol. Chem.* 272: 13–16 [1997]; Khosravi-Far et al., *Mol. Cell. Biol.* 16: 3923–3933 [1996]; Qiu et al., *Mol. Cell. Biol.* 17: 3449–3458 [1997]; Roux et al., *Curr. Biol.* 7: 629–637 [1997]).

The presence of a GEF domain and protein kinase domains along with its homology to Trio suggests that H19G5 may possess guanine nucleotide exchange factor activity and protein kinase activity, both of which are shared by a number of proteins involved in signal transduction.

Expression Pattern of 19G5 in Rat and Human Tissues

Northern blot analysis revealed that R19G5 gene is highly expressed in heart as a 2 kb and a 4.4 kb transcripts. Hybridization was performed using multiple tissue Northern blot (Clontech, Palo Alto, Calif.) and ExpressHyb solution following the manufacturer's protocol. The R19G5 probe also hybridized to mRNAs from skeletal muscle and detected multiple weak bands. High background observed in a lane corresponding to skeletal muscles is not due to RNA degradation as probing of the same blot with β-actin probe detected the right sized transcripts with a clean background. The significance of the high background in skeletal muscle is not clear. Expression of R19G5 was not detected in brain, kidney, spleen, lung, liver, and testis.

Hybridization of human multiple tissue Northern blot (Clontech, Palo Alto, Calif.) with H19G5 probe detected a strong transcript of about 5 kb and three minor transcripts of about 3 kb, 2.4 kb, and 1.8 kb in heart tissue. There were multiple transcripts and high background in skeletal muscle as seen with rat tissue. Only the 3 kb transcript was detected in human fetal heart. There is a low level expression of the 2.4 kb transcript in brain. H19G5 expression was not detected in spleen, lung, liver, kidney, pancreas, thymus, prostates, testis, ovary, small intestine, colon, peripheral blood leukocyte, stomach, thyroid, spinal cord, lymph node, trachea, adrenal gland, bone marrow, uterus muscle, or bladder muscle by Northern blot.

In order to determine whether the multiple transcripts of 19G5 in human heart are derived from alternative splicing or multiple gene copies, Southern blot analysis of genomic DNA was performed with H19G5 probe. The results suggest that H19G5 is a single copy gene. This is consistent with the lack of detection of polymorphism in the restriction analysis of the genomic clones of H19G5.

Functional Characterization of H19G5 Protein

A 20 amino acid peptide from the C-terminus of H19G5 protein (SEQ ID NO: 1) was used to raise polyclonal antibodies in rabbits. Affinity purified rabbit anti-H19G5 antiserum has been obtained. Two different GST-H19G5 fusion proteins were used as antigens to generate mouse monoclonal anti-H19G5 antibodies. One of the antigens used was a GST-H19G5 fusion protein containing amino acid residues 610 to 811 of SEQ ID NO: 1. Many clones of anti-19G5 monoclonal antibodies were obtained. Three of them were shown to recognize recombinant H19G5 proteins expressed in mammalian cells by Western analysis and immunocytochemistry. The antibodies may be used to determine the size and localization of 19G5 protein by Western blot and immunohistochemistry.

Subcellular localization of H19G5 protein was determined using confocal microscopy on cells transfected with vectors expressing 19G5 proteins fused to Green Fluorescent Protein (GFP). Three 19G5-GFP fusion protein expression constructs were made using three different 19G5 cDNA clones, the longest human 19G5 clone C11 [H19G5(C11)-GFP], and the rat 19G5 containing the C-terminal kinase domain [H19G59F1)-GFP], and the rat 19G5 small transcript [R19G5(S)-GFP]. The control GFP vector and the 19G5-GFP fusion expression constructs were transfected into C2C12 cells (ATCC Catalog No. CRL-1722). Cells were grown on chamber slides and transfected using Super-Fectamine reagent from Quiagen for 3 hrs. Cells were fixed 24 hrs post-transfection with 4% paraformaldehyde for 15 min at room temperature and examined using a confocal microscope. The two longer forms of human 19G5-GFP proteins were detected in the nuclei whereas the short rat 19G5-GFP fusion protein was detected in the cytoplasm (FIG. 8). This suggests that different forms of 19G5 proteins are localized in different regions in the cells and may have different functions. Since the gene is normally expressed in heart, the localization of 19G5 protein in cardiac myocytes may be examined. Antisense constructs to study the effects of inhibiting the activity of 19G5 protein on cardiac myocytes may also be made and used.

A possibility that H19G5 might interact with various G proteins, as suggested by the presence of GEF domain and homology with Trio, was examined. HEK 293 cells constitutively expressing Epstein-Barr Virus Nuclear Antigen (EBNA) (Invitrogen, San Diego, Calif.) were transfected with H19G5-C11 expression construct. The eukaryotic vector used for 19G5 expression, pEAK8 (EdgeBiosystems), contains Epstein-Barr virus (EBV) origin of DNA replication, which allows replication. of the expression construct in transfected cells thereby amplifying the level of protein expression. After 24 hrs, one 10 cm dish of transfected 293 EBNA cells were lysed with 1 ml of lysis buffer (1×PBS, 0.1% Triton, and proteinase inhibitors (0.2 mM AEBSF, 0.16 μM Aprotinin, 0.01 mM Bestatin, 3 μM E-64, 4 μM Leupeptin, and 2 μM Pepstatin) on ice for 30'. Cells were then homogenized with a dounce homogenizer on ice. The lysates were cleared by centrifugation. One ml of the cleared lysate was incubated with 5 μg of various small G proteins, expressed as GST fusion proteins and bound to glutathione-agarose beads, at 4° C. for 2 hrs. The protein-agarose complex was pelleted by brief centrifugation and washed for 4 times 5' each with the lysis buffer at room temperature. The complex was then resuspended in SDS sample buffer, boiled and run on a SDS-PAGE and Western blotted with an anti-H19G5 monoclonal antibody. As shown in FIG. 9, H19G5 was found to bind to Cdc42. No binding was detected with Rac1 or RhoA. Lane 8 is His-tagged Cdc42 and in lane 9 His-tagged Cdc42-agarose complex was boiled for 5' before adding to the H19G5 cell lysate. This result showed that H19G5 specifically interacts with Cdc42 protein and there is no non-specific interaction with agarose beads. The results presented herein suggest that 19G5 protein may play an important role, by virtue of regulating a small GTPase such as Cdc42Hs, in a variety of cellular activities. For example, Cdc42 has been shown to regulate actin polymerization and focal adhesion complex formation which in turn is necessary for filopedia formation (Nobes and Hall, *Cell* 81: 53–62 [1995]). Cdc42 and rac have also been shown to regulate Jun N-terminal kinase (JNK) activity via the MAP kinase pathway (Coso et al., *Cell* 81: 1137–1146 [1995]; Minden et al., *Cell* 81: 1147–1157 [1995]; Olson et al., *Science* 269: 1270–1272 [1995]), an evolutionarily conserved and ubiquitous signal transduction pathway that impacts upon a number of important cellular functions.

Figure 10:
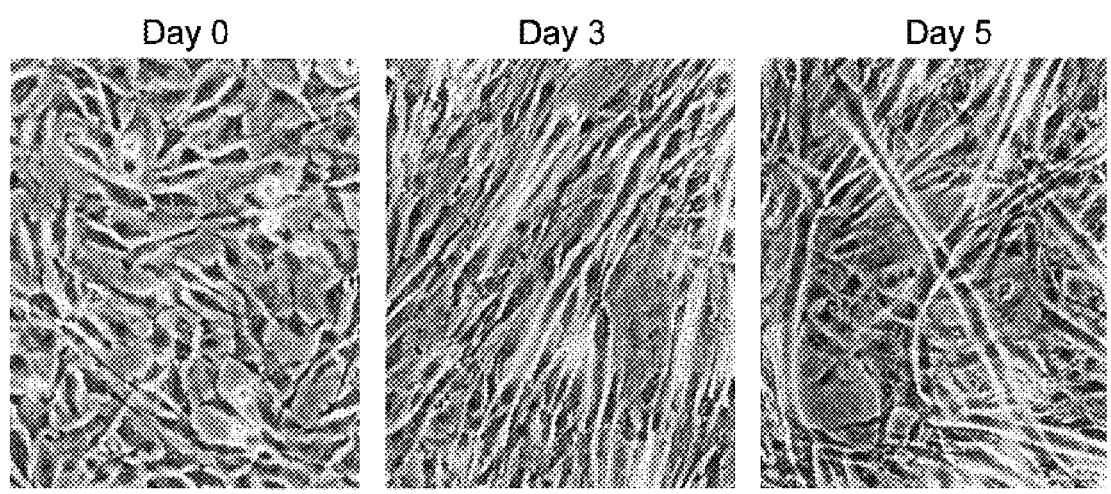
FIG. 10 shows phase contrast micrographs of C2C12 myoblasts undergoing differentiation into myotubes. Undifferentiated C2C12 cells are shown in Day 0. Differentiation of C2C12, induced by placing 2% horse serum, is apparent on Day 3 and Day 5 as shown.
Figure 11:
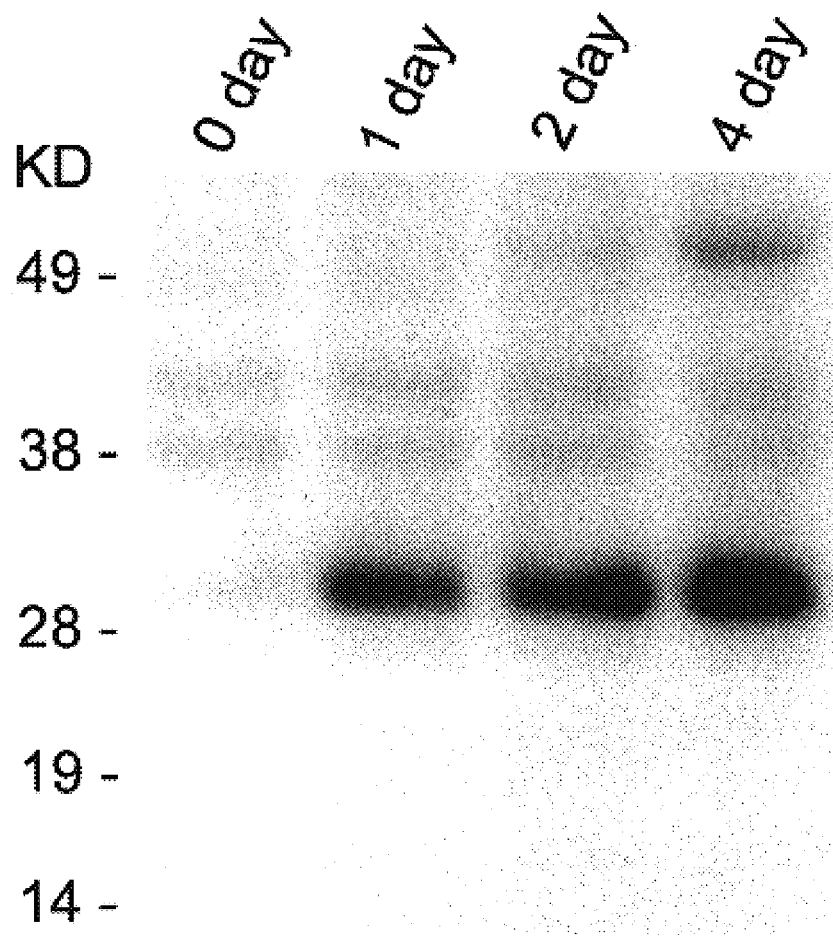
FIG. 11 shows induction of myogenin protein expression when C2C12 myoblast cells are induced to differentiate into myotubes. Myogenin is a marker of myotubes.

C2C12 myoblasts cells (ATCC Catalog No. CRL-1772) can be induced to differentiate into myotubes when placed in a medium containing 2% horse serum (Lechner et al., *Proc. Nat. Acad. Sci. USA* 93: 4355–4359 [1996]). FIG. 10 shows phase contrast micrographs of C2C12 myoblasts undergoing differentiation into myotubes. At Day 0, undifferentiated C2C12 cells with typical myoblast morphology can be seen. Once induced to differentiate, as shown here at Day 3 and 5 after induction, an increasingly larger number of cells with typical morphology of differentiated myotubes, i.e. large, elongated, multinucleated syncytial cells, could be seen. The induction of Myogenin expression was monitored during differentiation. Myogenin is not expressed in myoblasts, however, its expression is strongly induced when myoblasts undergo differentiation into myotubes. Thus, it acts as a biochemical marker of myotubes. FIG. 11 shows induction of myogenin protein expression when C2C12 myoblast cells are induced to differentiate into myotubes. C2C12 cells were cultured and induced to differentiate by placing in a medium containing 2% horse serum. Cells were lysed in radioimmunoprecipitation (RIPA) buffer (1×PBS containing 1% Igepal CA-630, 0.5% sodium deoxycholate and 0.1% SDS) on ice for 30'. Total lysates were cleared by centrifugation at 10,000 rpm for 10'. Protein concentration of each lysate was measure using the BCA method. SDS sample buffer was added to the total lysate and boiled for 3'. Equal amount of total protein of each sample was run on SDS-PAGE and blotted using an anti-myogenin monoclonal antibody. The result demonstrated that Myogenin expression was induced concomitantly with differentiation of C2C12 myoblasts into myotubes under the conditions used for induction.

Figure 12:
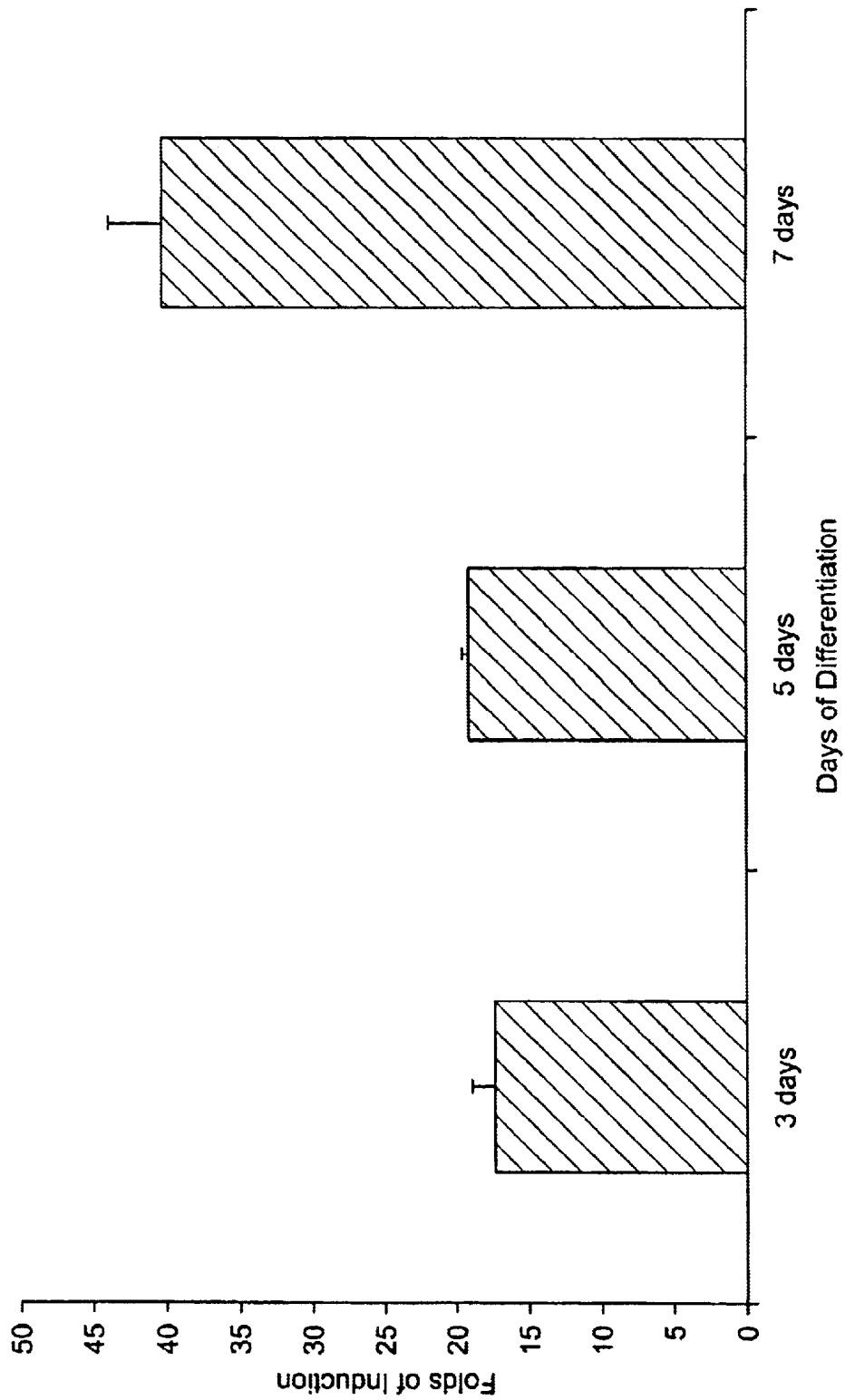
FIG. 12 shows induction of 19G5 RNA expression during the differentiation of myoblasts into myotubes.

The expression of 19G5 RNA was also monitored at various stages during differentiation of myoblasts into myotubes. Undifferentiated C2C12 cells were plated on 6 cm dishes at $2.4 \times 10^4$ cells/cm$^2$ and cultured in growth medium with 10% fetal bovine serum for 24 hrs to about confluence. Cells were washed with PBS and induced to differentiate into myotubes in differentiation medium with 2% horse serum. Total RNA was isolated from cells at 1, 2, or 4 days post-induction using Qiagen's Rneasy kit according to the manufacture's instruction. The expression of 19G5 transcript was analyzed using Taqman assay. One microgram of total RNA, isolated at various time points post-induction, was reverse transcribed into cDNA using PE Biosystems Reagents and Multiscribe enzyme according to manufacture's instruction. Ten ng of cDNA was added to 1×master mix, and the primers and probe for the gene of interest were added according to manufacture's instructions. The reaction were carried out in the ABI Prism 7700 Detection System. The quantity of 19G5 and the quantity for 18S were determined for each sample, and the ratio of 19G5/18S was used to evaluate differences in the level of 19G5 expression in various samples. Comparison of the values thus obtained with pre-induction values allowed to determine fold induction of 19G5 expression during differentiation. As shown in FIG. 12, expression of 19G5 transcript was significantly increased during differentiation of C2C12 myoblasts into myotubes. The level of induction reached to about 10-fold at 4 days post-induction. Increased expression of 19G5 likely reflects a specific function in myotubes.

Figure 13:
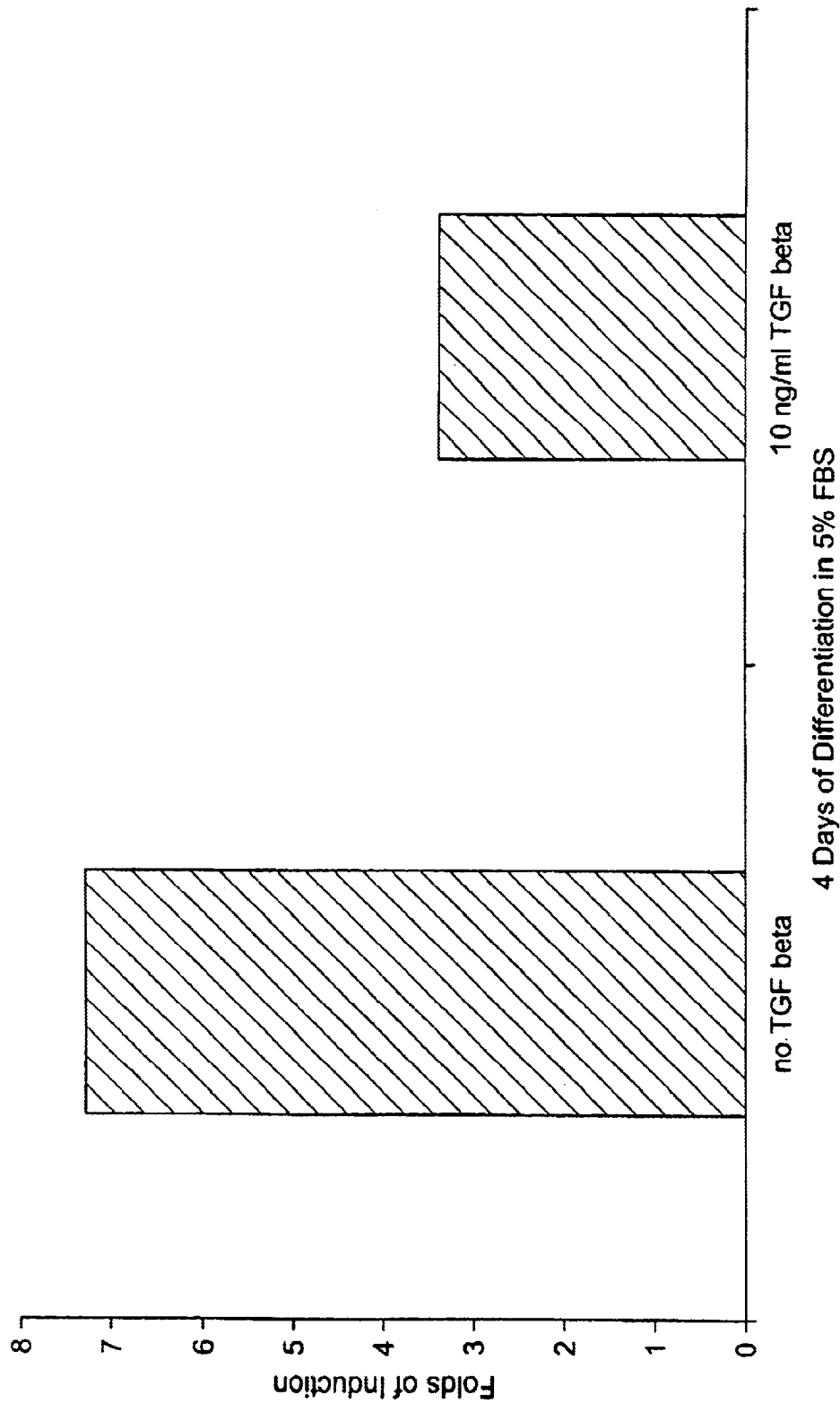
FIG. 13 shows inhibition of the induction of 19G5 expression by TFG-β during C2C12 differentiation.

TGF-β is known to inhibit differentiation of C2C12 myoblast into myotubes (Katagiri et al., *J. Cell Biol.* 127: 1755–1766 [1994]; Namiki et al., *J. Biol. Chem.* 272: 22046–22052 [1997]). Therefore, the effect of TGF-β on the induction of expression of 19G5 during differentiation of C2C12 cells was examined. C2C12 cells were plated in 6 cm dishes at $2.4 \times 10^4$ cells/cm$^2$ and cultured in the growth medium for 24 hours. Cells were then rinsed with PBS and induced to differentiate for 4 days in the medium containing 5% fetal bovine serum either in the absence or in the presence of 10 ng/ml of TGF-β. Total RNA was isolated from cells using Qiagen's Rneasy kit. Induction of 19G5 expression in TGF-β treated or untreated cells over undifferentiated C2C12 cells was measured by Taqman assay. As shown in FIG. 13, the induction of 19G5 expression during C2C12 differentiation is inhibited by TFG-β. TGF-β is a powerful regulator of cell growth and differentiation and regulation of expression of 19G5 by TGF-β likely represents an important physiological event with significant relevance to normal and abnormal changes in cardiac cells. Furthermore, the results suggest a possible involvement of 19G5 in myogenesis.

EXAMPLE 2

Polypeptides Which can Mediate Signal Transduction

The polypeptides of the present invention, such as the specific embodiment shown in SEQ ID NOs: 1, 4, 6, 7, 8 or 9 may be prepared by any known techniques. Conveniently, the polypeptides may be prepared using the solid-phase synthetic technique initially described by Merrifield in *J. Am. Chem. Soc.* 15:2149–2154 (1963). Other peptide synthesis techniques may be found, for example, in M. Bodanszky et al., *Peptide Synthesis*, John Wiley & Sons, 2d Ed. (1976) as well as in other reference works known to those skilled in the art. A summary of peptide synthesis techniques may be found in J. Stuart and J. D. Young, *Solid Phase Peptide Synthelia*, Pierce Chemical Co., Rockford, Ill. (1984). The synthesis of peptides by solution methods may also be used, as described in THE PROTEINS, Vol-II, 3d Ed., Neurath, H. et al., Eds., p.105–237, Academic Press, New York, N.Y. (1976). Appropriate protective groups for use in such syntheses will be found in the above texts as well as in J. F. W. McOmie, *Protective Groups in Organic Chemistry*, Plenum Press, New York, N.Y. (1973). In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The polypeptides of the invention preferably are devoid of benzylated or methylbenzylated amino acids. Such protecting group moieties may be used in the course of synthesis, but they are removed before the polypeptides are used. Additional reactions may be necessary, as described elsewhere to form intramolecular linkages to restrain conformation, if desired. The polypeptides of the present invention may also be linked to an additional sequence of amino acids either or both at the N-terminus and at the C-terminus. Such additional amino acid sequences, or linker sequences, can be conveniently affixed to a detectable label, solid matrix, or carrer. Typical amino acid residues used for linking are tyrosine, cysteine, lysine, glutamic acid and aspartic acid, or the like.

Of course, the present polypeptides may also be prepared by recombinant DNA techniques as described, for example, in Sambrook, et al., *Molecular Cloning: A Laboratory Manual*, Chapters 1–18, Second Edition (Cold Spring Harbor N.Y. 1989), and as detailed in Examples 3–4 infra. The present invention also relates to vectors comprising DNA molecules of the present invention, host cells which are genetically engineered with vectors of the invention and the production of polypeptides of the invention by recombinant techniques. Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying genes. The culture conditions, such as temperature, pH and the like, are preferably those previously used with the host cell selected for expression, and will be apparent to the skilled artisan.

EXAMPLE 3

Hosts, Vectors and DNA Encoding Polypeptides which can Mediate Signal Transduction The DNA molecules of the present invention may be employed for producing the polypeptides of the present invention by recombinant techniques. More particularly, the present invention also includes recombinant constructs comprising one or more of the sequences broadly described above. Thus, for example, the DNA molecule sequence may be included in any one of a variety of expression vehicles, in particular vectors or plasmids for expressing such a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA; viral DNA such as vaccinia, adenovirus, fowl pox virus, and pseudorabies. The following vectors are provided by way of example. Bacterial: pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, PRIT5 (Pharmacia). Eukaryotic: pWLneo, pSV2cat, pOG44, pXT1, pSG (Stratagene); pSVK3, pBPV, pMSG, PSVL (Pharmacia). However, any other vector or plasmid may be used as long as they are replicable and viable in the host. The vector containing the appropriate DNA sequence, as well as an appropriate promoter or control sequence, may be employed to transform an appropriate host to permit the host to express the polypeptides of the present invention. Representative examples of appropriate hosts include: bacterial cells, such as *E. coli, Salmonella typhimurium*, Streptomyces; fungal cells, such as yeast; insect cells, such as Drosophila S2 and Spodoptera Sf9; animal cells, such as CHO, COS or Bowes melanoma; adenoviruses; plant cells, etc. The selection of an appropriate host is deemed to be within the scope of those skilled in the art.

The appropriate DNA sequence may be inserted into the vector by a variety of procedures. In general, the DNA sequence is inserted into an appropriate restriction endonuclease site by procedures known in the art. Such procedures and others are deemed to be within the scope of those skilled in the art.

The DNA sequence in the expression vector may be operatively linked to an appropriate expression control sequence(s) (promoter) to direct mRNA synthesis. Suitable promoter regions can be selected from any desired gene using CAT (chloramphenicol transferase) vectors or other vectors with selectable markers. Two ppropriate vectors are pKK232-8 and pCM7. Particular named bacterial promoters include laci, lacZ, T3, T7, gpt, lambda $P_R$, $P_L$ and trp. Eukaryotic promoters include CMV immediate early, HSV thymidine kinase, early and late SV40, LTRs from retrovirus, and house metallothionein-I. Selection of the appropriate vector and promoter is well within the level of skill in the art. The expression vector may also contain a ribosome binding site for translation initiation and a transcription terminator. The vector may also include appropriate sequences for amplifying expression.

In addition, the expression vectors preferably may contain a gene to provide a phenotypic trait for selection of transformed host cells such as dihydrofolate reductase or neomycin resistance for eukaryotic cell culture, or such as tetracycline or ampicillin resistance in *E. coli*.

An embodiment of the invention is an isolated DNA molecule comprising the nucleotide sequence of SEQ ID NOs: 2, 3 or 5. This nucleotide sequence, or fragments or functional equivalents thereof, may be used to generate recombinant DNA molecules that direct the expression of the polypeptides of the present invention, or functionally active peptides or fictional equivalents thereof, in appropriate host cells. Due to the degeneracy of the nucleotide coding sequence, other DNA sequences which encode substantially the same amino acid sequences as depicted in SEQ ID NOS: 1, 4, 6, 7, 8 or 9, or analogs or fragments thereof, may be used in the practice of the invention for the cloning and expression of a mediator of signal transduction. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity, the amphipathic nature of the residues involved and/or on the basis of crystallographic data. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

Techniques well known to those skilled in the art for the isolation of DNA, generation of appropriate restriction fragments, construction of clones and libraries, and screening recombinants may be used. For a review of such techniques, see, for example, Sambrook, et al., supra, the disclosure of which is hereby incorporated by reference. Also, the 5' untranslated and coding regions of the nucleotide sequence could be altered to improve the translational efficiency of the mRNA. In addition, based on X-ray crystallographic data, sequence alterations could be undertaken to improve protein stability, e.g., introducing disulfide bridges at the appropriate positions, and/or deleting or replacing amino acids that are predicted to cause protein instability. These are only examples of modifications that can be engineered to produce a more active or stable protein, more protein, or even change the substrate specificity of the protein.

EXAMPLE 4

Cells Transformed with Recombinant Vectors Containing DNA Encoding Polypeptides which can Mediate Signal Transduction In a further embodiment, the present invention relates to host cells containing the above-described construct. The host cell can be a higher eukaryotic cell, such as a manunalian cell, or a lower eukaryotic cell, such as a yeast cell, or the host cell can be a prokaryotic cell, such as a bacterial cell. The host cell preferably may secrete the recombinant protein. Introduction of the construct into the host cell can be effected by calcium phosphate transfection, DEAE-Dextran mediated transfection, or electroporation (L. Davis et al., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., supra.

Transcription of a DNA encoding the polypeptides of the present invention by higher eukaryotes may be increased by inserting an enhancer sequence into the vector. Enhancers are cis-acting elements of DNA, usually from about 10 to 300 bp, that act on a romoter to increase its transcription. Examples include the SV40 enhancer on the late side of the replication origin (base pair 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRPI gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is preferably assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use may be constructed by inserting a structural DNA sequence encoding a desired protein together with suitable translation, initiation and termination signals in operable reading phase with a functional promoter. The vector may comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223–3 (Pharmacia Fine Chemicals, Uppsala, Sweden) and GEM1 (Promega Biotec, Madison, Wis.). These pBR322 backbone sections are combined with an appropriate promoter and the structural sequence to be expressed.

Following transformation of a suitable host strain and growth of the host strain to an appropriate cell density, the selected promoter may be de-repressed by appropriate means (e.g., temperature shift or chemical induction) and cells may be cultured for an additional period. Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Various mammalian cell culture systems can also be employed to express recombinant polypeptides. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors may comprise an origin of replication, a suitable promoter and enhancer, and also any necessary ribosome binding sites, polyadenylation sites, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

The polypeptides of the present invention may be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic-procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

In particular, two baculivirus expression constructs of a wild-type and a mutant H19G5 C-terminal kinase domain have been constructed. The wild-type kinase domain construct was made by cloning a cDNA fragment which encodes the amino acid residues 1002 to 1314 of the H19G5 contig protein sequence into the pFastBac HTc vector. The mutant kinase domain construct contains the same amino acid sequence as the wild-type kinase domain except that Tyr residue at position 1213 was changed to a Glu in an attempt to create a constitutively active kinase. Both recombinant proteins contain a his-tag at the N-terminus.

EXAMPLE 5

Pharmaceutically Acceptable Salts of Polypeptides which can Mediate Signal Transduction Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

EXAMPLE 6

Pharmaceutical Compositions Containing Polypeptides which can Mediate Signal Transduction For use in a method of identification, prevention or treatment, such as the identification, prevention or treatment of infection of a mammalian host by a microorganism, the polypeptides of the present invention may be present in a pharmaceutical composition in admixture with a pharmaceutically acceptable sterile vehicle. The pharmaceutical composition may be compounded according to conventional pharmaceutical formulation techniques.

The vehicle may take a wide variety of forms depending on the form of preparation desired for administration, e.g., sublingual, rectal, nasal, oral or parenteral. Compositions for oral dosage form may include any of the usual pharmaceutical media, such as, for example, water, oils, alcohols, flavoring agents, preservatives, coloring agents and the like in the case of oral liquid preparations (e.g., suspensions, elixirs and solutions) or carriers such as starches, sugars, diluents, granulating agents, lubricants, binders, disintegrating agents and the like in the case of oral solid preparations (e.g., powders, capsules and tablets). Controlled release forms may also be used. Because of their ease in administration, tablets and capsules represent an advantageous oral dosage unit form, in which case solid pharmaceutical carriers may be employed. If desired, tablets may be sugar coated or enteric coated by standard techniques.

For compositions to be administered parenterally, the carrier will usually comprise sterile water, although other ingredients to aid solubility or for preservation purposes may be included. Injectable suspensions may also be prepared, in which case appropriate liquid carriers, suspending agents and the like may be employed. The parenteral routes of administration may be intravenous injection, intramuscular injection or subcutaneous injection.

For intravenous administration, the polypeptides may be dissolved in an appropriate intravenous delivery vehicle containing physiologically compatible substances such as sodium chloride, glycine and the like, having a buffered pH compatible with physiologic conditions. Such intravenous delivery vehicles are known to those skilled in the art.

The polypeptides of the invention may be administered to subjects where mediation of signal transduction is desired. The peptides may be administered by any convenient means that will result in the delivery to the subject of an effective amount to mediate signal transduction. Oral administration is presently contemplated as a preferred administration route. The amount administered will depend on the activity of the particular compound administered, which may readily be determined by those of ordinary skill in the art.

EXAMPLE 7

Monoclonal Antibodies Against Polypeptides which can Mediate Signal Transduction Another embodiment of the present invention relates to a monoclonal antibody to the polypeptides of the present invention (or an antigenic portion thereof), which may be produced by methods recognized in the art, including the formation of monoclonal antibody-producing hybridomas (Kohler, G., and C. Milstein, Nature 256:495–497 (1975); Eur. J. Immunol. 6:511–519 (1976)). By fusing antibody-forming cells (spleen lymphocytes) with myeloma cells (malignant cells of bone marrow primary tumors), a hybrid cell line is created from a single fused cell hybrid (called a hybridoma or clone) having certain inherited characteristics of both the lymphocytes and myeloma cell lines. Like the lymphocytes (taken from animals primed with sheep red blood cells as antigen), the hybridomas secreted a single type of immunoglobulin specific to the antigen; moreover, like the myeloma cells, the hybrid cells had the potential for indefinite cell division. The combination of these two features offered distinct advantages over conventional antisera. Whereas antisera derived from vaccinated animals are variable mixtures of polyclonal antibodies which never can be reproduced identically, monoclonal antibodies are highly specific immunoglobulins of a single type. The single type of immunoglobulin secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences (generally 6–7 amino acids in length (Atassi, M. Z., *Molec. Cell. Biochem.* 32:21–43 (1980)) within the entire protein molecule. Hence, monoclonal antibodies raised against a single antigen may be distinct from each other depending on the determinant that induced their formation; but for any given clone, all of the antibodies it produces are identical. Furthermore, the hybridoma cell line can be reproduced indefinitely, is easily propagated in vitro or in vivo, and yields monoclonal antibodies in extremely high concentration.

EXAMPLE 8

Therapeutic Monoclonal Antibodies Against Polypeptides which can Mediate Signal Transduction The monoclonal antibodies of the present invention can have potential immunotherapeutic value (Oldham, R. K., *J. Clin. Oncol.*, 1:582–590 (1983); Miller, R. A. et al., *Blood*, 62:988–995 (1983); Miller R. A. et al., *New Engl. J. Med.* 306:517–522 (1982); Ritz, J. and Schlossman, S., *Blood*, 59:1–11 (1982); and Kirch, M. E. and Ulrich, H., *J. Immunol.* 127:805–810 (1981) (investigating the therapeutic efficacy in both animal and human subjects)). In addition, the monoclonal antibodies can be used in cytotoxic drug-antibody conjugates similar to those described in Beverly, P. C. L., *Nature*, 297:358–9 (1982); Krolick, K. A. et al., *Nature*, 295:604–5 (1982); Krolick, K. A. et al., *Proc. Natl. Acad. Sci. U.S.A.*, 77:5419–23 (1980); Amon, R. and Sela, M., *Immunol. Rev.*, 62:5–27 (1982); Raso, V. et al., *Cancer Res.*, 42:457–64 (1982); and DeWeger, R. A. and Dullens, H. F. J., *Immunol. Rev.* 62:29–45 (1982).

In an embodiment of the invention, purified polypeptides of the present invention (or an antigenic portion thereof) can be used as an antigen or immnunogen. In addition, microorganisms expressing H19G5 protein or polypeptide fragments thereof also represent potential antigens or sources of antigen with which to immunize animals to obtain somatic cells for fusion. Somatic cells with the potential for producing antibody and, in particular, B lymphocytes, are suitable for fusion with a B-cell myeloma line. Those antibody-producing cells that are in the dividing plasmablast stage fuse preferentially. Somatic cells may be derived from the lymph nodes, spleens and peripheral blood of primed animals and the lymphatic cells of choice depending to a large extent on their empirical usefulness in the particular fusion system. Once-primed or hyperimmunized animals can be used as a source of antibody-producing lymphocytes. Mouse lymphocytes give a higher percentage of stable fusions with mouse myeloma lines. However, the use of rat, rabbit, and frog cells is also possible. Alternatively, human somatic cells capable of producing antibody, specifically B lymphocytes, are suitable for fusion with myeloma cell lines. While B lymphocytes from biopsied spleens or lymph nodes of individual may be used, the more easily accessible peripheral blood B lymphocytes are preferred. The lymphocytes may be derived from patients with diagnosed carcinomas.

Specialized myeloma cell lines have been developed from lymphocyte tumors for use in hybridoma-producing fusion procedures (Kohler, G., and C. Milstein, *Eur. J. Immunol.* 6:511–519 (1976); M. Schulman et al., *Nature* 276: 269–270 (1978)). Examples of myeloma cell lines that may be used for the production of fused cell hybrids include X63-Ag8, NSI-Ag4/1, MPC11-45. 6TG1.7, C63-Ag8.653, Sp2/0-Ag14, OF, and S194/5XX0.BU.1, all derived from mice; 210.RCY3.Ag1.2.3, U-226AR, and GM1500GTGAL2, all derived from rats; and U-226AR and GM1500GTGAL2, derived from humans, (G. J. Hammerling, U. Hammerling, and J. F. Kearney (editors), Monoclonal Antibodies and T-cell Hybridomas in: J. L. Turk (editor) *Research Monographs in Immunology*, Vol. 3, Elsevier/North Holland Biomedical Press, N.Y. (1981)).

Methods for generating hybrids of antibody-producing spleen or lymph node cells and myeloma cells usually comprise mixing somatic cells with myeloma cells in a 2:1 proportion (though the proportion may vary from about 20:1 to about 1:1), respectively, in the presence of an agent or agents (chemical or electrical) that promote the fusion of cell membranes. It is often preferred that the same species of animal serve as the source of the somatic and myeloma cells used in the fusion procedure. Fusion methods have been described by Kohler and Milstein (*Nature* 256:495–497 (1975) and *Eur. J. Immunol.* 6:511–519 (1976), and by Gefter et al. (*Somatic Cell Genet.* 3:231–236 (1977)). The fusion-promotion agents used by those investigators were Sendai virus and polyethylene glycol (PEG), respectively.

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

EXAMPLE 9

Diagnostic Monoclonal Antibodies Against Polypeptides which can Mediate Signal Transduction The monoclonal antibodies of this invention can be used as probes in detecting discrete antigens expressed by tissue or cell samples. The expression or lack of expression of these antigens can provide clinically exploitable information that is not apparent after standard histopathological evaluations. It may thus be possible to correlate the immuno-phenotypes of individual tissue or cell samples with various aspects of signal transduction and responsiveness to certain types of therapies, thereby establishing important classifications of prognosis.

The use of the monoclonal antibodies described herein can be extended to the screening of human biological fluids for the presence of the specific antigenic determinant recognized. In vitro immunoserological evaluation of sera withdrawn from patients thereby permits non-invasive diagnosis of disease. By way of illustration, human fluids, such as pleural fluids or lymph, can be taken from a patient and assayed for the specific epitope, either as released antigen or membrane-bound on cells in the sample fluid, using monoclonal antibodies against the polypeptides of the present invention in standard radioimmunoassays or enzyme-linked immunoassays known in the art or competitive binding enzyme-linked immunoassays.

The monoclonal antibodies of this invention are potentially useful for targeting diseased tissue or cells in vivo. They can therefore be used in humans for localization and monitoring of the microbial infection. For this application, it is preferable to use purified monoclonal antibodies. Purification of monoclonal antibodies for human administration by ammonium sulfate or sodium sulfate precipitation followed by dialysis against saline and filtration sterilization has been described by Miller et al. (in: *Hybridomas in Cancer Diagnosis and Therapy*, (1982), p. 134).

Alternatively, immunoaffinity chromatography techniques may be used to purify the monoclonal antibodies. The purified monoclonal antibodies can be labeled with radioactive compounds, for instance, radioactive iodine, and administered to a patient intravenously. After localization of the antibodies at the infection site, they can be detected by emission tomographical and radionuclear scanning techniques, thereby pinpointing the location of the infection. Experimental radioimmunodetection with monoclonal antibodies may occur by external scintigraphy.

Passive monoclonal serotherapy may be a potential use for the monoclonal antibodies of this invention. By way of illustration, purified anti-H19G5 monoclonal antibody is dissolved in an appropriate carrier, e.g. saline, with or without human albumin, at an appropriate dosage and is administered to a patient. The monoclonal antibodies are preferably administered intravenously, e.g., by continuous intravenous infusion over several hours, as in Miller et al, supra. Infusions can be administered over a period of weeks during which the anti-microbial effects are monitored.

EXAMPLE 10

Anti-idiotypic Antibodies to Antibodies Against Polypeptides which can Mediate Signal Transduction In an alternate embodiment, the antibodies described herein are used to stimulate the production of corresponding anti-idiotypic antibodies. ; In brief, anti-idiotypic antibodies, or antiidiotypes are antibodies directed against the antigen combining region or variable region (idiotype) of another antibody. Based on Jeme's network model of idiotypic relationships (Jerne, *Ann. Immunol*; 125:373 (1974); Jerne et al., *EMBO* 1:234 (1982)), immunization with an antibody molecule expressing a paratope (antigen-combining site) for a given antigen should produce a group of anti-antibodies, some of which share with the antigen a complementary structure to the paratope. Immunization with a subpopulation of antiidiotypic antibodies should in turn produce a subpopulation of antiudiotypic antibodies which bind the initial antigen. Thus, the administration of the monoclonal antibodies of the present invention may result in a modification of the host's immune response, as the consequence of the formation of anti-idiotypic antibodies which may develop during therapy with the monoclonals.

EXAMPLE 11

Monoclonal Antibody-drug Conjugates

The monoclonal antibodies of this invention can be used in conjunction with a broad spectrum of pharmaceutical or cytotoxic agents that selectively affect diseased tissue or cells over normal tissues or cells in the mammalian host. The methods used for binding the cytotoxic agents to the monoclonal antibody molecule can involve either non-covalent or covalent linkages. Since non-covalent bonds are more likely to be broken before the antibody complex reaches the target site, covalent linkages are preferred. For instance, carbodiimide can be used to link carboxy groups of the pharmaceutical agent to amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde that is then reacted with the antibody molecule. Attachment occurs via formation of a Schiff base with amino groups of the antibody molecule. Additionally, drugs with reactive sulfhydryl groups have been coupled to antibody molecules.

EXAMPLE 12

Diagnostic Kit

Another embodiment of the invention relates to a diagnostic kit for detecting diseased tissue or cells using an antibody against a polypeptide which can mediate signal transduction. The diagnostic kit may further comprise, where necessary, other components of the signal producing system, including agents for reducing background interference, control reagents, or an apparatus, container or other solid support for conducting the test. The binding of antibody to the target can be detected by well known methods, including radiation (e.g., use of a radioactive nucleotide), colorimetry (e.g., use of an enzyme that can cause a color change in a substrate), fluorescence (e.g., use of a dye such as propidium iodide, fluorescein, or rhodamine), and luminescence (e.g., use of an alkaline phosphatase substrate that releases photons upon cleavage or luciferin). Detection can be qualitative or quantitative.

EXAMPLE 13

Gene Therapy

Another embodiment of the present invention involves the use of the DNA of the present invention in gene therapy applications. Gene therapy has been broadly defined as "the correction of a disease phenotype through the introduction of new genetic information into the affected organism" (Roemer, K. and Friedmann, T., *Eur. J. Biochem.* 208: 211–225 (1992)). Two basic approaches to gene therapy have evolved: (1) ex vivo gene therapy and (2) in vivo gene therapy. In ex vivo gene therapy, cells are removed from a subject and cultured in vitro. A functional replacement gene is introduced into the cells (transfection) in vitro, the modified cells are expanded in culture, and then reimplanted. in the subject. These genetically modified, reimplanted cells are reported to secrete detectable levels of the transfected gene product in situ (Miller, A. D., *Blood* 76: 271–278 (1990)) and Selden, R. F., et al., *New Eng. J. Med.* 317: 1067–1076 (1987)). The development of improved retroviral gene transfer methods (transduction) facilitates the transfer into and subsequent expression of genetic material by somatic cells (Cepko, C. L., et al., *Cell* 37: 1053–1062 (1984)). Accordingly, retrovirus-mediated gene transfer has been used in clinical trials to mark autologous cells and as a way of treating genetic disease (Rosenberg, S. A., et al., New Eng. J. Med. 323: 570–578 (1990); Anderson, W. F., *Human Gene Therapy* 2: 99–100 (1991)). Several ex vivo gene therapy studies in humans are reported (reviewed in Anderson, W. F., *Science* 256: 808–813 (1992) and Miller A. D., Nature 357: 455–460 (1992)).

In in vivo gene therapy, target cells are not removed from the subject. Rather, the transferred gene is introduced into cells of the recipient organism in situ, that is, within the recipient. In vivo gene therapy has been examined in several animal models (reviewed in Felgner, P. L. and Rhodes, G., *Nature* 349: 351–352 (1991)). Publications have reported the feasibility of direct gene transfer in situ into organs and tissues such as muscle (Ferry, N., et al., *Proc. Natl. Acad. Sci.* 88: 8377–8781 (1991); Quantin, G., et al., *Proc. Natl. Acad. Sci. USA* 89: 2581–2584 (1992)), hematopoietic stem cells (Clapp, D. W., et al., *Blood* 78: 1132–1139 (1991)), the arterial wall (Nabel, E. G., et al., *Science* 244: 1342–1344 (1989)), the nervous system (Price, J. D., et al., *Proc. Natl. Acad. Sci*. 84: 156–160 (1987)), and lung (Rosenfeld, M. A., et al., *Science* 252: 431–434 (1991)). Direct injection of DNA into skeletal muscle (Wolff, J. A., et al., *Science* 247: 1465–1468 (1990)), heart muscle (Kitsis, R. N., et al., *Proc. Natl. Acad. Sci. USA* 88: 4138–4142 (1991)) and injection of DNA-lipid complexes into the vasculature (Lim, C. S., et al., *Circulation* 83: 2007–2011 (1991); Ledere, G. D., et al., *J. Clin. Invest*. 90: 936–944 (1992); Chapman, G. D., et al., *Cire. Res*. 71: 27–33 (1992)) also have been reported to yield a detectable expression level of the inserted gene product(s) in vivo.

Recent gene therapy efforts have been aimed at the identification of various cell types for transformation, including keratinocytes (Morgan, J. R., et al., Science 237: 1476–1479 (1987)), fibroblasts (Palmer, T. D., et al., *Proc. Natl. Acad. Sci*. 88: 1330–1334 (1991); Garver Jr., R. I., et al., *Science* 237: 762–764 (1987); International Patent Application PCT/US92/01890, having publication number WO 92/15676), lymphocytes (Reimann, J. K., et al., *J. Immunol. Methods* 89: 93–101 (1986)), myoblasts (Barr, E. and Leiden, J. M., *Science* 254: 1507–1509 (1991); Dai, Y. et al., PNAS 89: 10892–10895 (1992); Roman, M., et al., *Somatic Cell and Molecular Genetics* 18: 247–258 (1992)), smooth muscle cells (Lynch, C. M. et al, *Proc. Natl. Acad. Sci. USA* 89: 1138–1142 (1992)), and epithelial cells (Nabel, E. G., et al., *Science* 244: 1342–1344 (1989)), International Patent Application PCT/US89/05575 (having publication number WO 90/06997), the contents of which references and patent/patent applications are incorporated herein by reference.

The delivery of an effective dose of a prophylactic or therapeutic agent in situ depends on the efficiency of transfection (or transduction) as well as the number of target cells. Epithelial cell-based gene therapy, in particular, involves a relatively small area available in situ for receiving genetically modified epithelial cells. The delivery of an effective dose of prophylactic or therapeutic agent in situ thus depends upon the total number of implanted epithelial cells.

In one embodiment of the invention, exogenous genetic material (e.g., a cDNA encoding a polypeptide of the present invention) is introduced into a syngeneic host cell ex vivo or in vivo by genetic transfer methods, such as transfection or transduction, to provide a genetically modified host cell. Various expression vectors (ie., vehicles for facilitating delivery of exogenous genetic material into a target cell) are known to one skilled in the art.

Transfection refers to the insertion of nucleic acid into a mammalian host cell using physical or chemical methods. Several transfection techniques are known to those of ordinary skill in the art including: calcium phosphate DNA co-precipitation (*Methods in Molecular Biology*, Vol. 7, *Gene Transfer and Expression Protocols*, Ed. E. J. Murray, Humana Press (1991)); DEAE-dextran; electroporation; cationic liposome-mediated transfection; and tungsten particle-facilitated microparticle bombardment (Johnston, S. A., *Nature* 346: 776–777 (1990)). Strontium phosphate DNA co-precipitation (Brash D. E. et al. *Molec. Cell. Biol*. 7: 2031–2034 (1987)) is a preferred transfection method.

In contrast, transduction refers to the process of transferring nucleic acid into a cell using a DNA or RNA virus. A RNA virus (ie., a retrovirus) for transferring a nucleic acid into a cell is referred to herein as a transducing chimeric retrovirus. Exogenous genetic material contained within the retrovirus is incorporated into the genome of the transduced host cell. A host cell that has been transduced with a chimeric DNA virus (e.g., an adenovirus carrying a cDNA encoding a therapeutic agent) will not have the exogenous genetic material incorporated into its genome, but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i. e., enhancers) required to obtain the desired gene transcription activity. For the purpose of this discussion an enhancer is simply any non-translated DNA sequence which works contiguous with the coding sequence (in cis) to change the basal transcription level dictated by the promoter. Preferably, the exogenous genetic material is introduced into the host cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or housekeeping functions: hypoxanthine phosphoribosyl transferase (HPRT), dihydrofolate reductase (DHFR) (Scharfinann et al., *Proc. Natl. Acad. Sci. USA* 88: 4626–4630 (1991)), adenosine deaminase, phosphoglycerol kinase (PGK), pyruvate kinase, phosphoglycerol mutase, the beta -actin promoter (Lai et al., *Proc. Natl. Acad. Sci. USA* 86: 10006–10010 (1989)), and other constitutive promoters known to those of skill in the art. In addition, many viral promoters function constitutively in eukaryotic cells. These include: the early and late promoters of SV40, the long terminal repeats (LTRs) of Moloney Leukemia Virus and other retroviruses, and the thymidine kinase promoter of Herpes Simplex Virus, among many others. Accordingly, any such constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response, and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified host cell. If the gene encoding the prophylactic or therapeutic agent is under the control of an inducible promoter, delivery of the agent in situ is triggered by exposing the genetically modified cell in situ to conditions for permitting transcription of the prophylactic or therapeutic agent, e.g., by intraperitoneal injection of specific inducers of the inducible promoters which control transcription of the agent. For example, in situ expression by genetically modified host cells of a therapeutic agent encoded by a gene under the control of the metallothionein promoter, is enhanced by contacting the genetically modified cells with a solution containing the appropriate (i. e., inducing) metal ions in situ.

Accordingly, the amount of therapeutic agent that is delivered in situ is regulated by controlling such factors as: (1) the nature of the promoter used to direct transcription of the inserted gene (i. e., whether the promoter is constitutive or inducible, strong or weak); (2) the number of copies of the exogenous gene that are inserted into the host cell; (3) the number of transduced/transfected host cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the prophylactic or therapeutic agent by the genetically modified host cell. Selection and optimization of these factors for delivery of an effective dose of a particular prophylactic or therapeutic agent is deemed to be within the scope of one of skill in the art, taking into account the above-disclosed factors and the clinical profile of the patient.

In addition to at least one promoter and at least one heterologous nucleic acid encoding the prophylactic or therapeutic agent, the. expression vector preferably includes a selection gene, for example, a neomycin resistance gene, for facilitating selection of host cells that have been transfected or transduced with the expression vector. Alternatively, the host cells are transfected with two or more expression vectors, at least one vector containing the gene(s) encoding the prophylactic or therapeutic agent(s), the other vector containing a selection gene. The selection of a suitable promoter, enhancer, selection gene and/or signal sequence is deemed to be within the scope of one skilled in the art.

The prophylactic or therapeutic agent can be targeted for delivery to an extracellular, intracellular or membrane location. If it is desirable for the gene product to be secreted from the host cells, the expression vector is designed to include an appropriate secretion signal sequence for secreting the therapeutic gene product from the cell to the extracellular milieu. If it is desirable for the gene product to be retained within the host cell, this secretion signal sequence is omitted. In a similar manner, the expression vector can be constructed to include retention signal sequences for anchoring the prophylactic or therapeutic agent within the host cell plasma membrane. For example, membrane proteins have hydrophobic transmembrane regions that stop translocation of the protein in the membrane and do not allow the protein to be secreted. The construction of an expression vector including signal sequences for targeting a gene product to a particular location is deemed to be within the scope of one of skill in the art.

In an embodiment, vectors for mammalian host cell gene therapy are viruses, more preferably replication-deficient viruses (described in detail below). Exemplary viral vectors are derived from: Harvey Sarcoma Virus; Rous Sarcoma Virus, MPSV, Moloney murine leukemia virus and DNA viruses (e.g., adenovirus). See Temin, H., Retrovirus vectors for gene transfer, in *Gene Transfer*, Kucherlapati R, Ed., pp. 149–187 (Plenum 1986).

Replication-deficient retroviruses are capable of directing synthesis of virion proteins, but are incapable of making infectious particles. Accordingly, these genetically altered retroviral expression vectors have general utility for high-efficiency transduction of genes in cultured cells, and specific utility for use in the method of the present invention. Such retroviruses further have utility for the efficient transduction of genes into host cells in vivo. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in Kriegler, M. *Gene Transfer and Expression, A Laboratory Manual*, W. H. Freeman Co., N.Y. (1990) and Murray, E. J., ed. *Methods in Molecular Biology*, Vol. 7, Humana Press Inc., Clifton, N.J. (1991).

The major advantage of using retroviruses for gene therapy is that the viruses insert the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types (see e.g., Hilberg et al., *Proc. Natl. Acad. Sci. USA* 84: 5232–5236 (1987); Holland et al., *Proc. Natl. Acad. Sci. USA* 84: 8662–8666 (1987); Valerio et al., *Gene* 84: 419–427 (1989)). In vivo gene therapy using replication-deficient retroviral vectors to deliver a therapeutically effective amount of a therapeutic agent can be efficacious if the efficiency of transduction is high and/or the number of target cells available for transduction is high.

Yet another viral candidate useful as an expression vector for transformation of mammalian host cells is the adenovirus, a double-stranded DNA virus. The adenovirus is frequently responsible for respiratory tract infections in humans and thus appears to have an avidity for the epithelium of the respiratory tract (Straus, S., *The Adenovirus*, H. S. Ginsberg, Editor, Plenum Press, NY, p. 451–496 (1984)). Moreover, the adenovirus is infective in a wide range of cell types, including, for example, muscle and epithelial cells (Larrick, J. W. and Burck, K. L., *Gene Therapy. Application of Molecular Biology*, Elsevier Science Publishing Co., Inc., NY, p. 71–104 (1991)). The adenovirus also has been used as an expression vector in muscle cells in vivo (Quantin, B., et al., *Proc. Natl. Acad. Sci. USA* 89: 2581–2584 (1992)).

Like the retrovirus, the adenovirus genome is adaptable for use as an expression vector for gene therapy, i.e., by removing the genetic information that controls production of the virus itself (Rosenfeld, M. A., et al., *Science* 252:431–434 (1991)). Because the adenovirus functions in an extrachromosomal fashion, the recombinant adenovirus does not have the theoretical problem of insertional mutagenesis.

Thus, as will be apparent to one skilled in the art, a variety of suitable viral expression vectors are available for transferring exogenous genetic material into mammalian host cells. The selection of an appropriate expression vector to express an agent for the identification, prevention or treatment of microbial infection amenable to gene replacement therapy and the optimization of the conditions for insertion of the selected expression vector into the cell are within the scope of one of skill in the art without the need for undue experimentation.

In an alternative embodiment, the expression vector is in the form of a plasmid, which is transferred into the target host cells by one of a variety of methods: physical (e.g. microinjection (Capecchi, M. R., *Cell* 22: 479–488 (1980)), electroporation (Andreason, G. L. and Evans, G. A. *Biotechniques* 6: 650–660 (1988)), scrape loading, microparticle bombardment (Johnston, S. A., *Nature* 346: 776–777 (1990)) or by cellular uptake as a chemical complex (e.g., calcium or strontium co-precipitation, complexation with lipid, complexation with ligand) (*Methods in Molecular Biology*, Vol. 7, *Gene Tranafer and Expressing Protocols*, Ed. E. J. Murray, Humana Press (1991)). Several commercial products are available for cationic liposome complexation including Lipofectin (Life Technologies, Inc., Gaithersburg, Md.) (Felgner, P. L., et al., *Proc. Natl. Acad. Sci.* 84: 7413–7417 (1987)) and Transfectam™ (ProMega, Madison, Wis.) (Behr, J. P., et al., *Proc. Natl. Acad. Sci. USA* 86: 6982–6986 (1989); Loeffler, J. P., et al., *J Neurochem.* 54: 1812–1815 (1990)). However, the efficiency of transfection by these methods is highly dependent on the nature of the target cell and accordingly, the conditions for optimal transfection of nucleic acids into host cells using the above-mentioned procedures must be optimized. Such optimization is within the scope of one of skill in the art.

In an embodiment, the preparation of genetically modified host cells contains an amount of cells sufficient to deliver a prophylactically or therapeutically effective dose of a signal transduction mediator of the present invention to the recipient in situ. The determination of an effective dose of the prophylactic or therapeutic agent for a known microbial infection is within the scope of one of skill in the art. Thus, in determining the effective dose, the skilled artisan would consider the condition of the patient, the severity of the condition, as well as the results of clinical studies of the prophylactic or therapeutic agent being administered.

If the genetically modified host cells are not already present in a pharmaceutically acceptable carrier, they are placed in such a carrier prior to administration to the recipient. Such pharmaceutically acceptable carriers include, for example, isotonic saline and other buffers as appropriate to the patient and therapy. The genetically modified cells are administered by, for example, intraperitoneal injecting or implanting the cells or a graft or capsule containing the cells in a host cell-compatible site of the recipient. As used herein, host cell-compatible site refers to a structure, cavity or fluid of the recipient into which the genetically modified cell(s), host cell graft, or encapsulated host cell expression system can be implanted, without triggering adverse physiological consequences. Representative host cell-compatible sites include, for example, the peritoneal, pleural and pericardial cavities. Preferably, the host cell-compatible site communicates with the lymphatic system, thereby enabling delivery of the therapeutic agent to the vascular system.

In one embodiment, the host cell-compatible site may be denuded prior to implanting the cells. Exemplary denuding methods include but are not limited to: (1) injection of distilled water into the site (e.g., the peritoneal cavity) for 20 minutes, followed by scraping off a portion of the epithelial layer; (2) injection of 0.1% buffered trypsin for 20 minutes followed by scraping; (3) removal of epithelial cells by gentle scraping with a cell scraper and (4) touching a piece of Gelfilm (Upjohn, Kalamazoo, Mich.) to the endothelium.

The genetically modified host cells are implanted in a host cell-compatible site, alone or in combination with other genetically modified host cells. Thus, the instant invention embraces a method for modifying the epithelial system of a recipient by using a mixture of genetically modified host cells, such that a first modified cell expresses a first prophylactic or therapeutic agent of the present invention and a second modified cell expresses a second prophylactic or therapeutic agent. Other genetically modified cell types (e.g., hepatocytes, smooth muscle cells, fibroblasts, glial cells, mesothelial cells or keratinocytes) can be added, together with the genetically altered epithelial cells, to produce expression of a complex set of introduced genes. Moreover, more than one recombinant gene can be introduced into each genetically modified cell on the same or different vectors, thereby allowing the expression of multiple prophylactic or therapeutic agents of the present invention by a single cell.

The instant invention further embraces an epithelial cell graft. The graft comprises a plurality of the above-described genetically modified cells attached to a support that is suitable for implantation into a mammalian recipient, preferably into the oral cavity. The support can be formed of a natural or synthetic material. According to another aspect of the invention, an encapsulated host cell expression system is provided. The encapsulated system includes a capsule suitable for implantation into a mammalian recipient and a plurality of the above-described genetically modified host cells contained therein. The capsule can be formed of a synthetic or naturally-occurring material. The formulation of such capsules is known to one of ordinary skill in the art. In contrast to the host cells that are directly implanted into the mammalian recipient (i.e., implanted in a manner such that the genetically modified cells are in direct physical contact with the host cell-compatible site), the encapsulated cells remain isolated (i.e., not in direct physical contact with the site) following implantation. Thus, the encapsulated host cell system is not limited to a capsule including genetically-modified non-immortalized host cells, but may contain genetically modified immortalized host cells.

The invention has been disclosed broadly and illustrated in reference to representative embodiments described above. Those skilled in the art will recognize that various modifications can be made to the present invention without departing from the spirit and scope thereof.

We claim:

1. A purified polypeptide comprising an amino acid sequence having at least 95% sequence identity with an amino acid sequence selected from the group consisting of SEQ ID NOS: 1, 4, 6, and 7, wherein said polypeptide is capable of catalyzing the transfer of a phosphate group from a donor molecule to an acceptor molecule.

2. A composition for treating a disease in a mammal comprising the polypeptide of claim 1 and a pharmaceutically acceptable sterile vehicle.

3. The composition of claim 2, wherein said mammal is a human.

4. The vaccine of claim 2, wherein said disease is cardiac disease.

5. A kit for detecting the expression of a protein capable of regulating signal transduction, comprising the polypeptide of claim 1.

6. The kit of claim 5, further comprising a detectable label selected from the group consisting of calorimetric, enzymatic, chemiluminescent, fluorescent and radioactive.

7. A kit for detecting the expression of a protein capable of acting as a donor molecule or an acceptor molecule of a phosphate group, comprising the polypeptide of claim 1.

8. The kit of claim 7, further comprising a detectable label selected from the group consisting of calorimetric, enzymatic, chemiluminscent, fluorescent and radioactive.

* * * * *